United States Patent
Tobias

(10) Patent No.: US 6,683,690 B1
(45) Date of Patent: Jan. 27, 2004

(54) INTRALUMINAL RADIATION TREATMENT SYSTEM

(75) Inventor: Martin B. Tobias, Longmount, CO (US)

(73) Assignee: Novoste Corporation, Norcross, GA (US)

( * ) Notice: Subject to any disclaimer, the term of this patent is extended or adjusted under 35 U.S.C. 154(b) by 0 days.

(21) Appl. No.: 09/444,195

(22) Filed: Nov. 19, 1999

Related U.S. Application Data

(62) Division of application No. 08/936,058, filed on Sep. 23, 1997, now Pat. No. 6,013,020.
(60) Provisional application No. 60/052,708, filed on Jul. 16, 1997, provisional application No. 60/041,090, filed on Mar. 14, 1997, and provisional application No. 60/026,566, filed on Sep. 23, 1996.

(51) Int. Cl.$^7$ .......................... G01N 21/55; A61M 29/02
(52) U.S. Cl. .......................................... 356/445; 600/7
(58) Field of Search ................... 356/445, 318, 356/73, 326, 446–448, 408, 433, 435, 436, 39; 600/7

(56) References Cited

U.S. PATENT DOCUMENTS

| | | | |
|---|---|---|---|
| 2,750,517 A | | 6/1956 | Baum |
| 2,965,761 A | | 12/1960 | Horvath |
| 3,088,032 A | | 4/1963 | Brunton |
| 3,532,888 A | | 10/1970 | Masefield et al. |
| 4,233,517 A | | 11/1980 | van't Hooft |
| 4,584,991 A | | 4/1986 | Tokita et al. |
| 4,733,653 A | | 3/1988 | Leung et al. |
| 4,755,058 A | * | 7/1988 | Shaffer ...................... 356/408 |
| 5,030,194 A | | 7/1991 | van't Hooft |
| 5,103,395 A | | 4/1992 | Spako et al. |
| 5,654,803 A | * | 8/1997 | Howard, III et al. ....... 356/446 |
| 5,683,345 A | | 11/1997 | Waksman et al. |
| 5,791,345 A | * | 8/1998 | Ishihara et al. ............. 128/637 |
| 5,899,882 A | | 5/1999 | Waksman et al. ............. 604/96 |
| 6,008,889 A | * | 12/1999 | Zeng et al. ................... 356/73 |
| 6,013,020 A | * | 1/2000 | Meloul et al. .................. 600/7 |
| 6,055,060 A | * | 4/2000 | Bolduan et al. ............. 356/433 |

FOREIGN PATENT DOCUMENTS

| | | |
|---|---|---|
| CA | 1 197 631 | 12/1985 |
| DE | 1 895 963 | 12/1960 |
| GB | 1 219 604 | 1/1971 |
| GB | 1 558 127 | 12/1979 |
| SU | 279814 | 7/1975 |

OTHER PUBLICATIONS

International Search Report re application No. PCT/US97/16856, mailed Jan. 12, 1998.

* cited by examiner

Primary Examiner—Frank G. Font
Assistant Examiner—Layla Lauchman
(74) Attorney, Agent, or Firm—Cook, Alex, McFarron, Manzo, Cummings & Mehler, Ltd.

(57) ABSTRACT

A transfer device and catheter assembly for the delivery of treatment elements to a selected location within the intraluminal passageways of a patient as part of an intraluminal radiation system. The transfer device includes a gate member that permits the treatment elements to have the transfer device only if the catheter is attached thereto. A pressure indicator provides a visual indication of the fluid pressure within the transfer device, and provides for a release of the fluid if the pressure exceeds a predetermined pressure. The catheter also includes detents to secure it to the transfer device and which must be manually activated to remove the catheter from the transfer device. The transfer device includes circuiting that determines whether the treating elements reside within the transfer device based upon the reflectivity of the treating elements. A method for determining whether treating elements reside in the catheter is also disclosed.

24 Claims, 48 Drawing Sheets

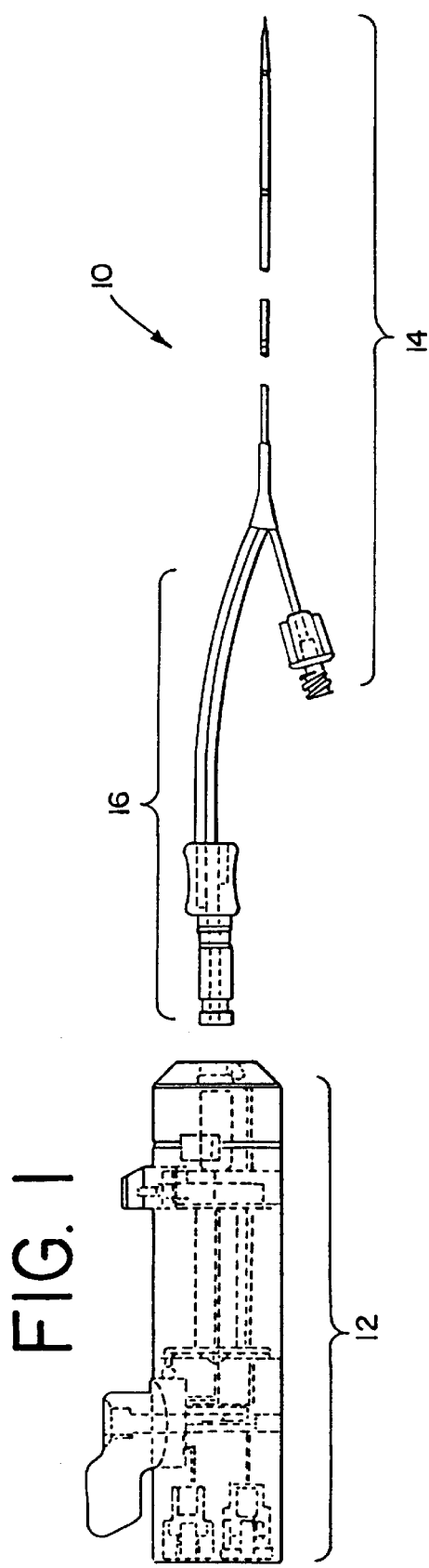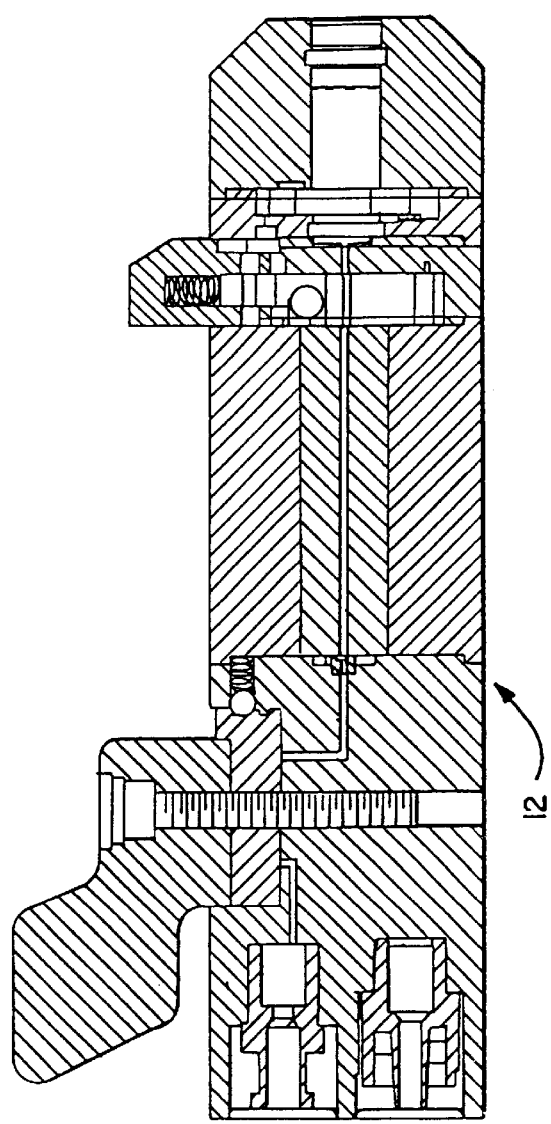

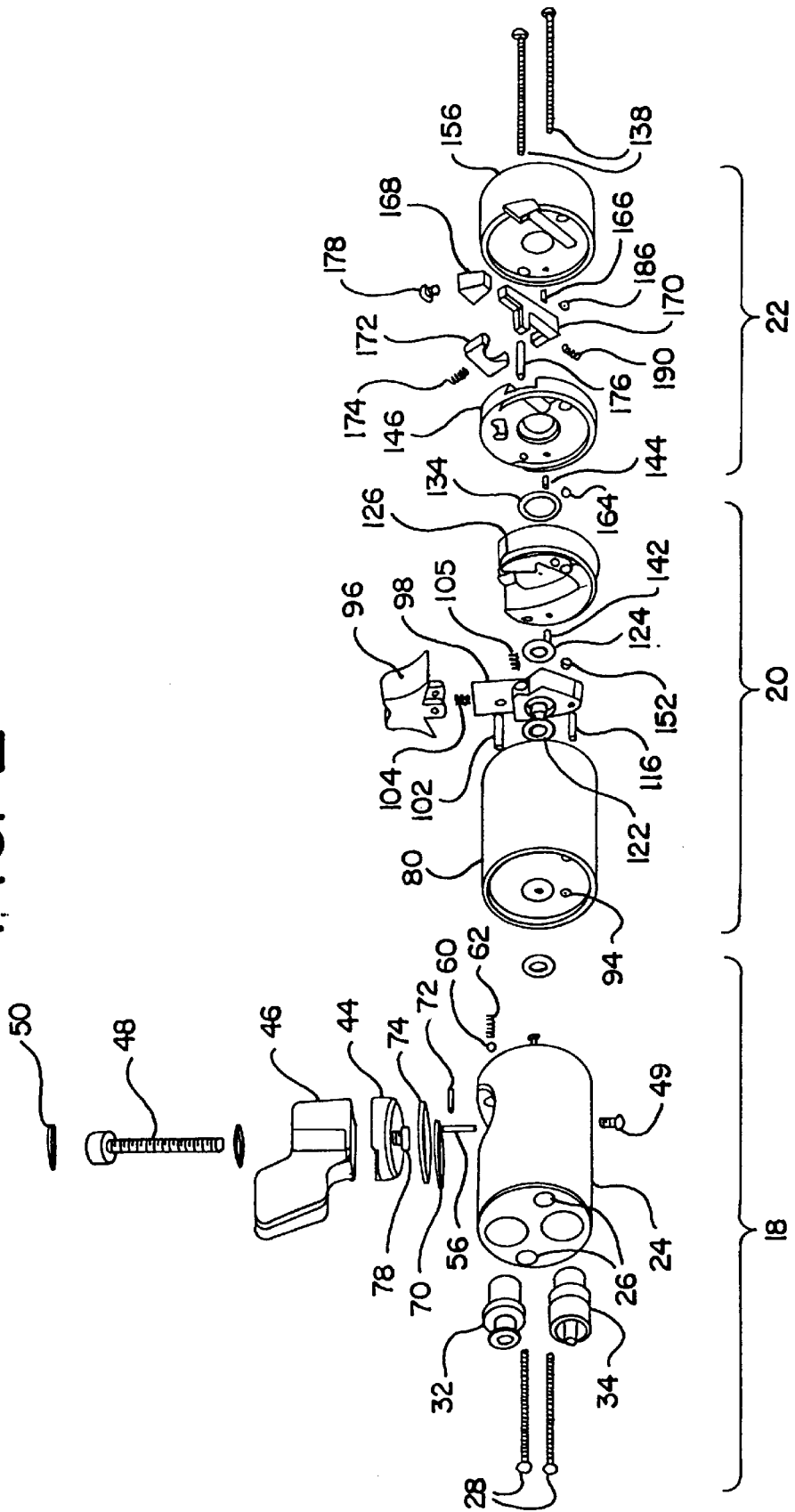

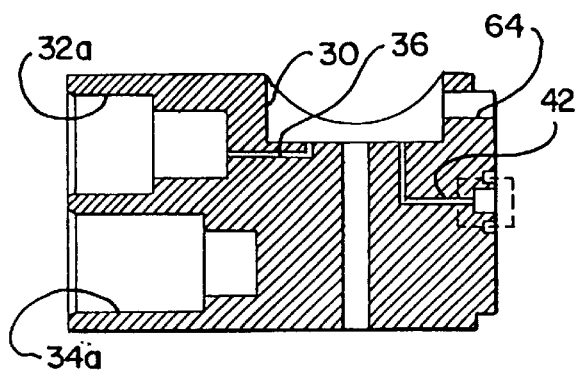
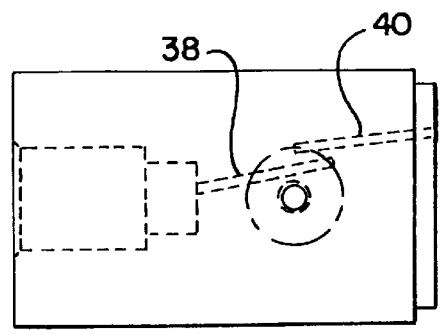
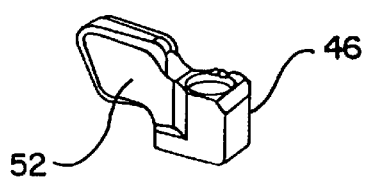
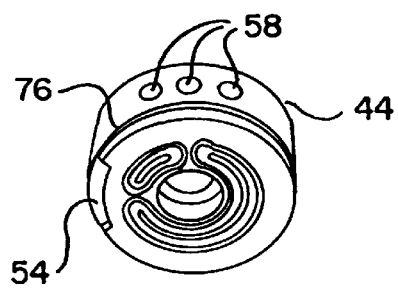
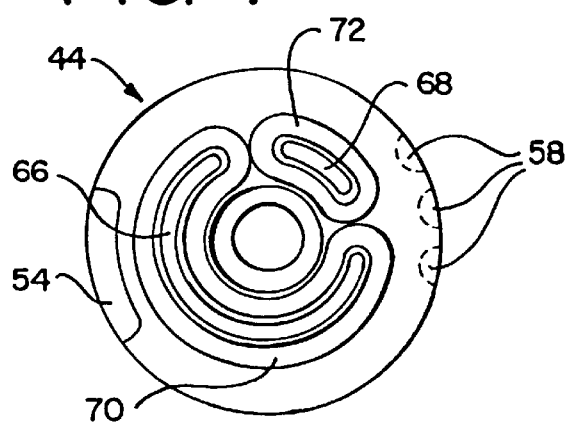
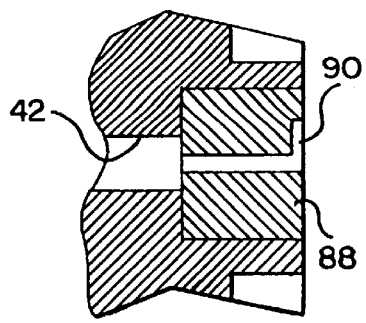

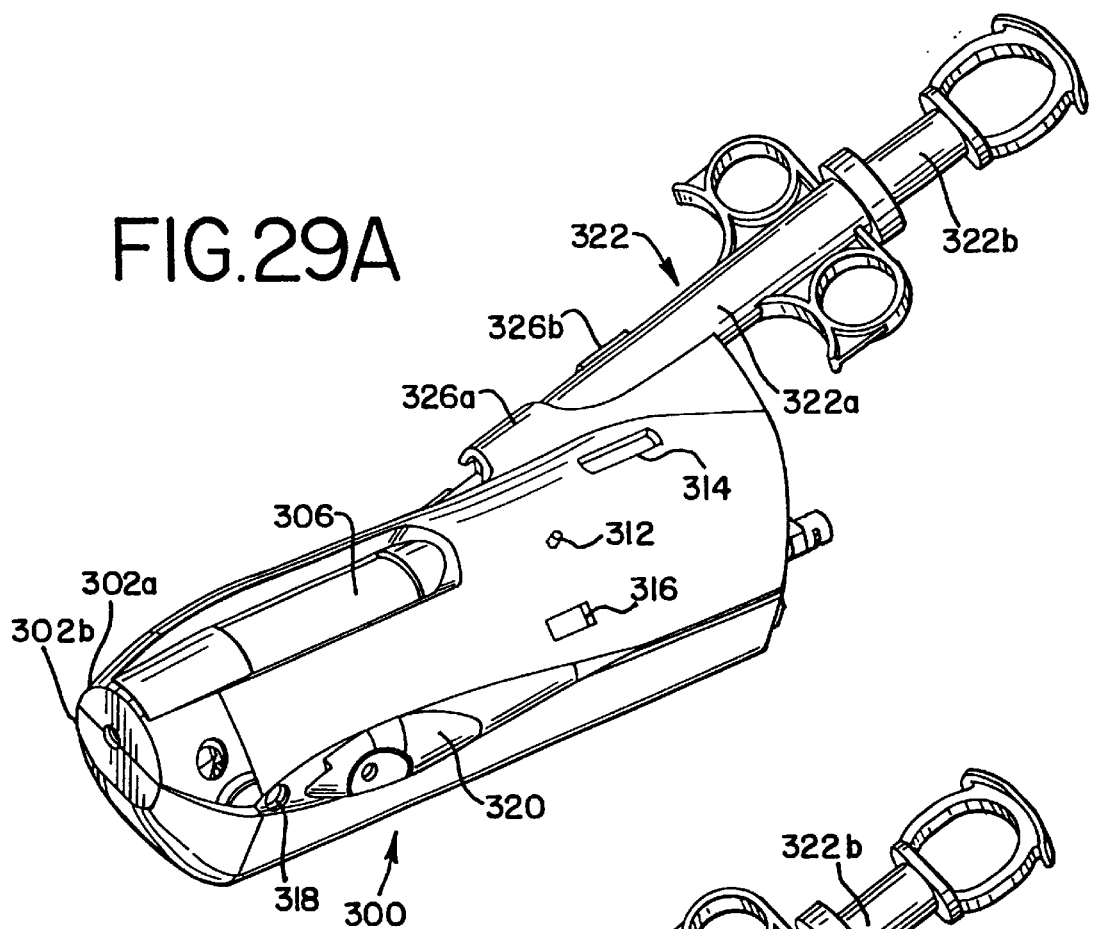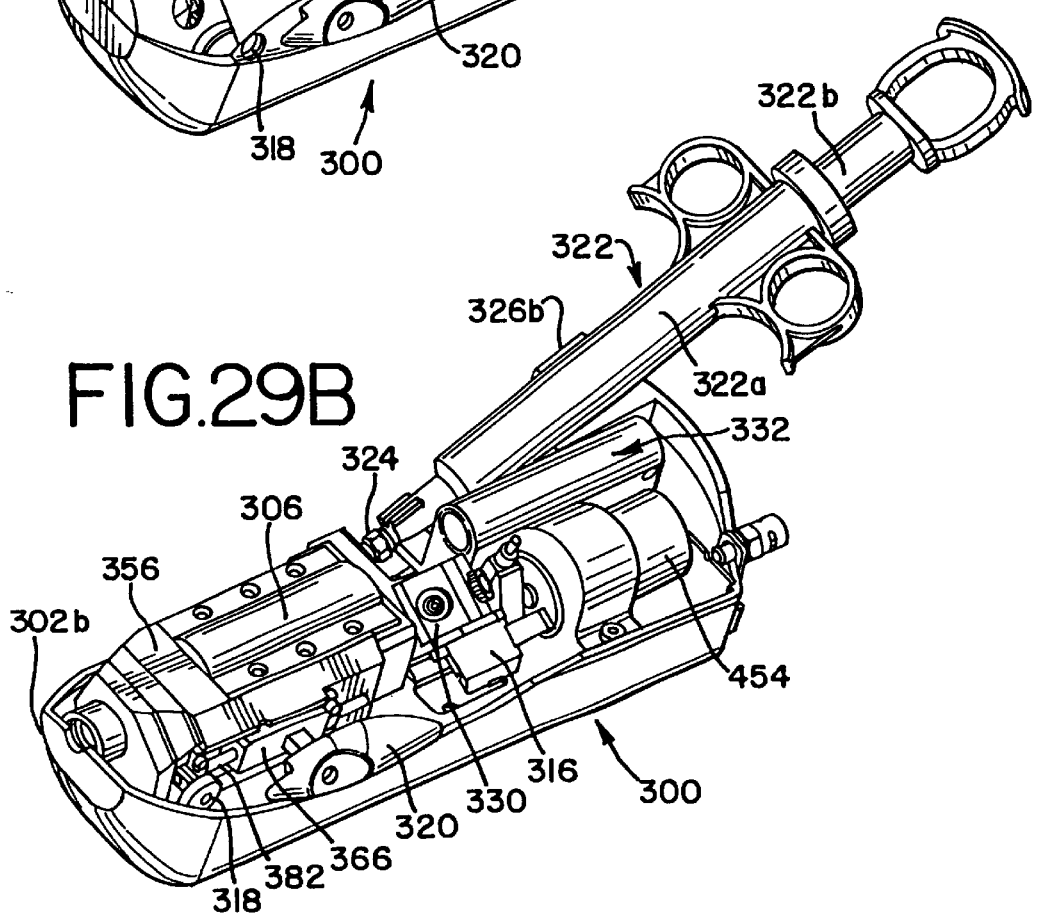

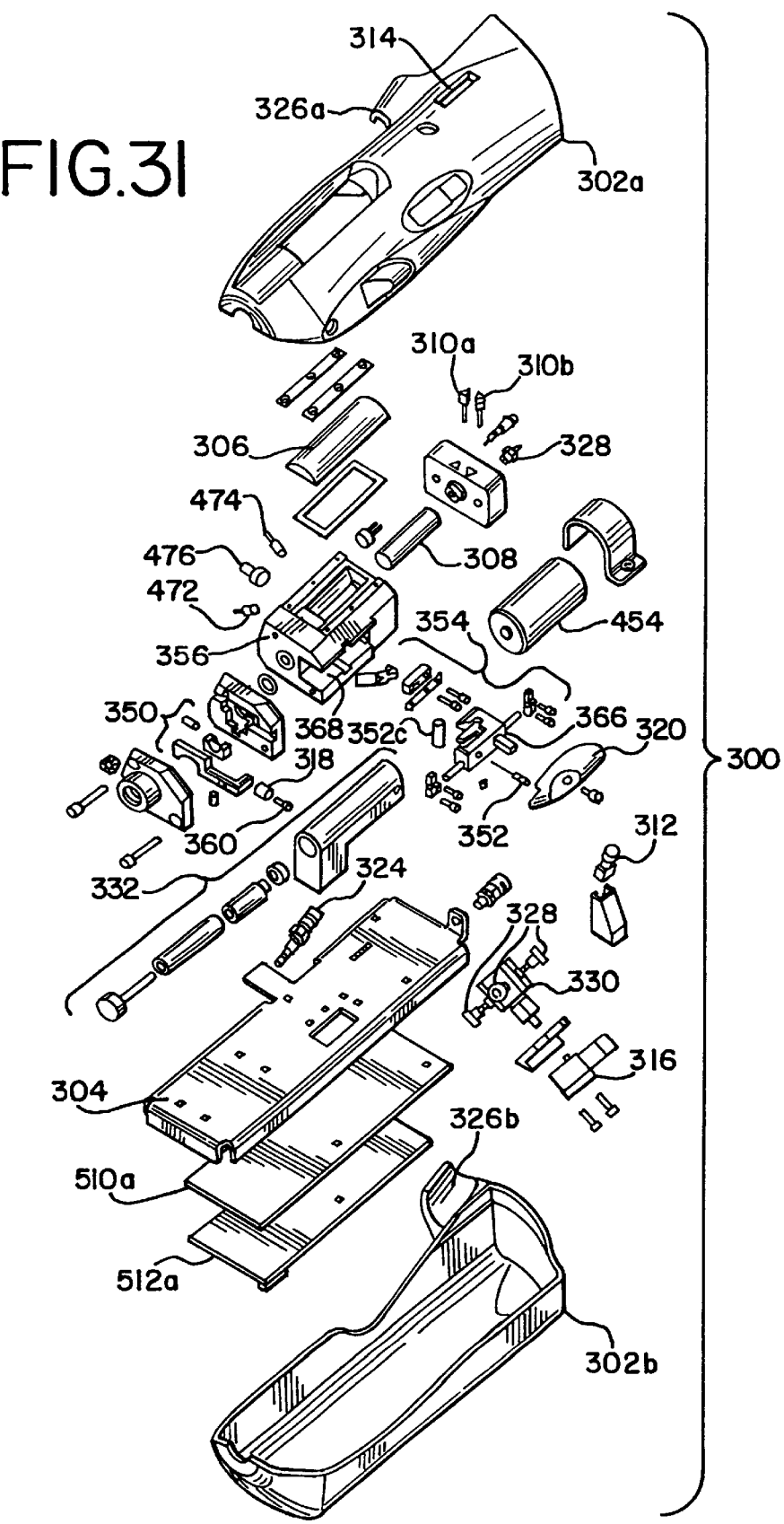

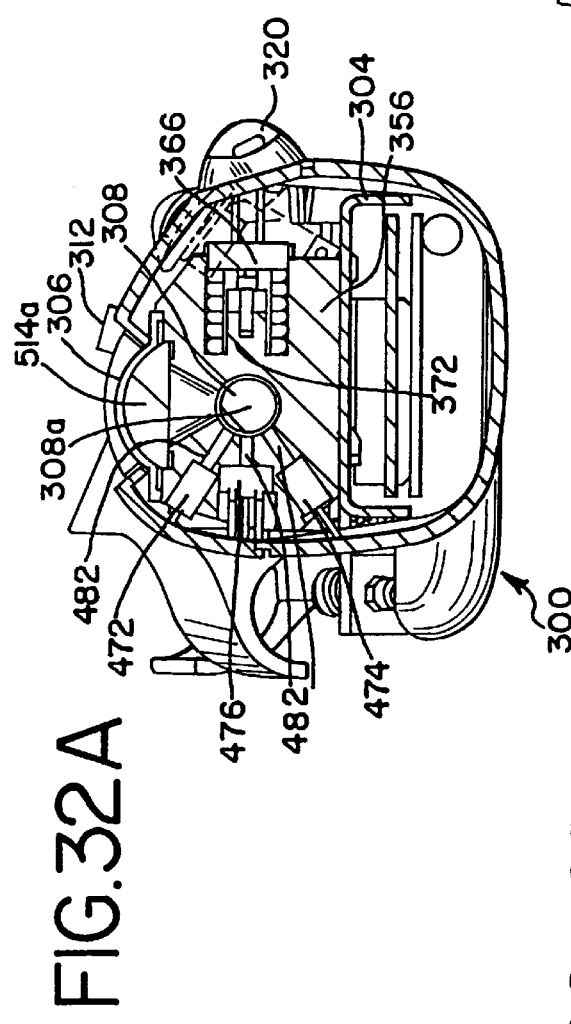
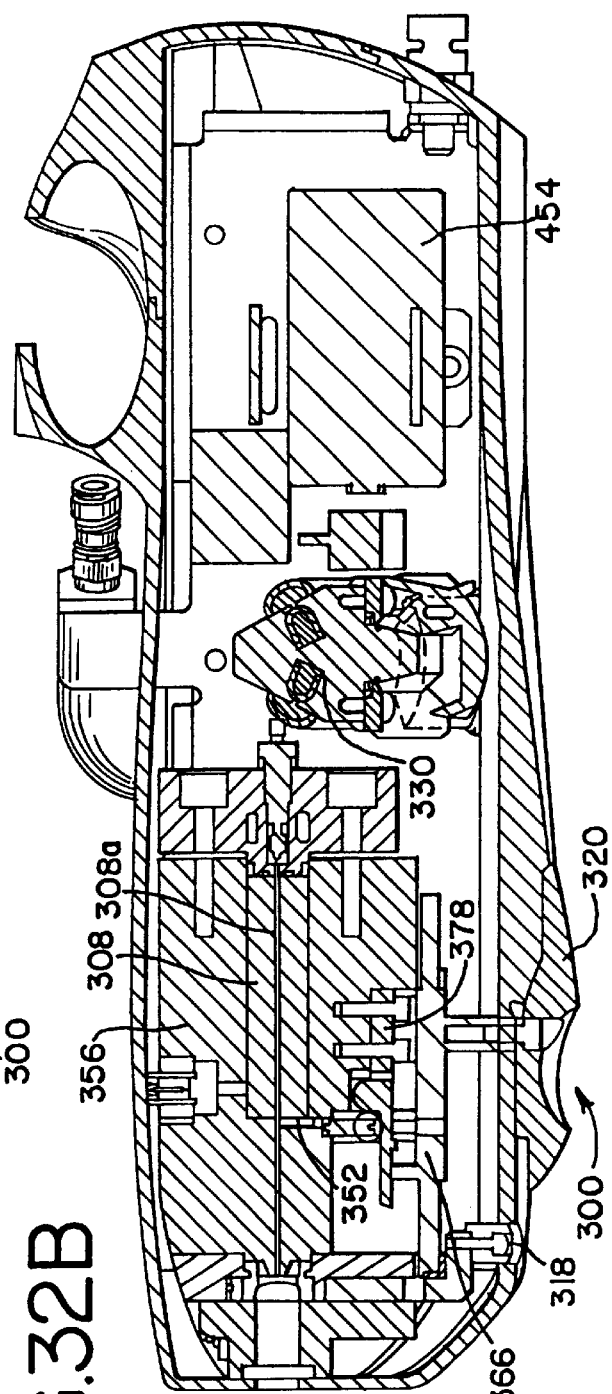
FIG.32A
FIG.32B

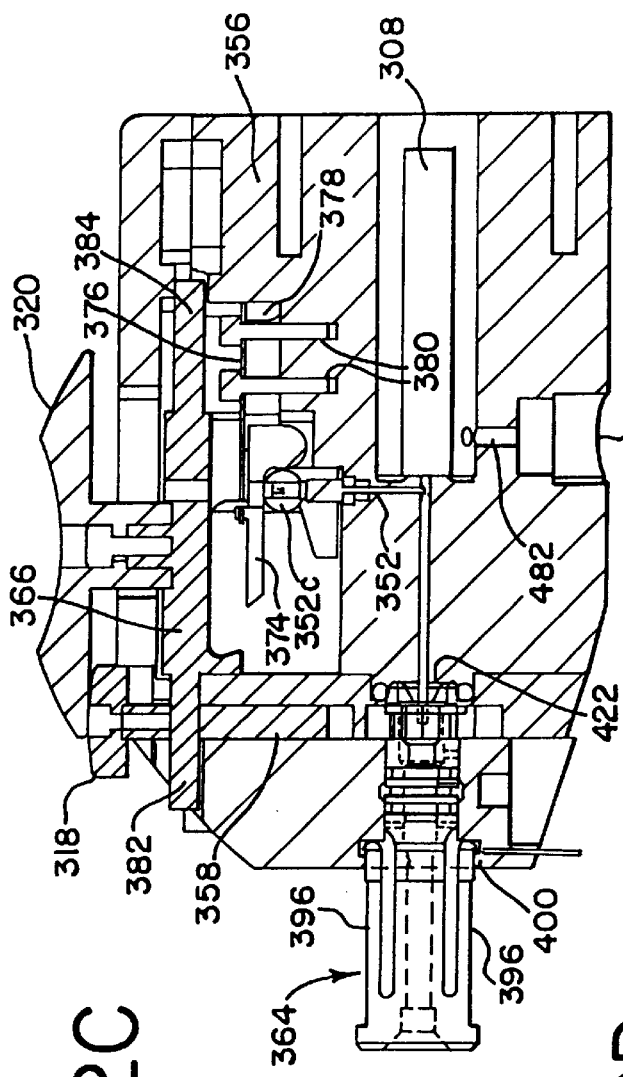
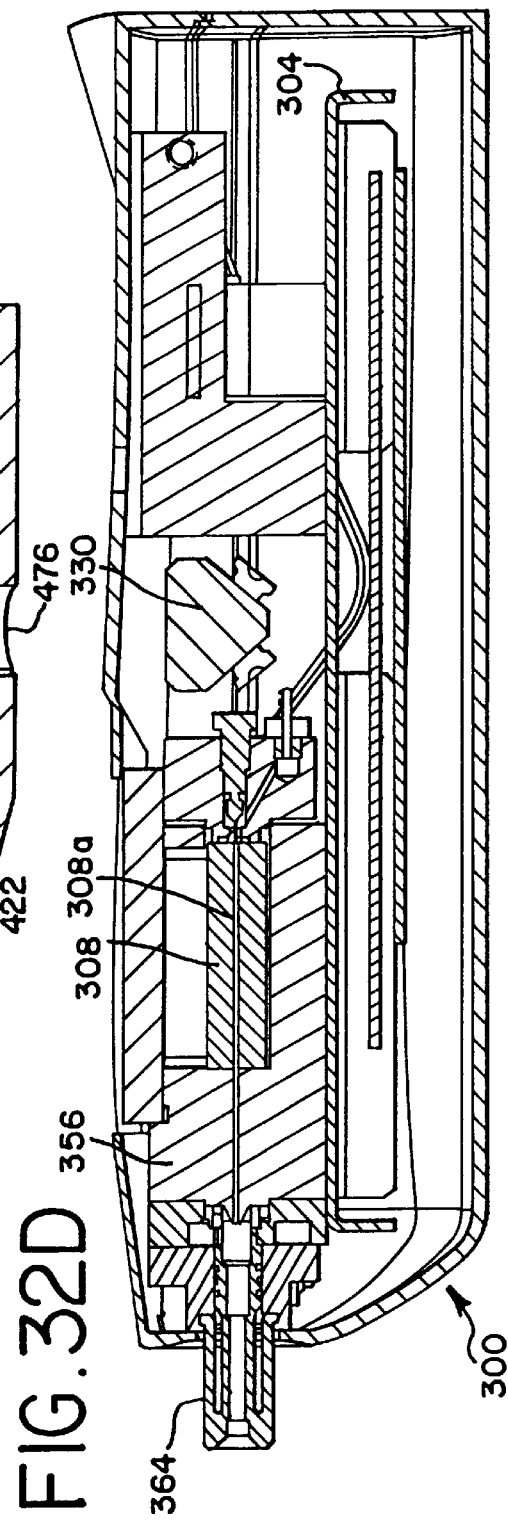
FIG. 32C
FIG. 32D

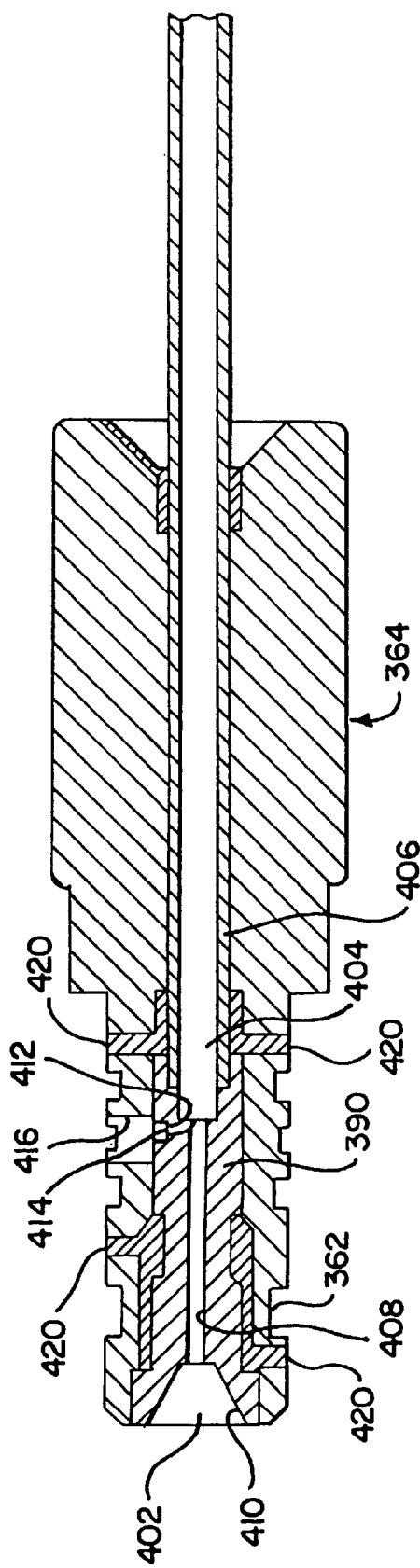
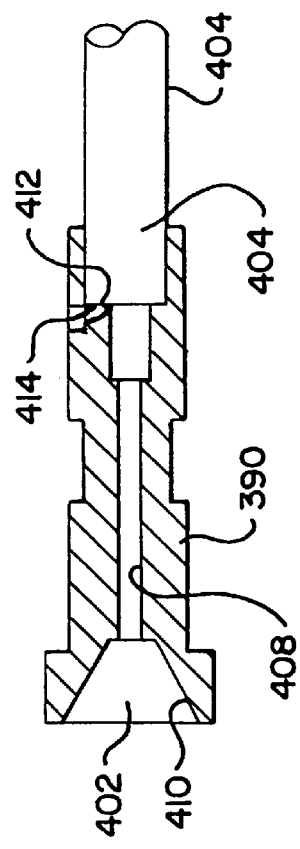

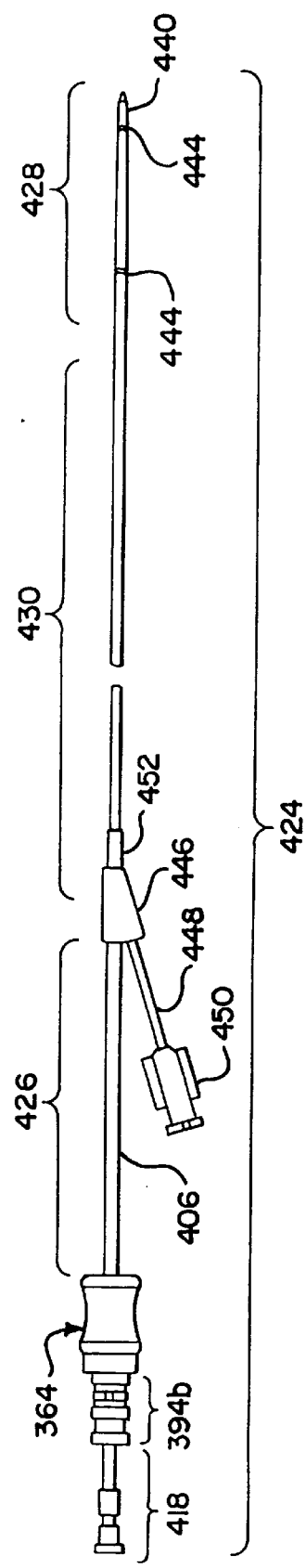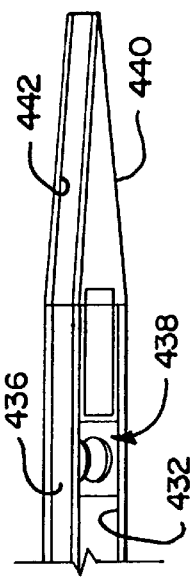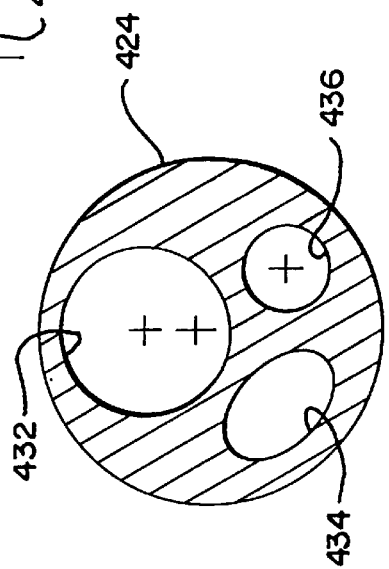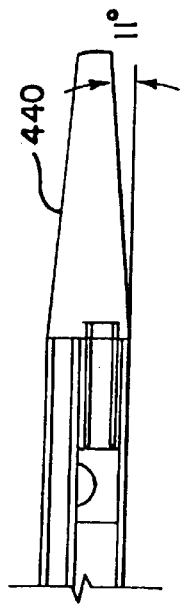

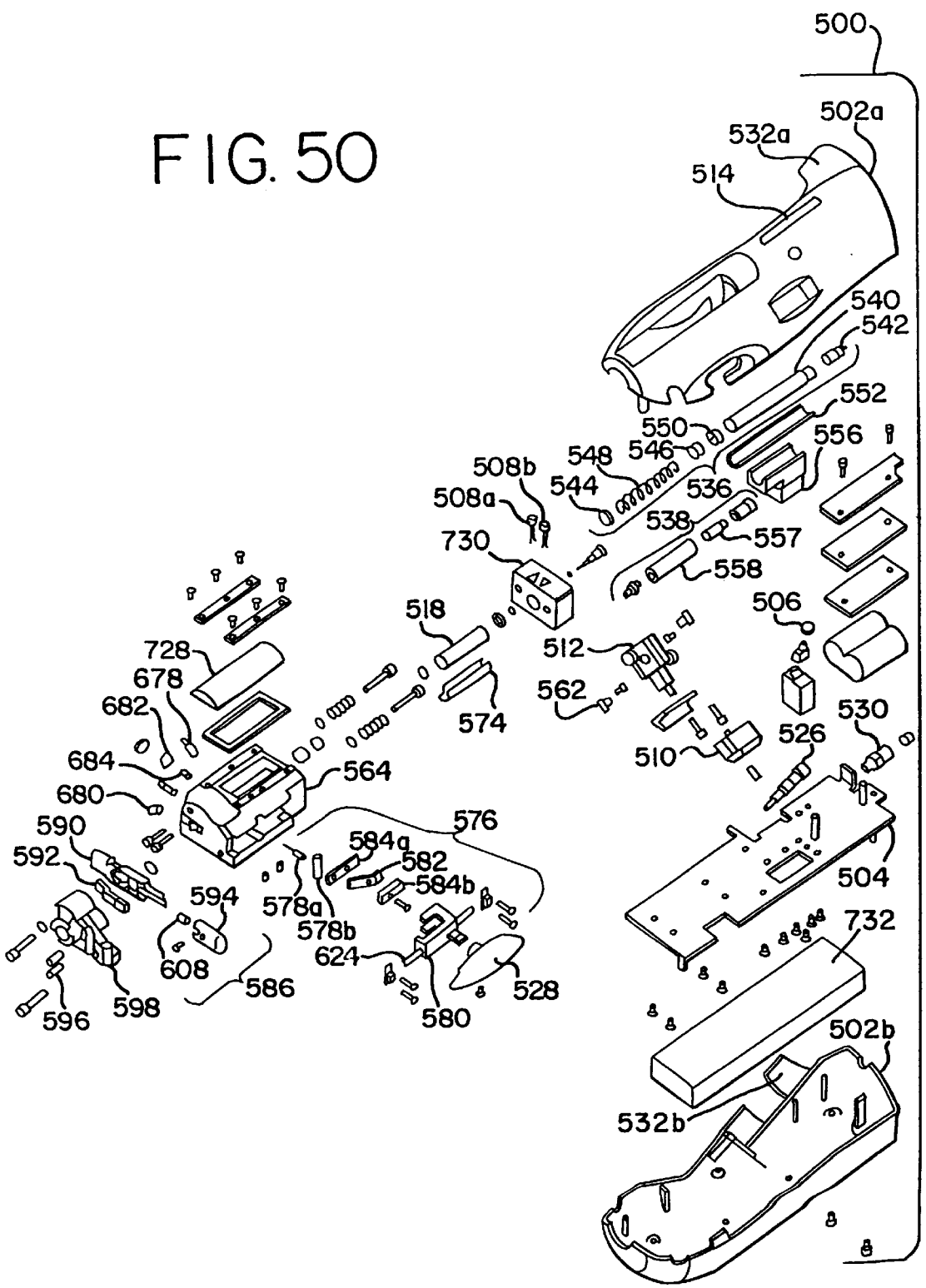

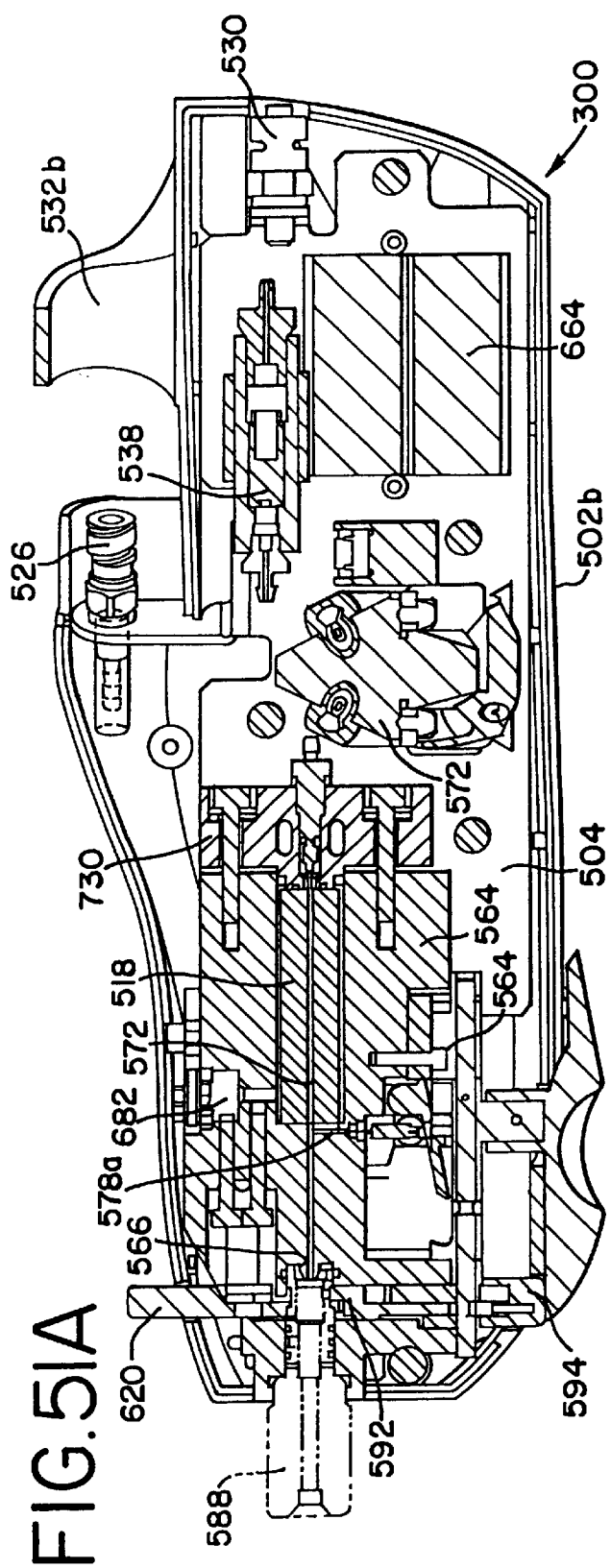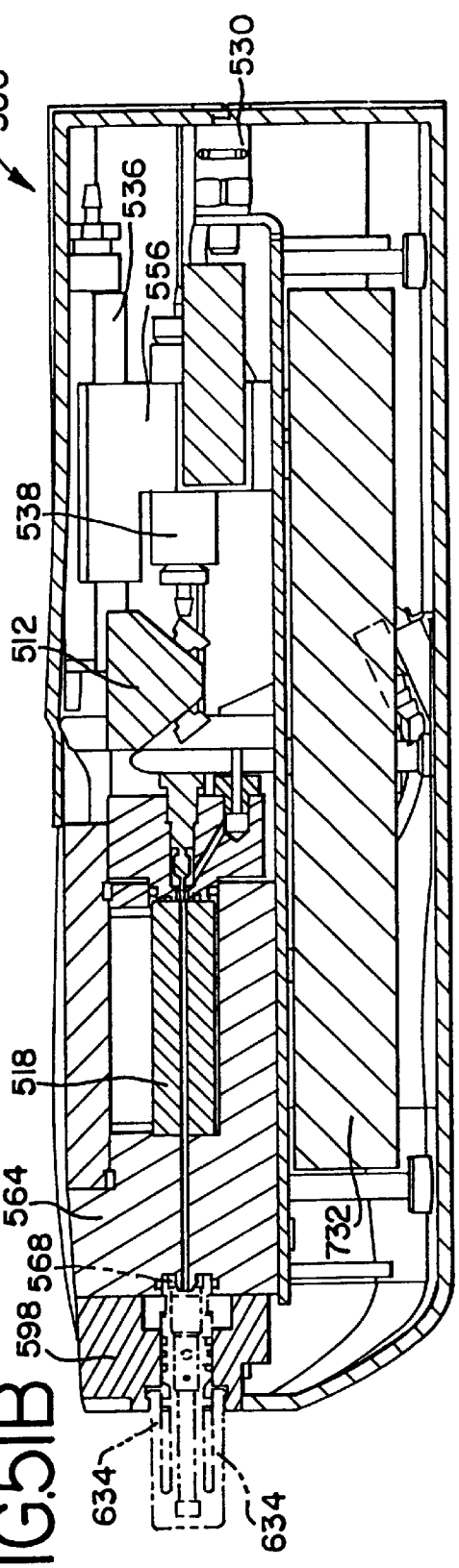

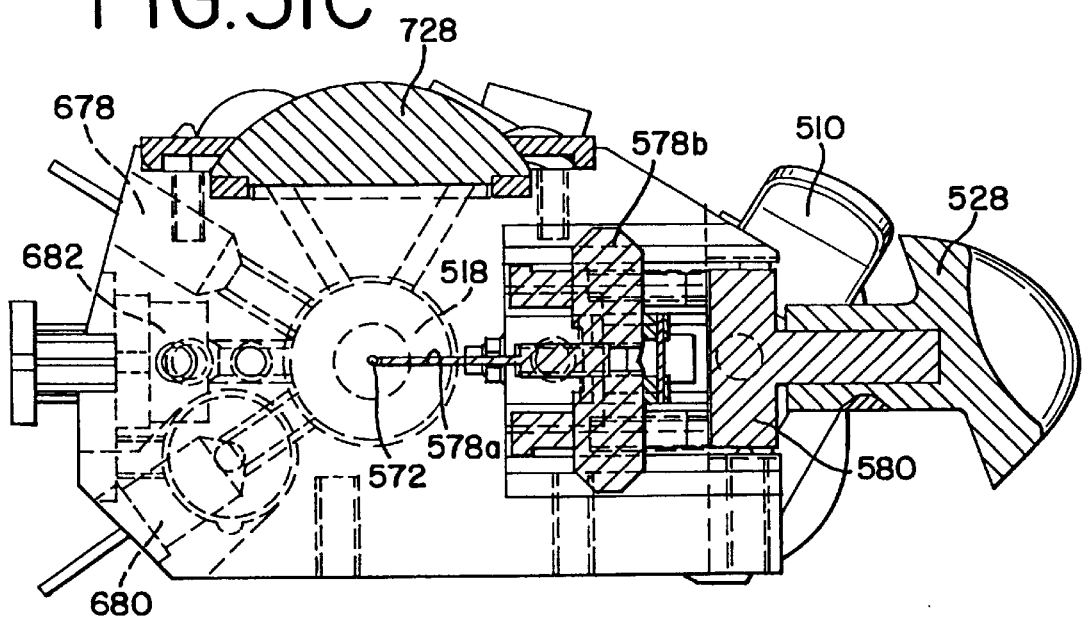
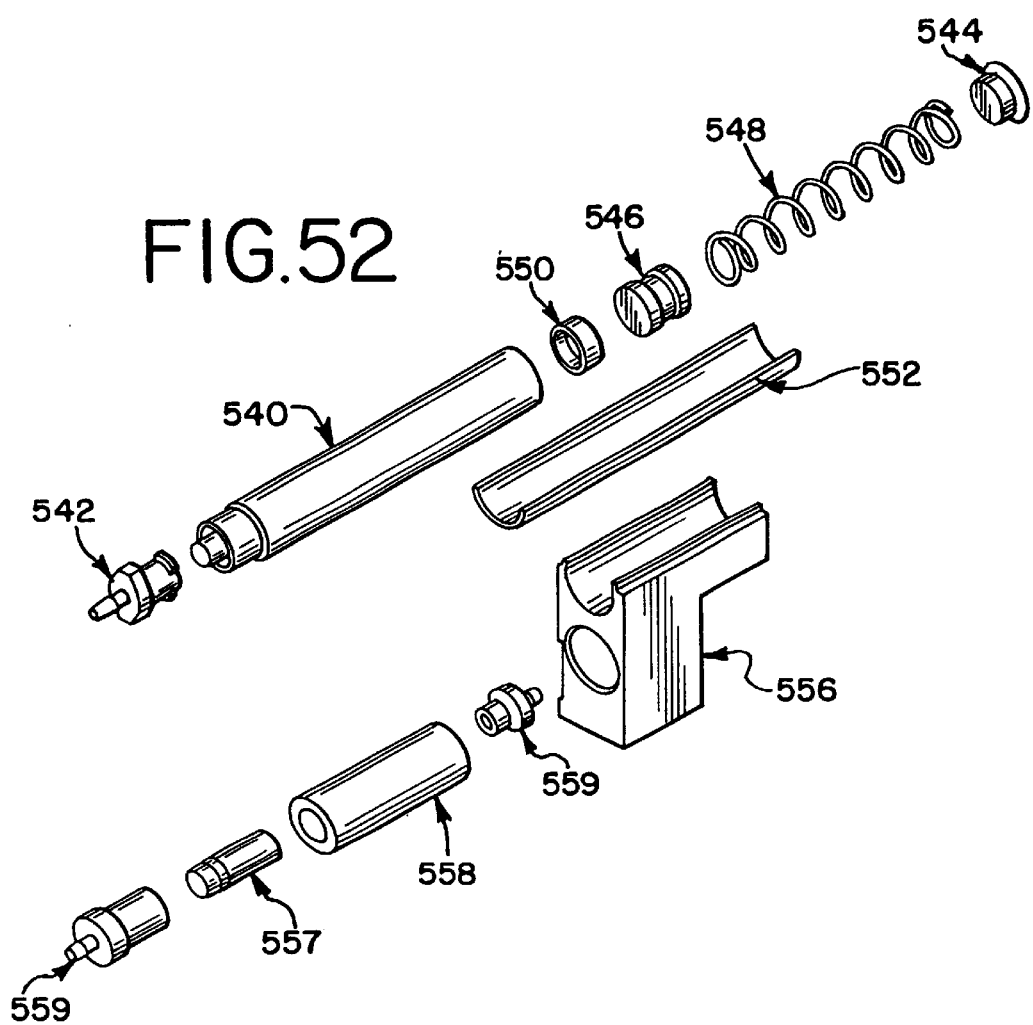

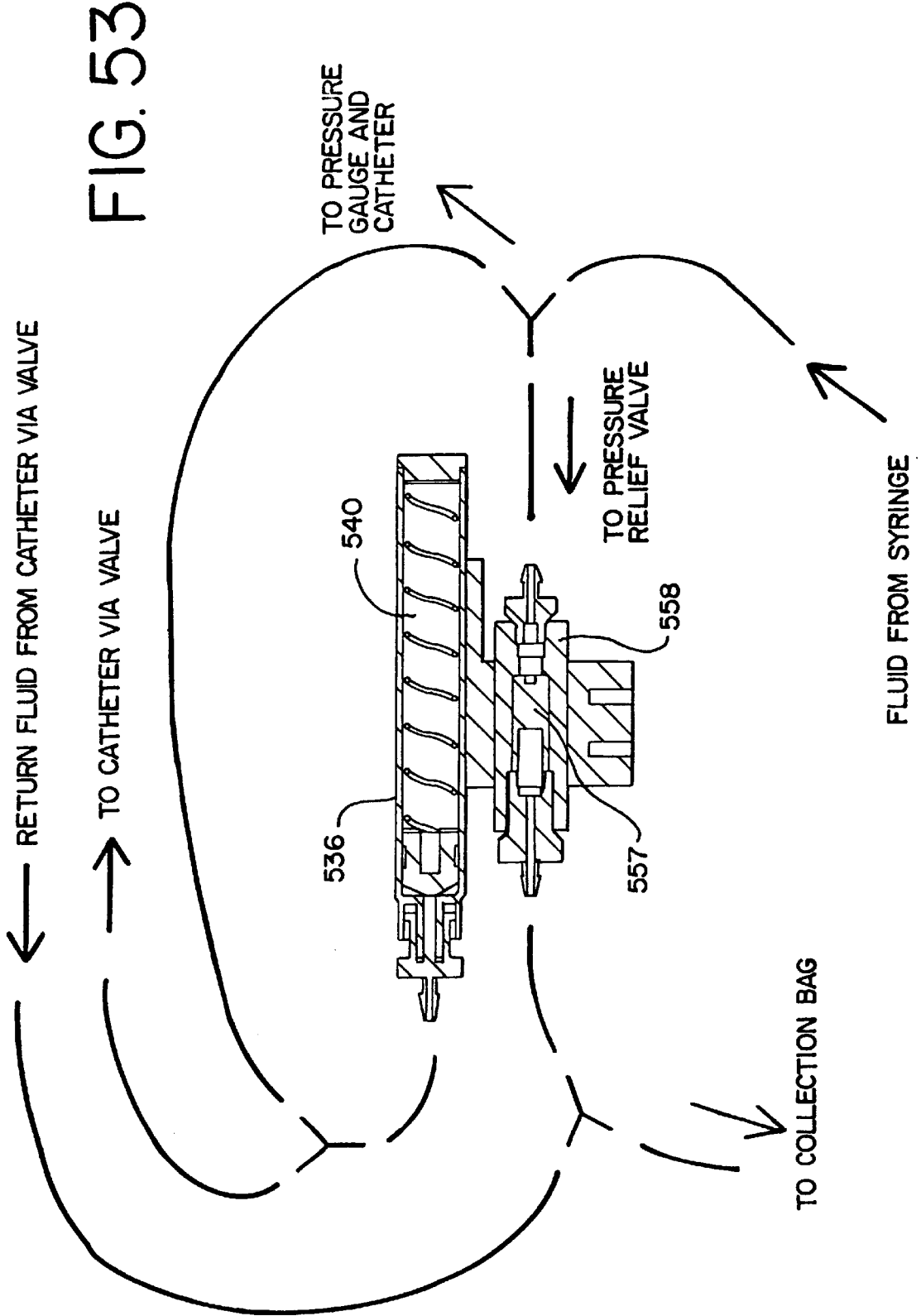

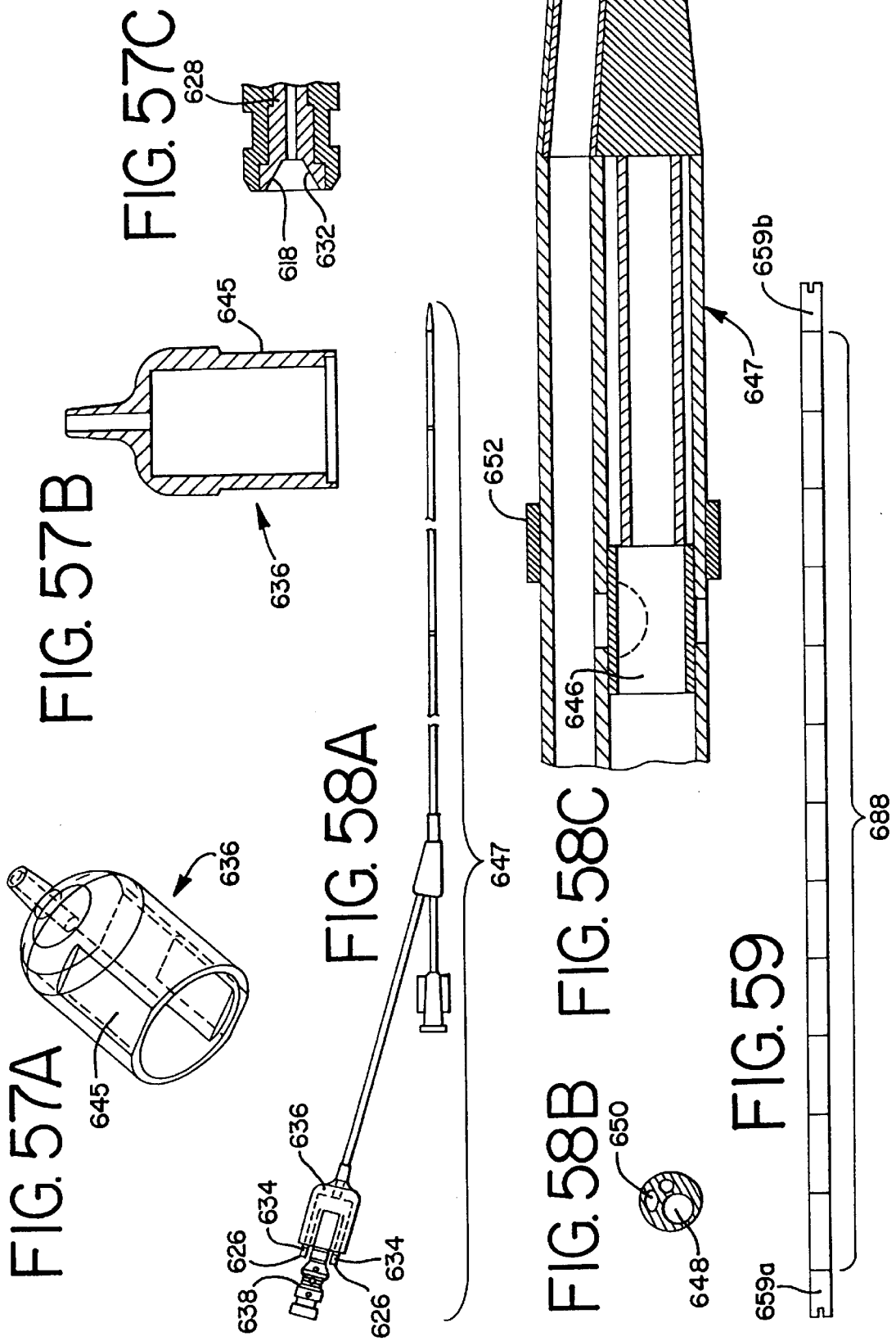

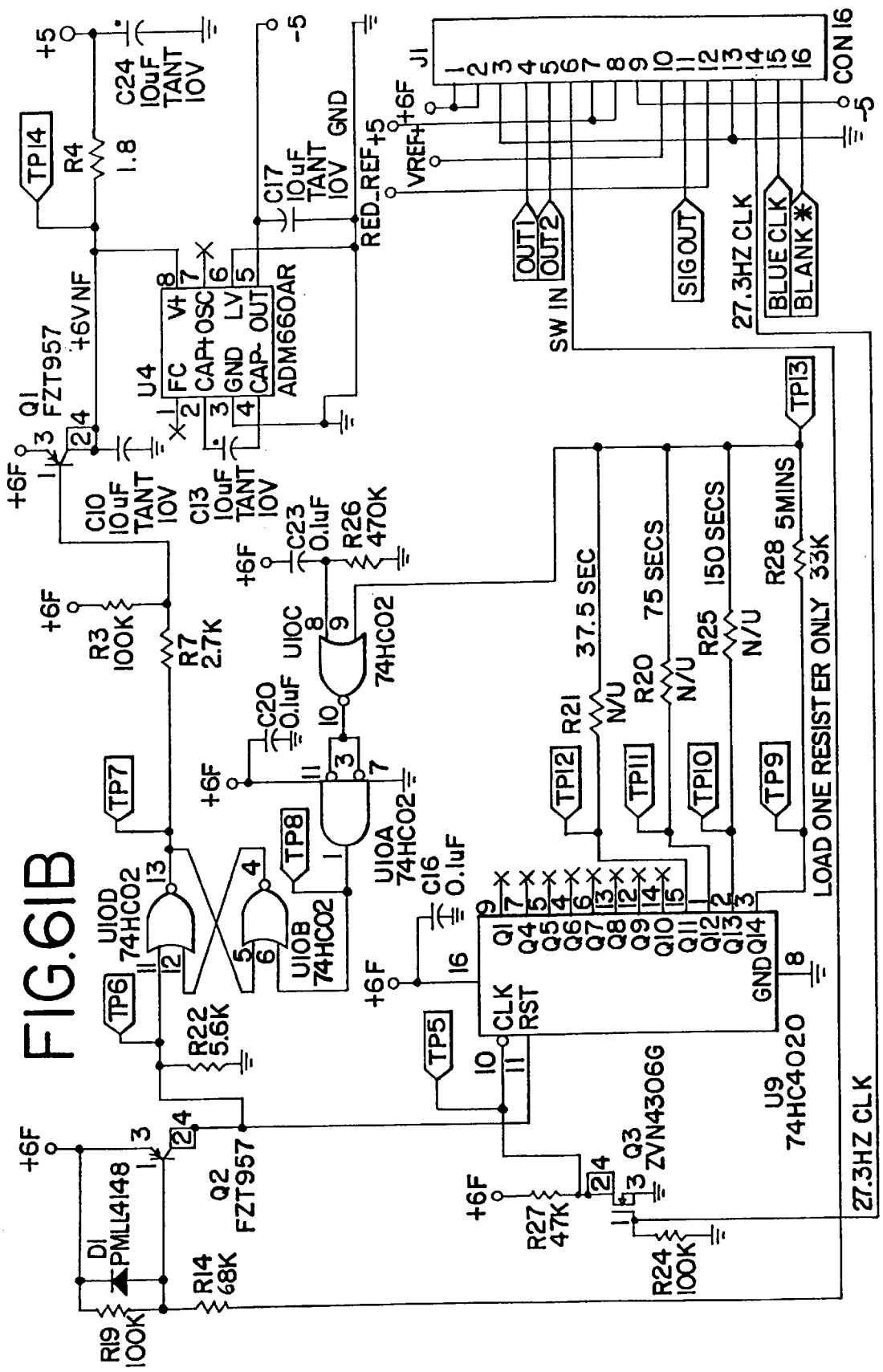

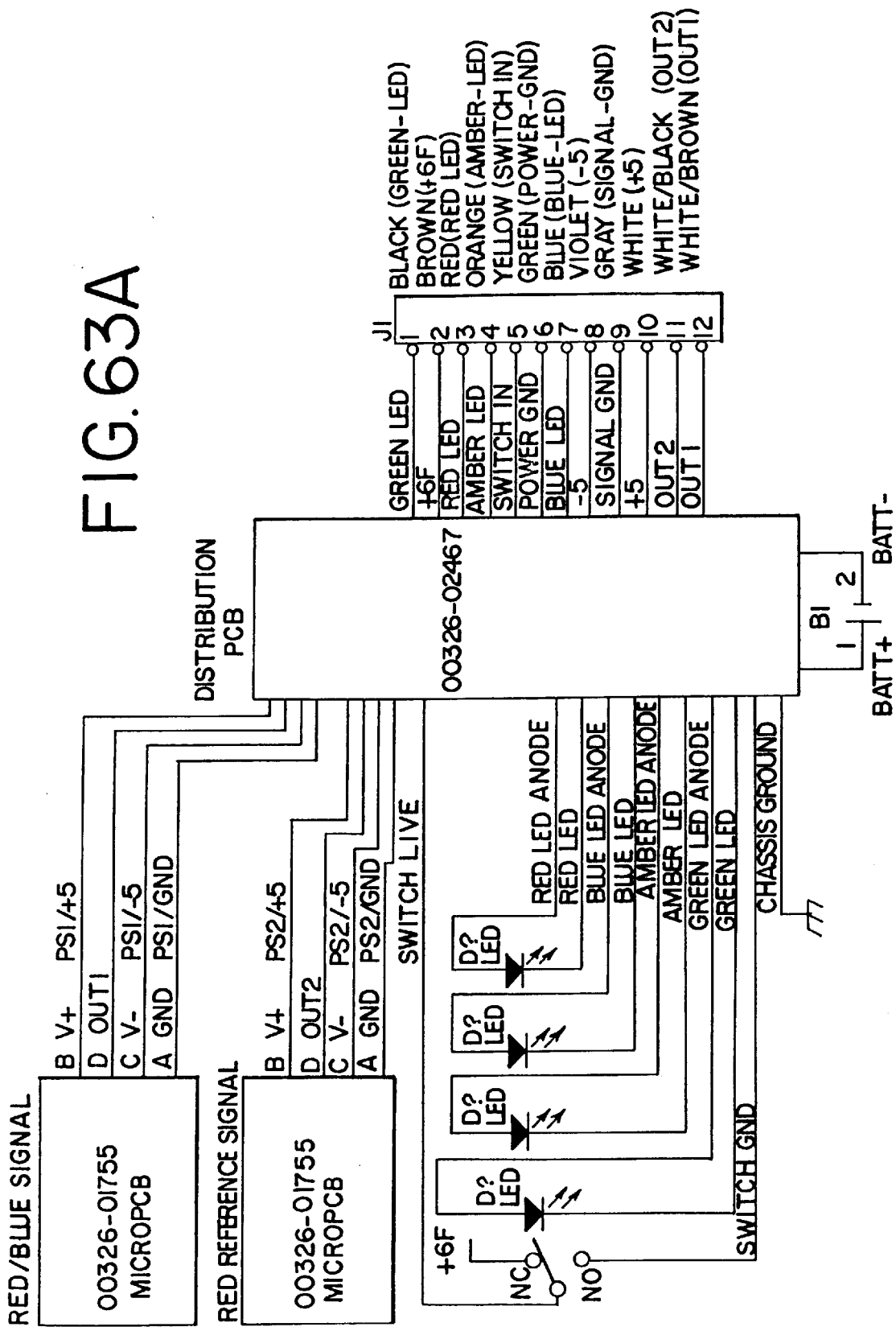

INTRALUMINAL RADIATION TREATMENT SYSTEM

CROSS REFERENCE TO RELATED APPLICATIONS

This is a division, of application Ser. No. 08/936,058, filed Sep. 23, 1997, now U.S. Pat. No. 6,013,020.

This application claims the benefits of provisional applications serial Nos. 60/026,566, filed Sep. 23, 1996; No. 60/041,090, filed Mar. 14, 1997; and No. 60/052,708, filed Jul. 16, 1997.

The present invention relates generally to an intraluminal radiation system for the delivery of treatment elements by way of a catheter to a selected location within the intraluminal passageways of a patient. More particularly, the present invention relates to an improved transfer device for handling the treating elements and delivering them to the catheter and an improved catheter assembly.

BACKGROUND OF THE INVENTION

Since the late 1970's balloon angioplasty techniques have become widely used for opening blockages in coronary arteries. Briefly, the enlargement of the artery is achieved by advancing a balloon catheter into a narrowed portion of the artery and inflating the balloon to expand the diameter of the artery, thus opening the artery for greater blood flow. Atherectomy techniques, in which blockages are removed or reduced in size, have also been used to the same end.

While balloon angioplasty has proved an effective way of opening the coronary arteries, in a significant number of cases the arteries will narrow again at the location where the balloon was expanded, such narrowing being termed restenosis. Restenosis is believed to be caused by formation of scar tissue at the site of the angioplasty that results from the injury to the artery caused by the inflation of the balloon.

More recently, intraluminal radiation has been used after angioplasty or atherectomy to treat the affected area of the artery to inhibit cell proliferation and wound healing response and, consequently, help to prevent restenosis. Methods and apparatus for such intraluminal radiation treatment are disclosed in the co-pending application, Ser. No. 08/628,231, filed Apr. 4, 1996, which is incorporated herein by reference. This application generally discloses an apparatus comprising a catheter, which is inserted intraluminally into the patient and advanced to the site of the area to be treated, and a transfer device for facilitating either the hydraulic or pneumatic advancement and retrieval of individual radioactive treating elements or "seeds" along the catheter to and from the treatment site.

As with any device inserted into the vascular system, it must have sufficient integrity to insure that no pieces or elements are separated from or exit the device into the vascular system. This is particularly true for the treating elements which are moved to and from the distal end of the catheter. Additionally, because the device is intended to use radioactive treating elements, there is a heightened need for safety to prevent any unintended exposure of either the patient or the user to radioactivity.

Use of the apparatus described in the above-identified co-pending application has suggested several areas where the device could be improved to reduce the possibility of having treatment elements escape from the system, thus enhancing patient and user safety.

Consequently, it is the principal object of the present invention to provide a transfer device and catheter assembly that has additional safeguards to protect the patient and user.

More particularly, it is an object of the present invention to provide a transfer device/catheter assembly in which the catheter cannot be inadvertently detached from the transfer device unless all the treating elements reside within the transfer device. Similarly, it is an object of the present invention to provide a transfer device/catheter assembly in which none of the treating elements can exit the transfer device unless a catheter is connected thereto.

It is a further object to insure that the hydraulic or pneumatic pressures to which the transfer device/catheter assembly is subjected during the advancement and retrieval of the treating elements does not exceed a predetermined "safe" pressure.

It is an additional object to provide a method and system for detecting the presence or absence of treating elements in the transfer device and for providing a visual indication of such presence or absence of treating elements.

SUMMARY OF THE INVENTION

These objects, and others that will become apparent upon reference to the following detailed description are accomplished in one aspect by an actuator assembly for the transfer device that includes a gate member that is moveable between a first position that prevents treating elements from entering the lumen of the catheter and a second position that permits treating elements to enter the lumen. The gate member is moveable into the second position only if the catheter is attached to the transfer device. The actuator assembly includes a switch member biased into a first position that prevents movement of the gate member into its second position unless the switch member is moved out of a first position that interferes with the movement of the gate member upon the catheter connector being received in the central opening of the transfer device. Additionally, a trigger member that is moveable into locking engagement with the connector when the connector is received in the central opening is disengageable by means of a separate release button.

In another aspect of the invention, a pressure indicator is provided that includes a transparent elongated cylinder viewable by the user of the transfer device and housing a piston which is slidingly received within the cylinder. The cylinder includes an inlet port through which pressurized fluid can enter, and the piston is biased so that the relative position of the piston and the cylinder provides a visual indication of the relative fluid pressure in the transfer device. The pressure indicator can include a portion having a inside diameter greater than that portion of the cylinder in which the piston is disposed and an outlet port in communication with the enlarged-diameter portion of the cylinder. Consequently, when the fluid pressure is sufficient to move the piston into the enlarged-diameter portion of the cylinder, fluid escapes passed the piston and exits the cylinder through the exit port. Alternatively, the pressure indicator can be connected and parallel fluid communication with a separate pressure relief valve of known construction.

In another aspect of the invention, the catheter includes a connector at its proximal end that is received in a central opening in the transfer device. The connector includes at least one detent for securing the connector in the central opening of the transfer device, the detent having to be manually actuable to release the catheter from the transfer device.

In a further aspect of the invention, a method is provided for determining whether the treating elements reside in the transfer device. The method includes encapsulating the treating elements in a material having a known wavelength/reflection ratios; shining to lights of different wavelengths into the area in the transfer device where the treating elements normally reside before and after being introduced into the catheter; measuring the reflectivety of the two lights as reflected off the area in the transfer device; determining the wavelength/reflection ratios of the reflected light; comparing the measured wavelength/reflection ratios with the known wavelength/reflection ratios; and indicating whether the measured ratios are substantially the same as the known ratios.

A system for accomplishing the method described above is another aspect of the invention and includes a power source; a first light source optically connected to the targeted location in the transfer device and that emits a light having a first wavelength; a second light source optically connected to the targeted location that emits light having a second wavelength; a photosensor optically connected to the targeted location that measures the light reflected off the targeted location and creating a signal corresponding thereto; a window detector for determining whether the signal created by photosensor is within a predetermined band corresponding to a signal which would be created by light of first and second wavelengths being reflected off the element; and an indicator light that is activated if the signal created by the photosensor is within the predetermined band.

DRAWINGS

FIG. 2a is a cross-sectional view of the assembled transfer device of FIG. 2.

FIG. 4 is a bottom view of the rear housing of the transfer device.

FIG. 5 is a perspective view of the fluid control handle.

FIG. 7 is a bottom view of the fluid control switch.

FIG. 9 is an enlarged sectional view of the portion of the rear housing of the transfer device that interfaces with the seed lumen of the quartz sleeve.

Figure 19:
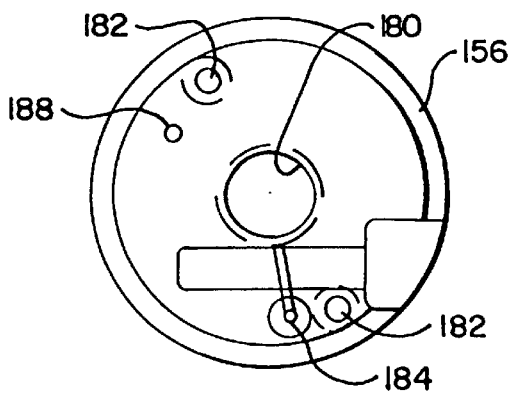
FIG. 19 is a plan view of the proximal face of the front housing.
Figure 19A:
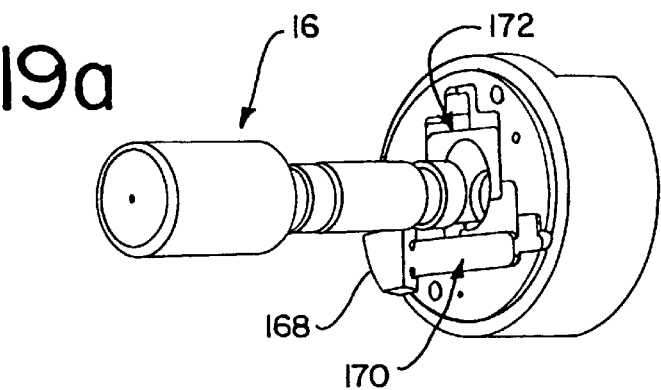

FIGS. 19a,b,c illustrate the interaction of the release trigger and release switch during the insertion of the connector into the trigger device.

Figure 20:
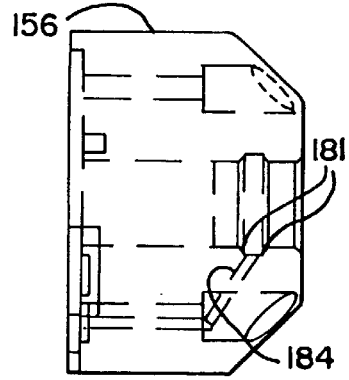

FIG. 20 is a side view of the front housing.

Figure 21A:
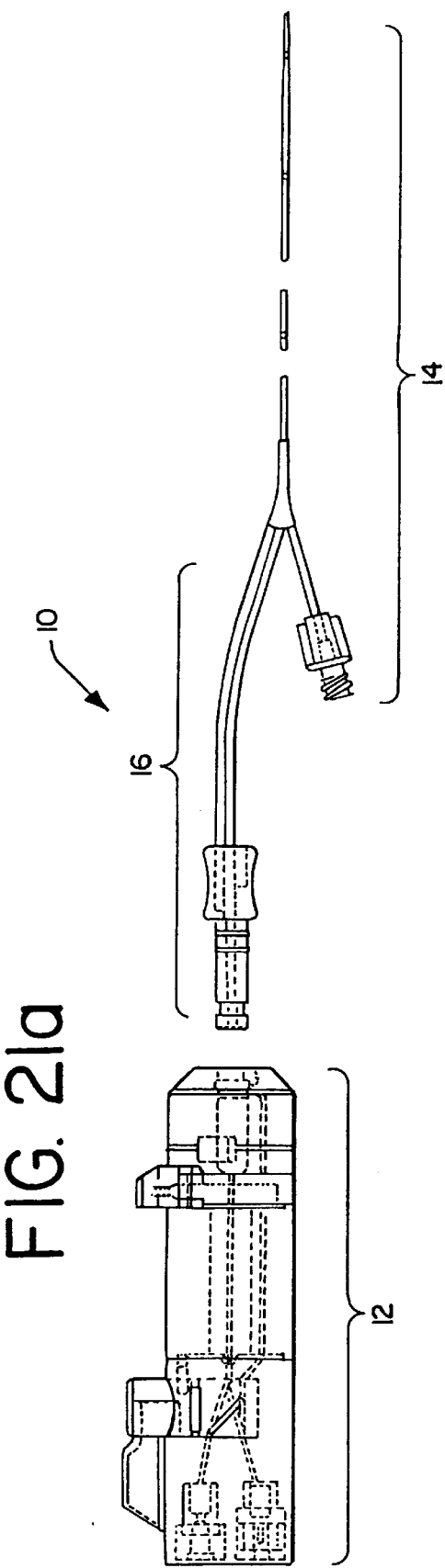

FIG. 21a is a schematic drawing of an intraluminal radiation system embodying the present invention with an alternate construction for the rear housing of the transfer device.

Figure 21C:
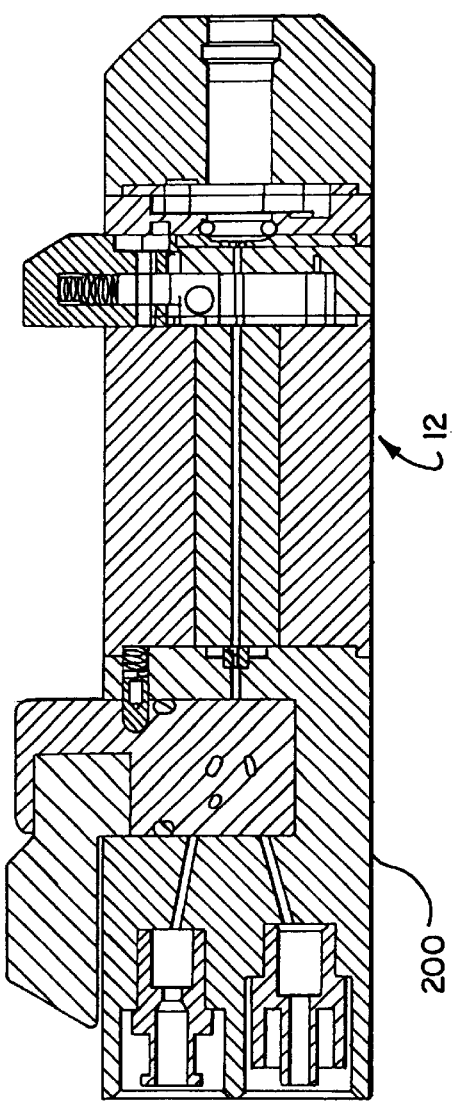
Figure 21B:
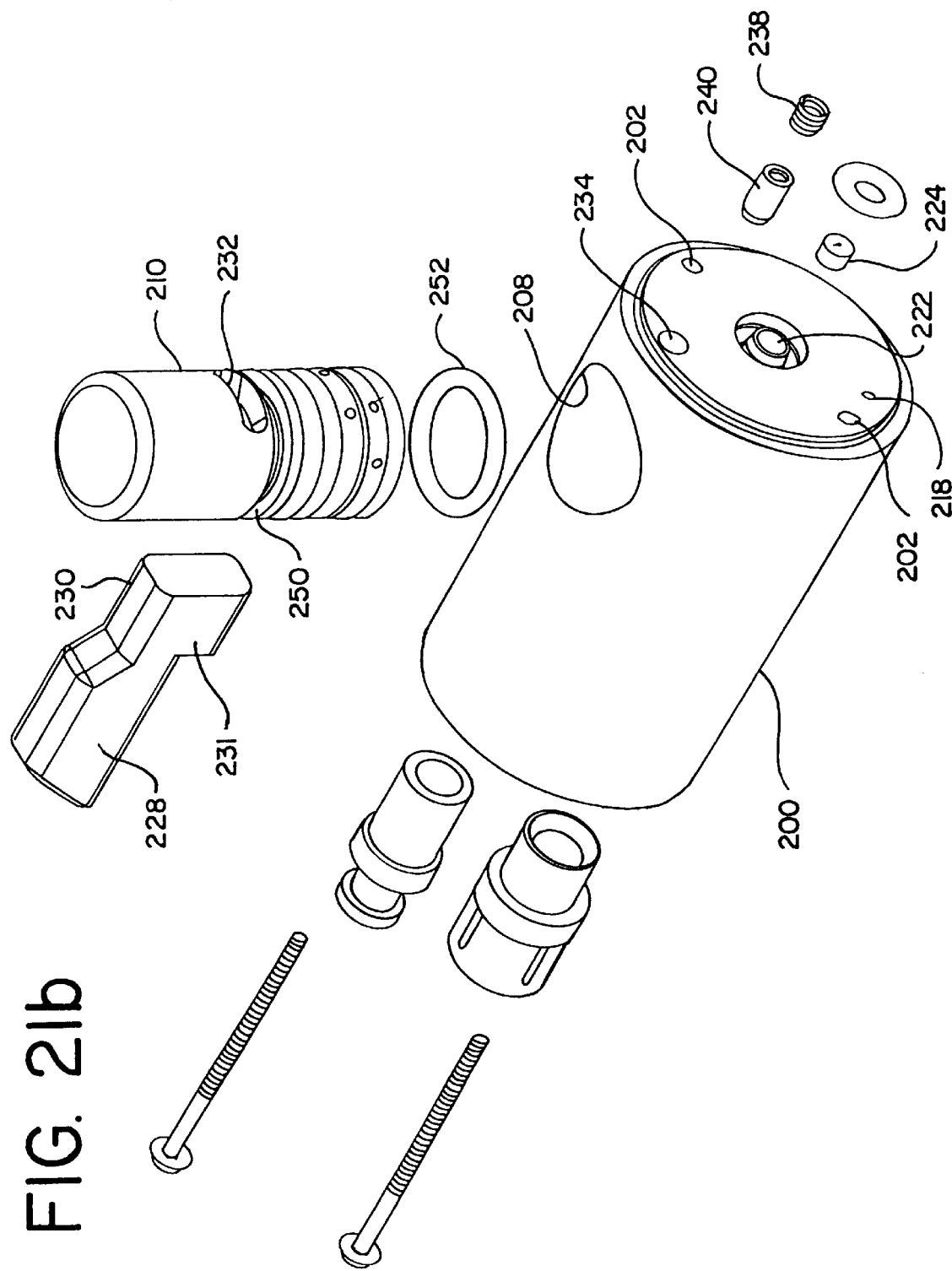

FIG. 21b is an exploded perspective view of the rear housing/fluid control switch of FIG. 21a.

FIG. 21c is a cross-sectional view of the assembled transfer device with the alternate embodiment of the rear housing/fluid control switch of FIG. 21b.

Figure 22:
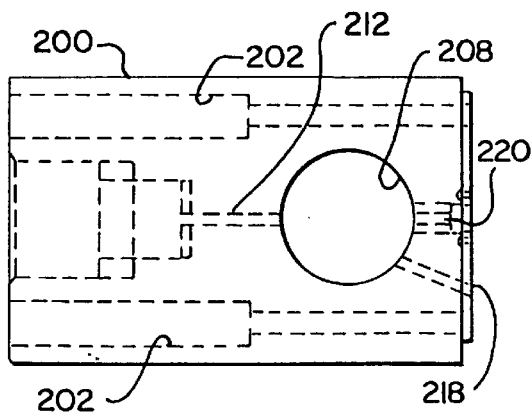

FIG. 22 is a top view of the rear housing of FIG. 21b.

Figure 23:
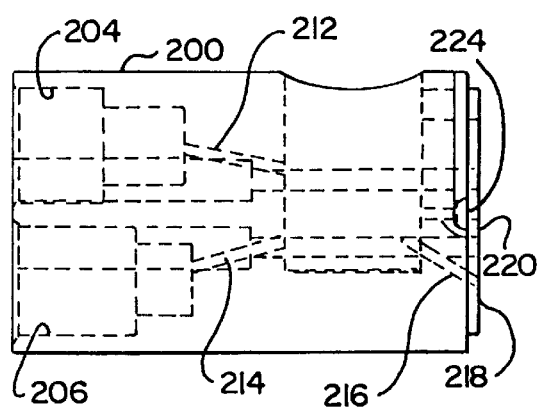

FIG. 23 is a side view of the rear housing of FIG. 21b.

Figure 24:
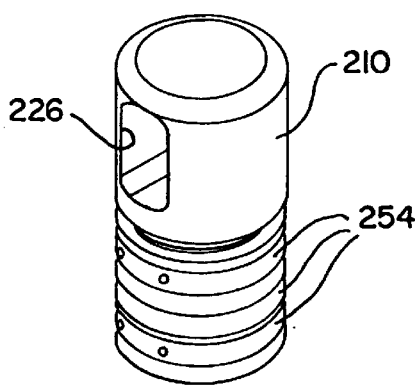

FIG. 24 is a perspective view of the fluid control switch of FIG. 21b showing the proximal side of the switch.

Figure 25:
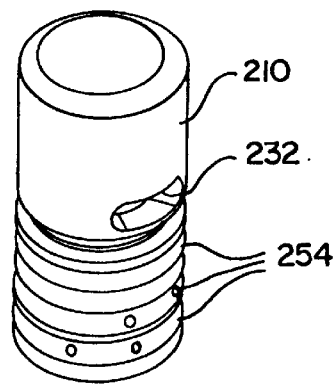

FIG. 25 is a perspective view of the fluid control switch of FIG. 21b showing the distal side of the switch.

Figure 26:
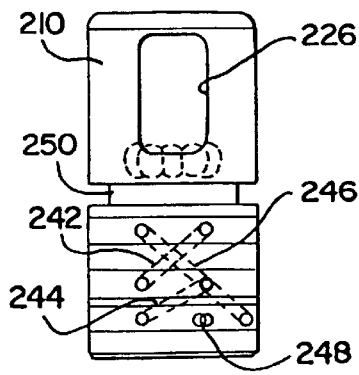

FIG. 26 is a plan view of the fluid control switch of FIG. 21b showing the proximal side of the switch.

Figure 27:
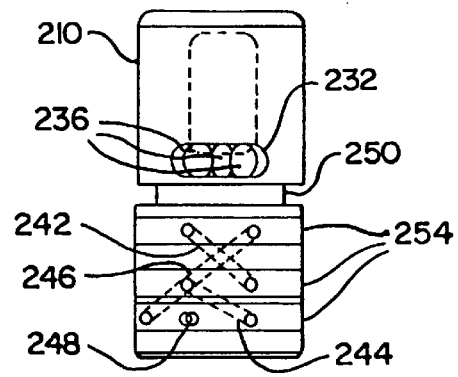

FIG. 27 is a plan view of the fluid control switch of FIG. 21b showing the distal side of the switch.

Figure 28:
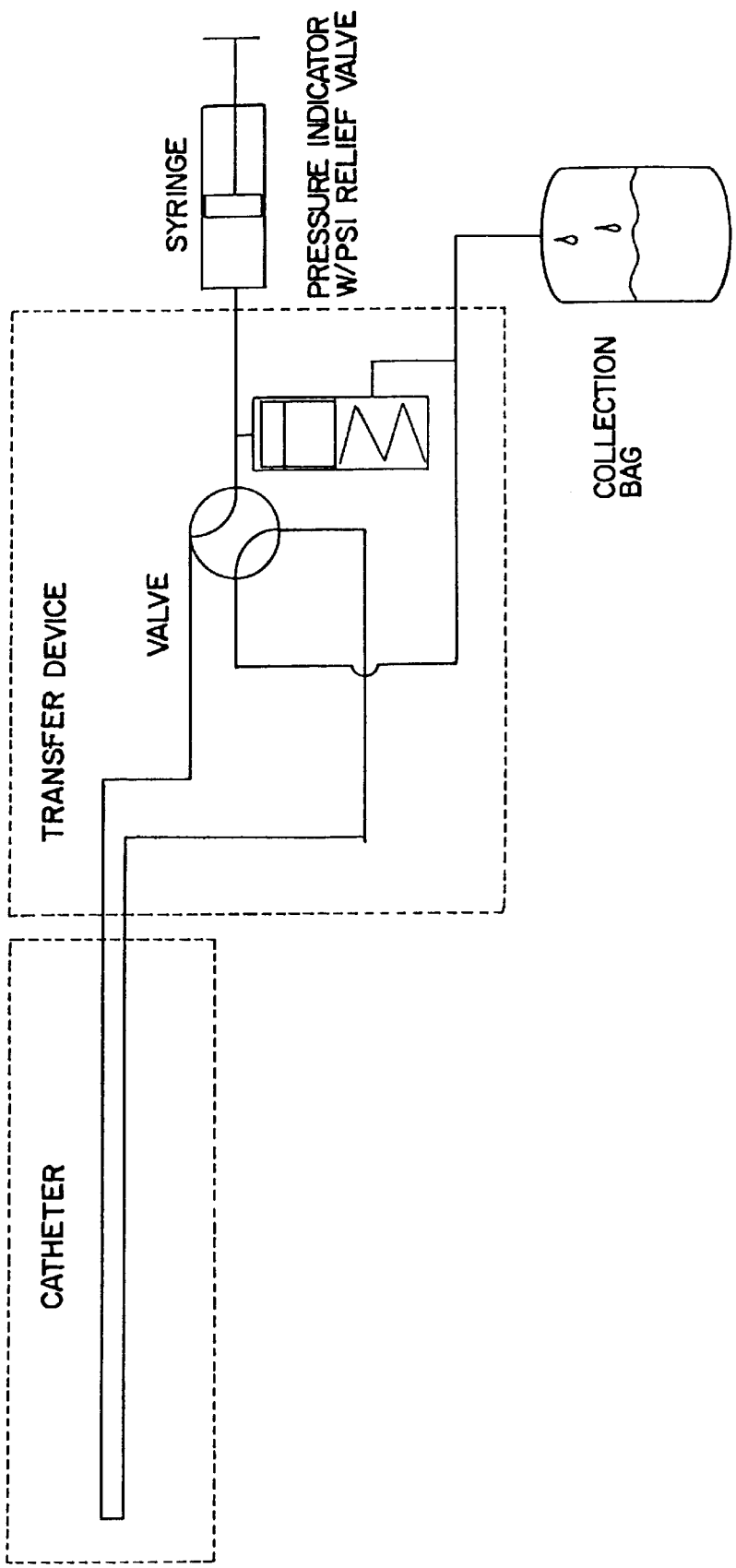

FIG. 28 is a schematic view of the intraluminal radiation treatment system of the present invention.

FIG. 29A is perspective view of a further embodiment of the transfer device of the present invention also showing a syringe attached thereto.

FIG. 29B is a perspective view similar to FIG. 29A, except for the top half of the housing of the transfer device is removed to show its interior construction.

Figure 30:
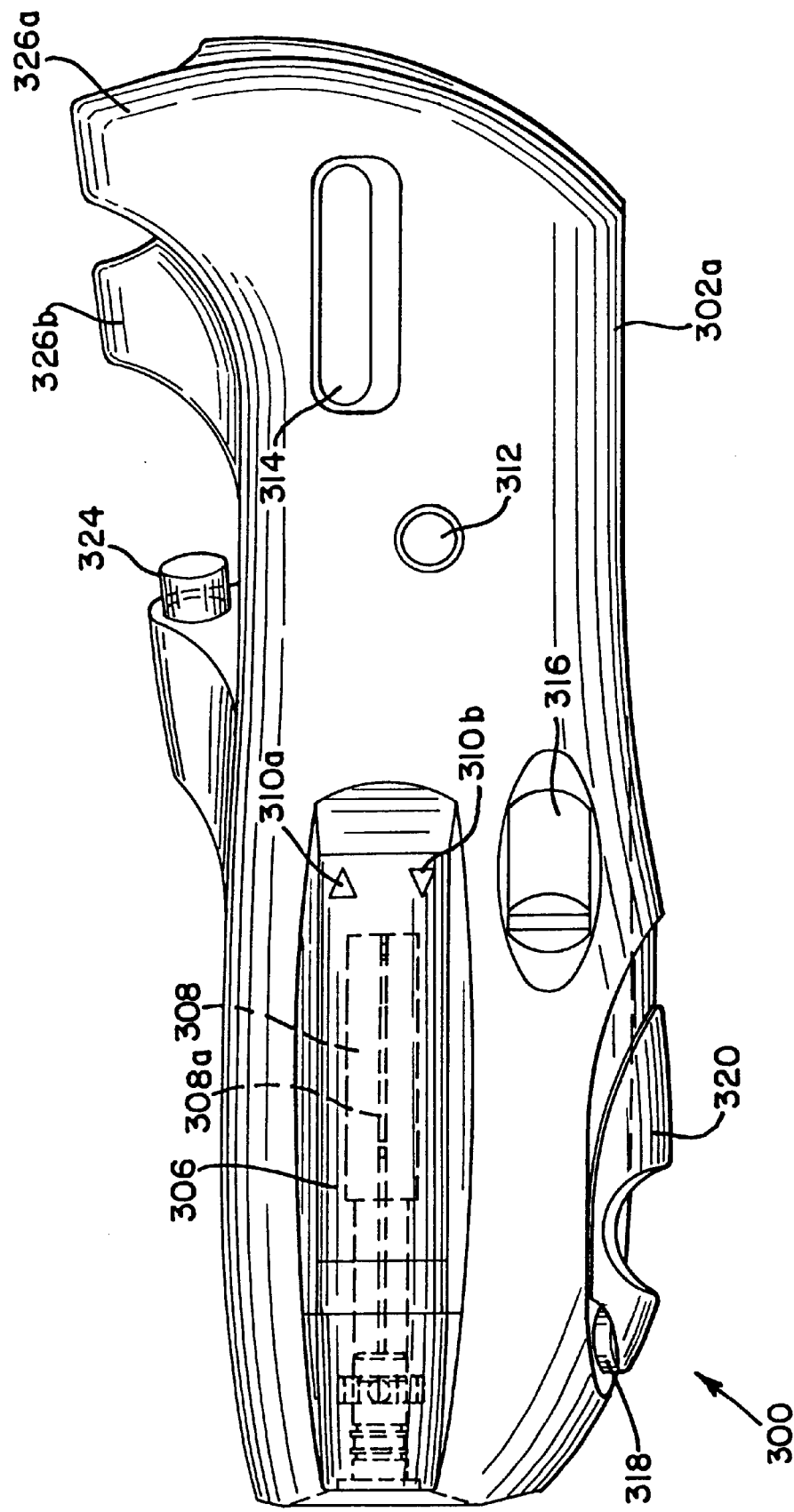

FIG. 30 is a plan view of the housing of the transfer device of FIG. 29A.

FIG. 31 is an exploded perspective view of the transfer device of FIG. 29A.

FIG. 32A is a lateral cross-sectional view of the transfer device of FIG. 29A.

FIG. 32B is a longitudinal cross-sectional view of the transfer device of FIG. 29A.

FIG. 32C is an enlarged cross-sectional view of one of the internal components of the transfer device of FIG. 29A.

FIG. 32D is a longitudinal cross-sectional view of the transfer device of FIG. 29A perpendicular to the crosssectional view shown in FIG. 32B.

Figure 33:
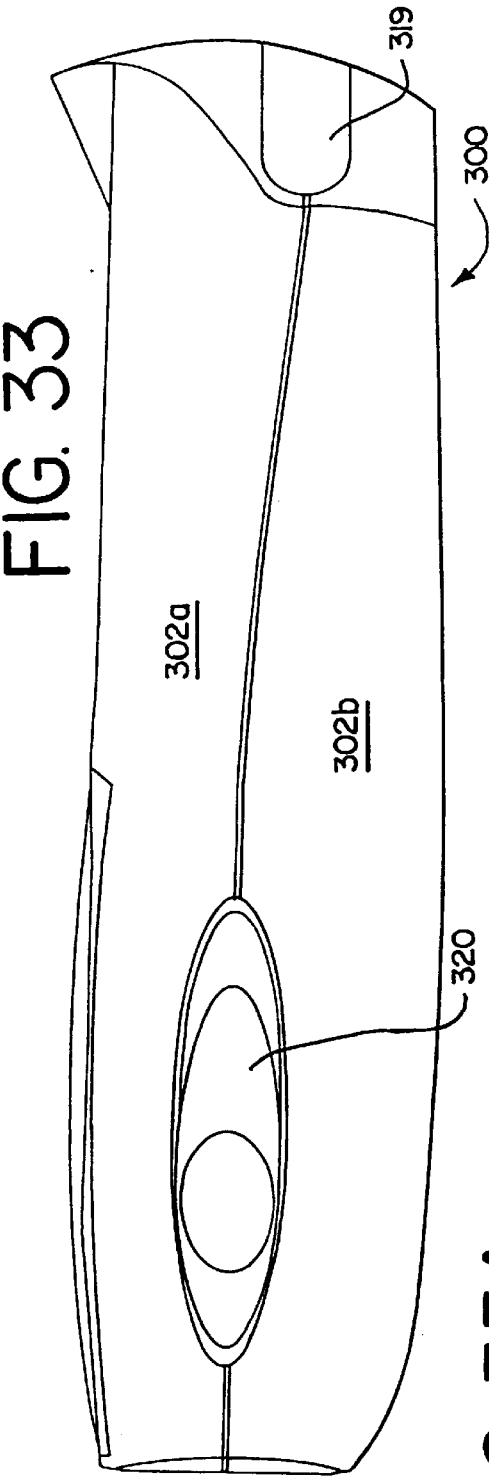

FIG. 33 is a side view of the transfer device of FIG. 30.

FIGS. 35A–D show a pressure indicator/pressure relief valve, and its component parts, that can be advantageously used in the transfer device of FIG. 29A.

Figure 37:
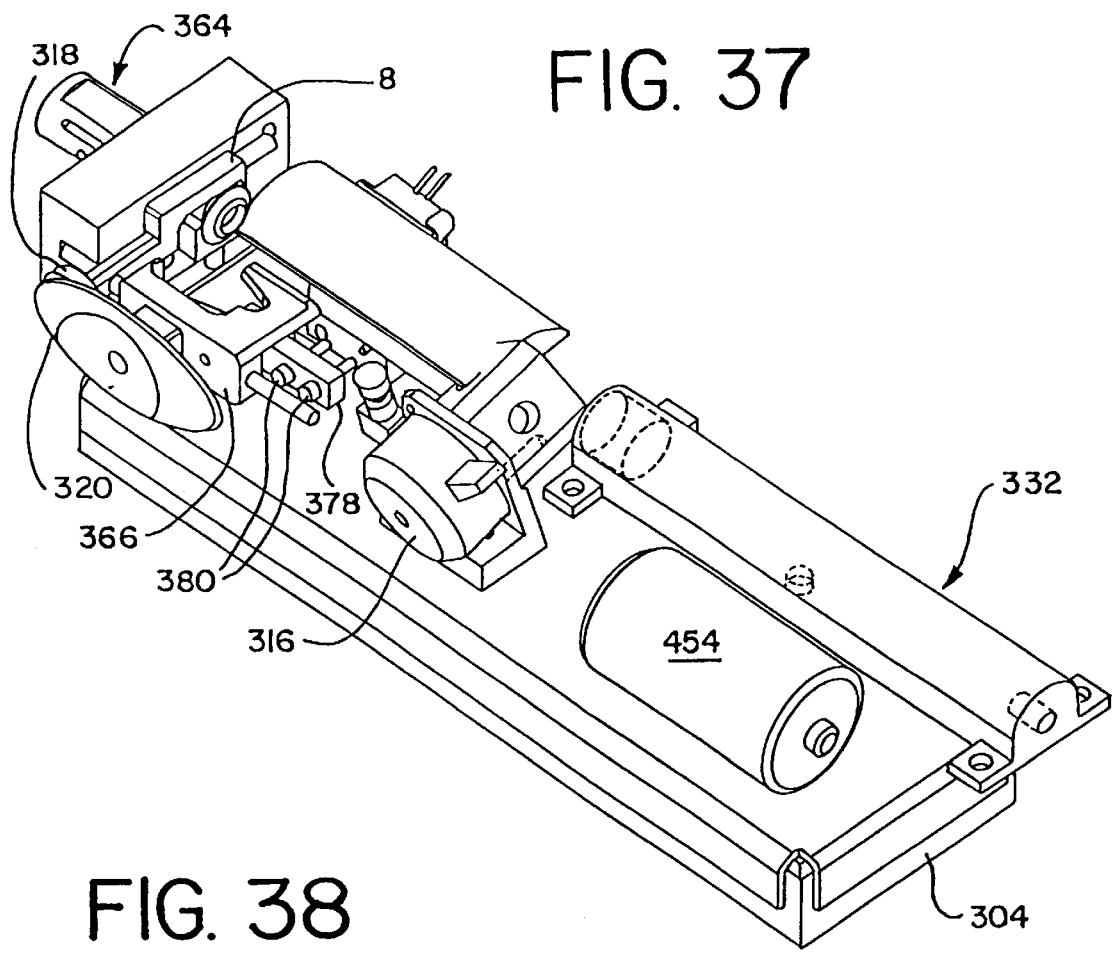

FIG. 37 is a perspective view of selected interior components of the transfer device of FIG. 29A mounted on a chassis.

Figure 38:
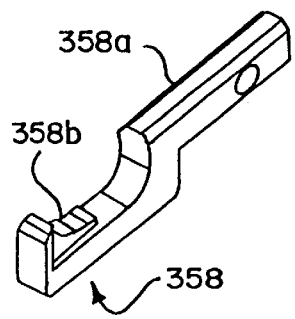

FIG. 38 is a perspective view of a release switch for use in the transfer device of FIG. 29A.

Figure 39A:
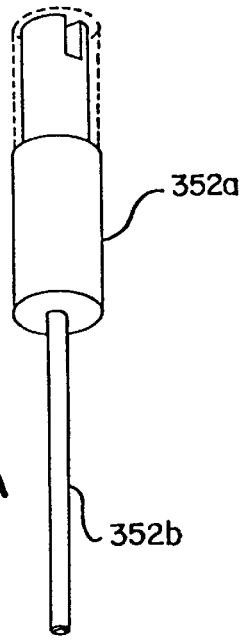
Figure 39B:
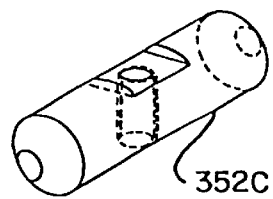

FIGS. 39A–B are the perspective views of the components for the pin gate for use in the transfer device of FIG. 29A.

Figure 40A:
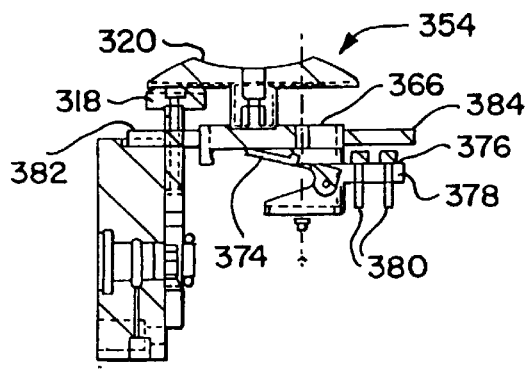

FIGS. 40A,B,C,D show the pin gate/release switch safety interlock used in,the transfer device of FIG. 29A.

Figure 41B:
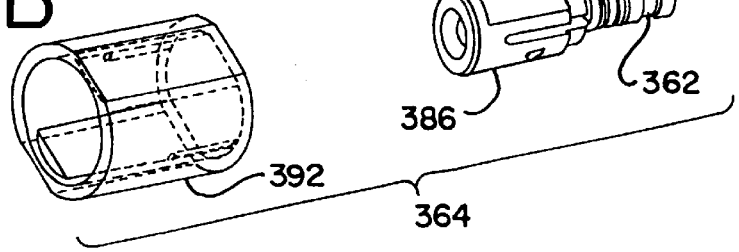
Figure 41A:
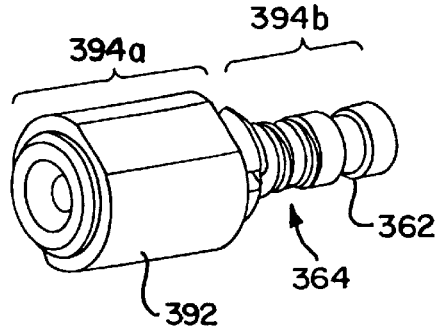

FIGS. 41A,B,C,D,E show the catheter connector and its various subparts used in the present invention.

FIGS. 42A,B,C,D show a catheter and its cross-section (FIG. 42D) for use in the present invention.

Figure 45:
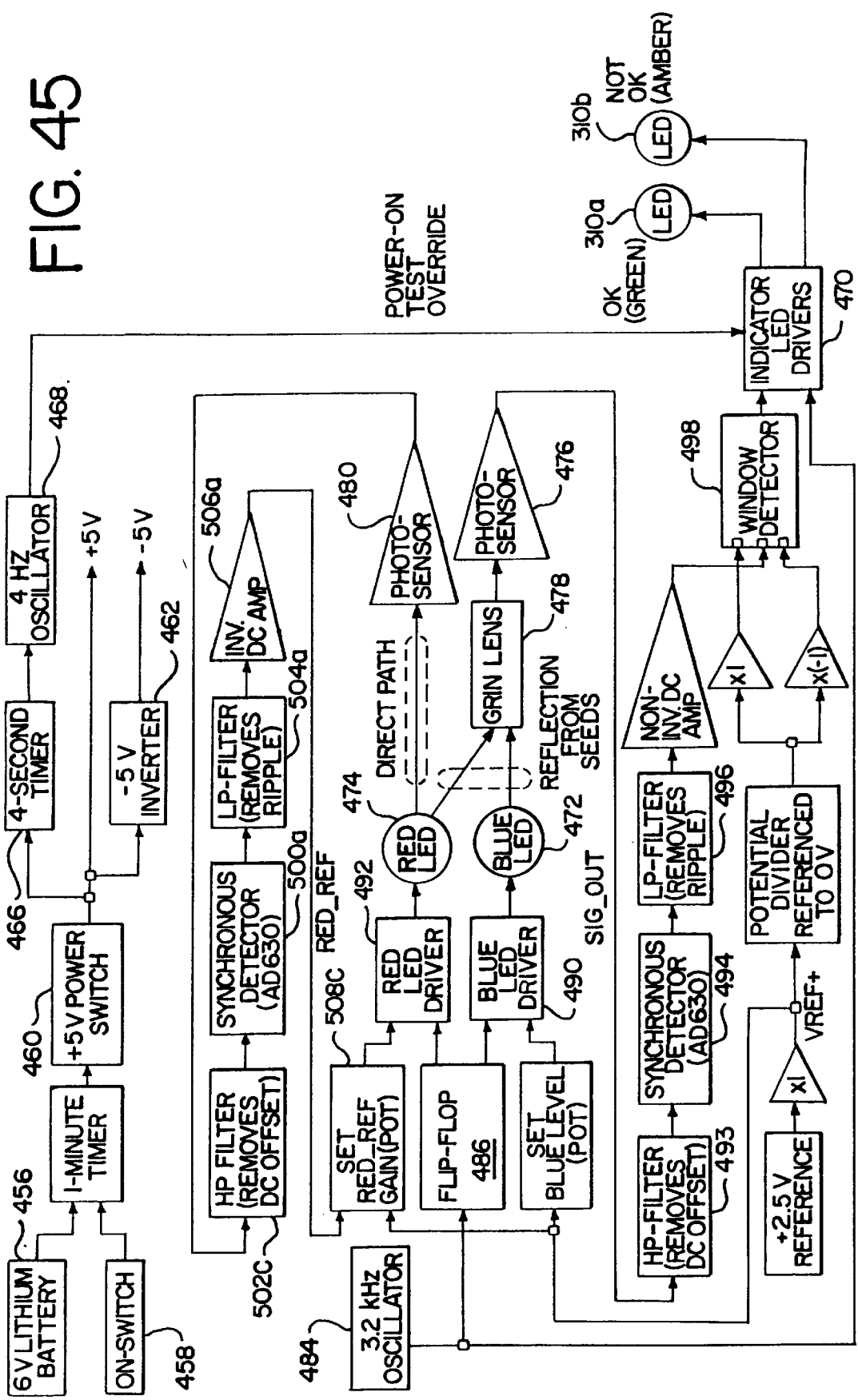

FIGS. 45 is a logic diagram for a treating element verification system advantageously used with the transfer device of FIG. 29A.

Figures 1, 46A:
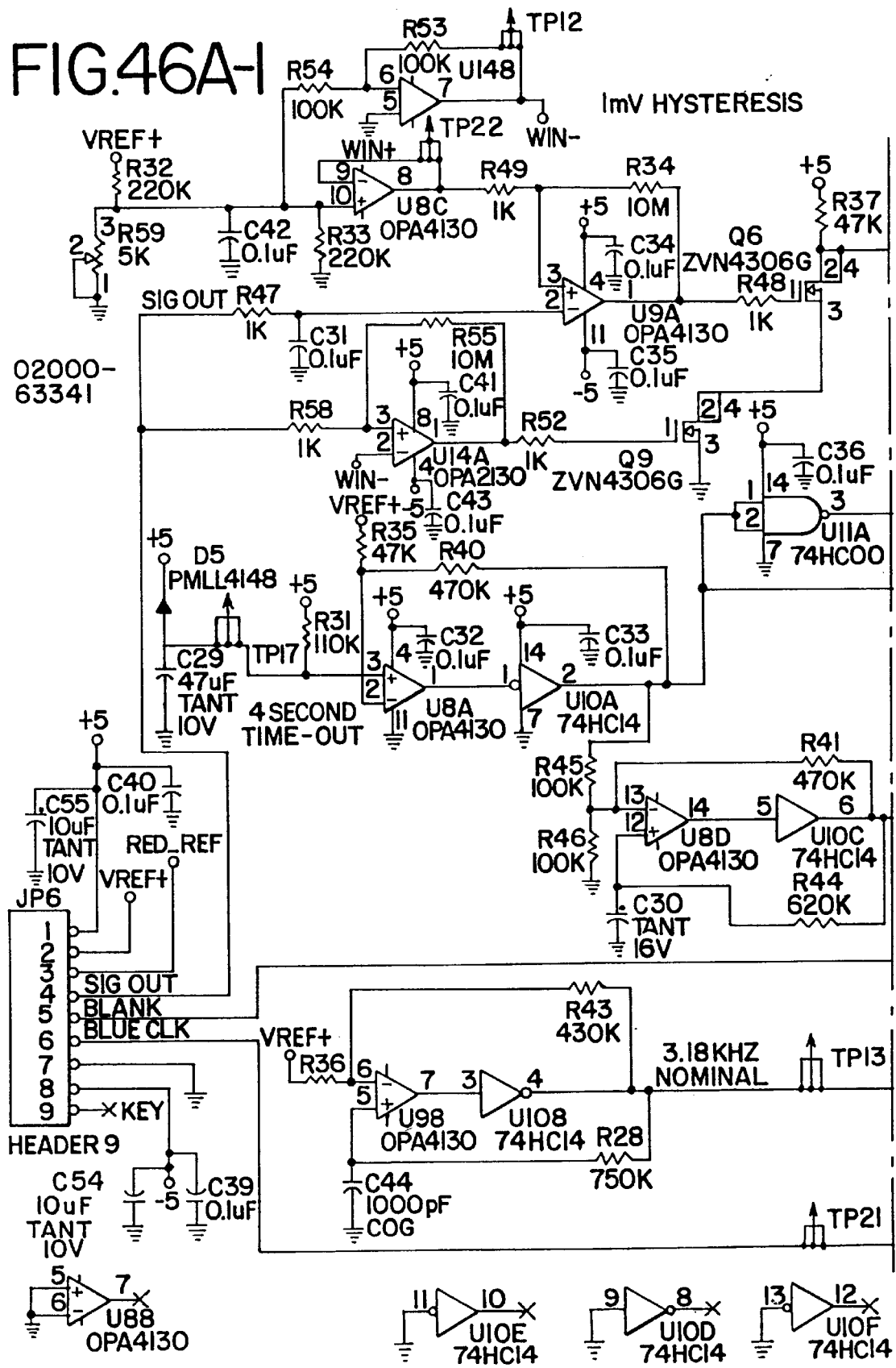
FIG. 1 is a schematic drawing of intraluminal radiation system comprising a transfer device, a delivery catheter, and a connector for connecting the two.
Figures 2, 46A:
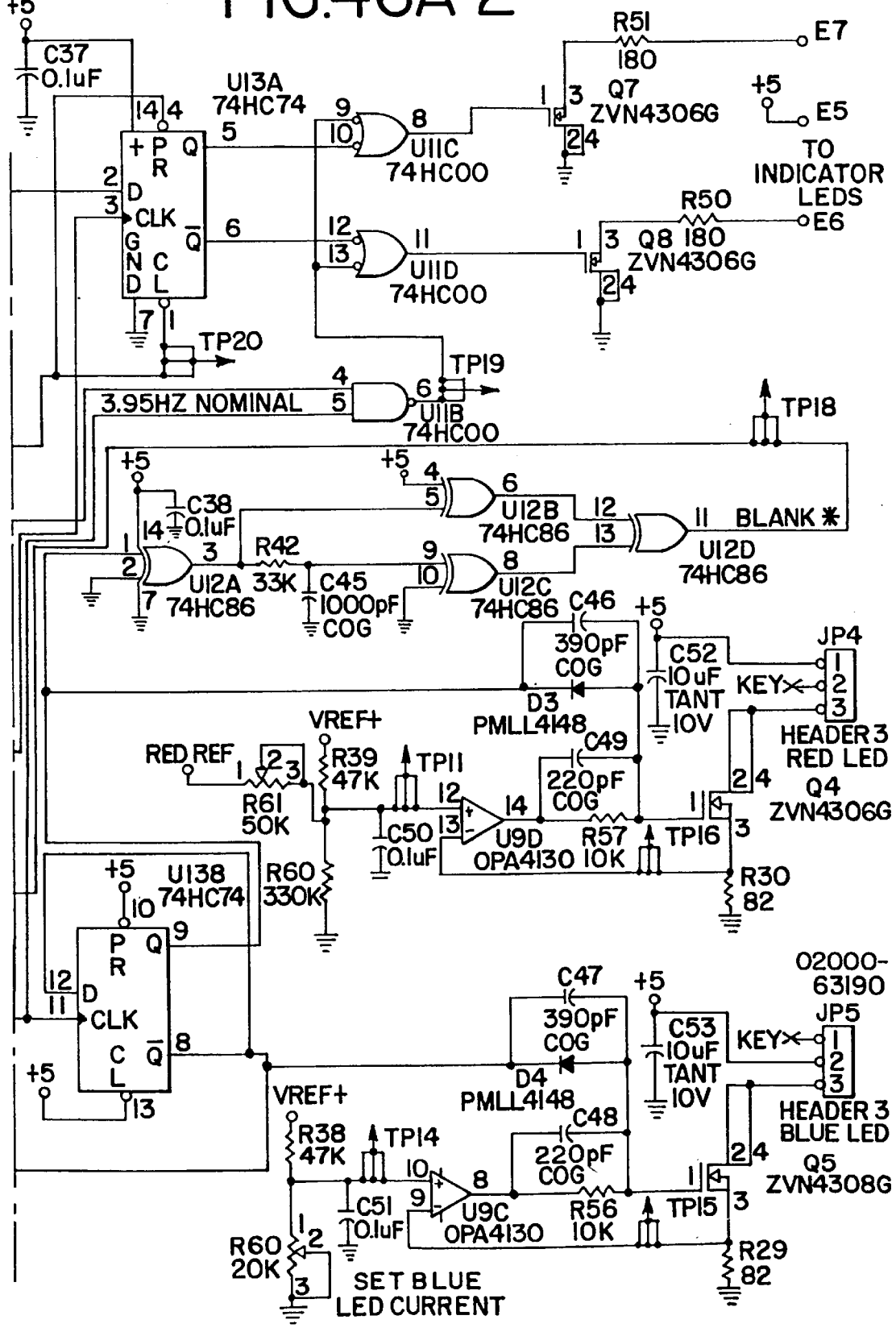
FIG. 2 is an exploded view of the transfer device of the present invention.

FIGS. 46A-1, 46A-2; 46B; and 46C-1, 46C-2, 46C-3 are circuit diagrams for performing the functions set forth in the logic diagram of FIG. 45.

Figure 47:
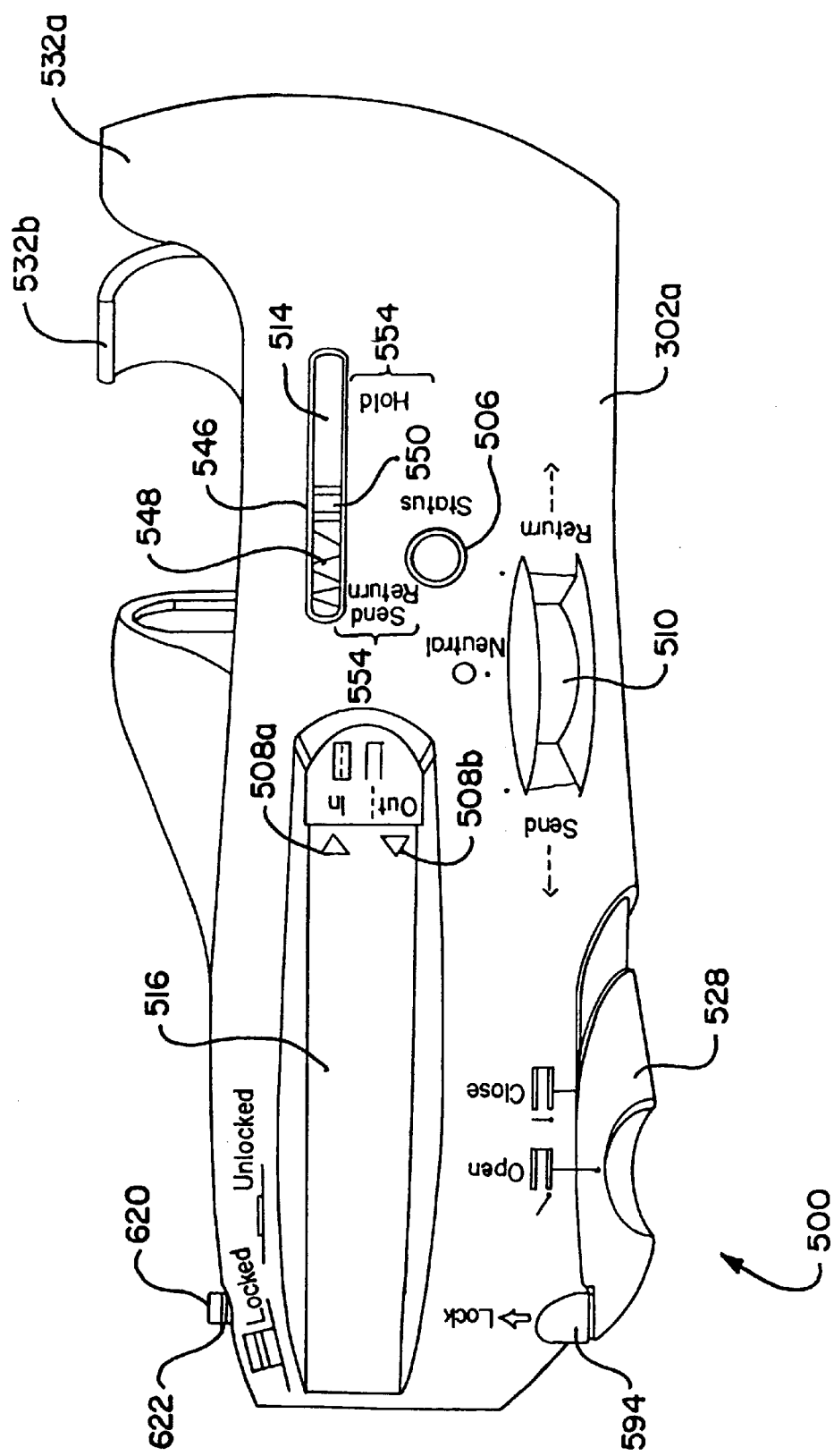

FIG. 47 is a plan view of the housing of a further embodiment of the transfer device.

Figure 48:
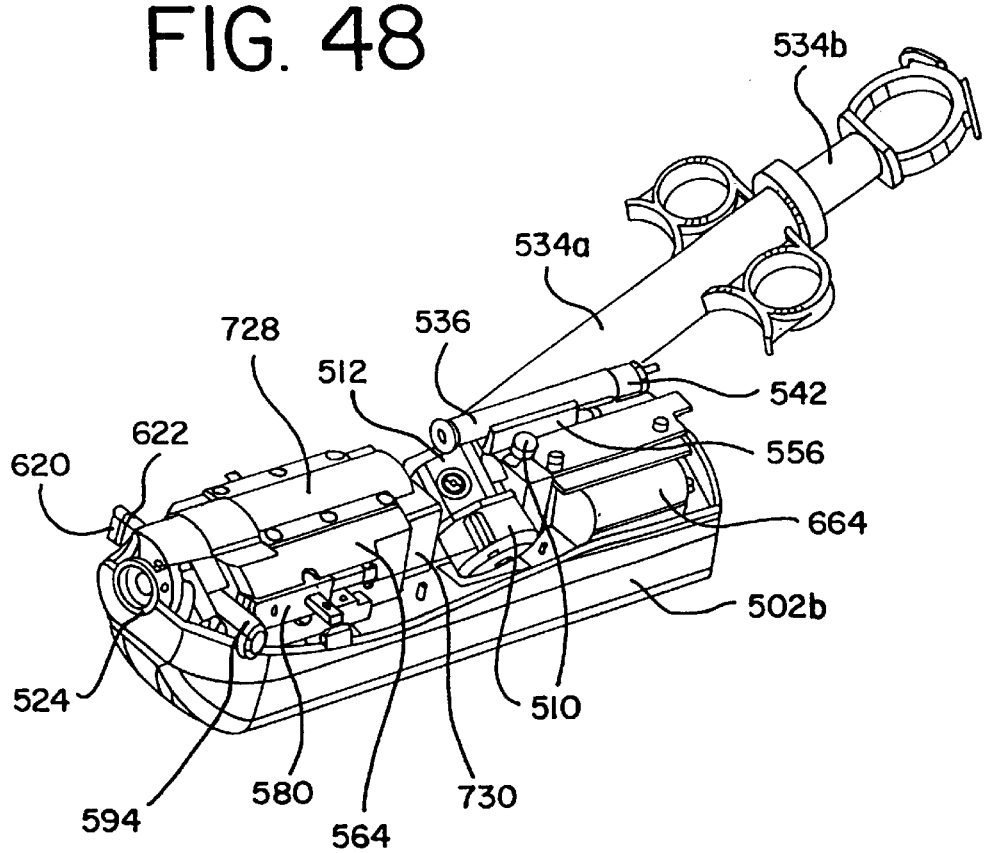

FIG. 48 is a perspective view of the transfer device of FIG. 47 with the top half of the housing removed to show interior detail.

Figure 49:
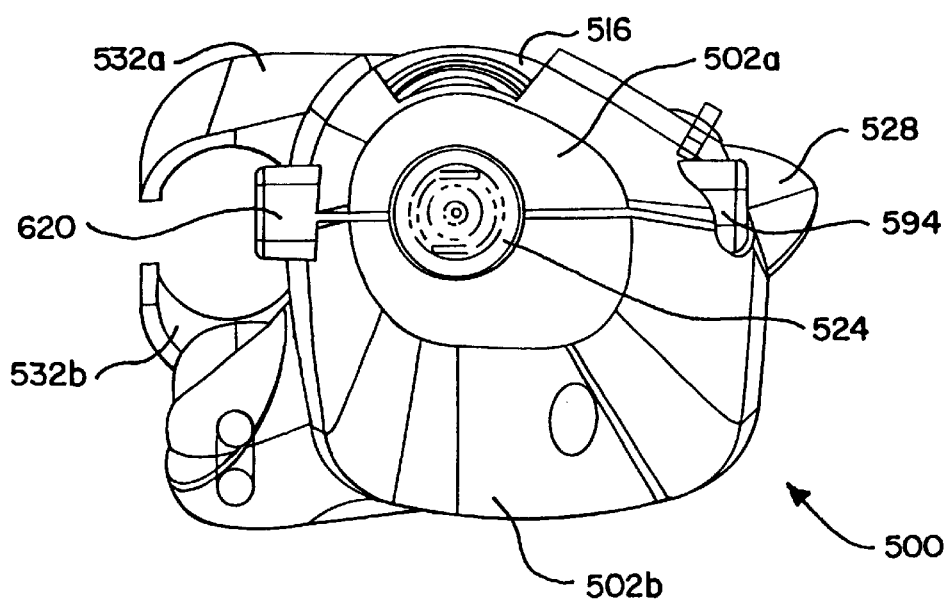

FIG. 49 is an end view of the transfer device of FIG. 47 looking at the distal end.

FIG. 50 is an exploded perspective view of the transfer device of FIG. 47.

FIGS. 51A and B are longitudinal cross-sectional views of the transfer device of FIG. 47.

FIG. 51C is a lateral cross-sectional view of the transfer device of FIG. 47.

FIG. 52 is an exploded perspective view of the pressure indicator gauge and pressure relief valve for use in conjunction with the transfer device of FIG. 47.

FIG. 53 is a cross-sectional view of the pressure indicator gauge and pressure relief valve of FIG. 52, with the fluid flow therethrough shown schematically.

Figure 54A:
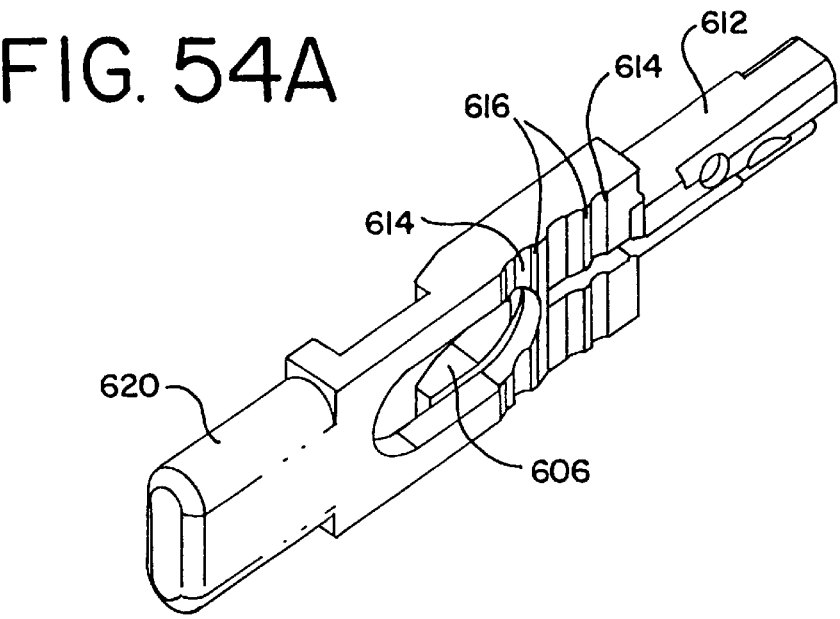

FIGS. 54A and B are perspective views of the latch body for use in connection with the transfer device of FIG. 47.

Figure 55:
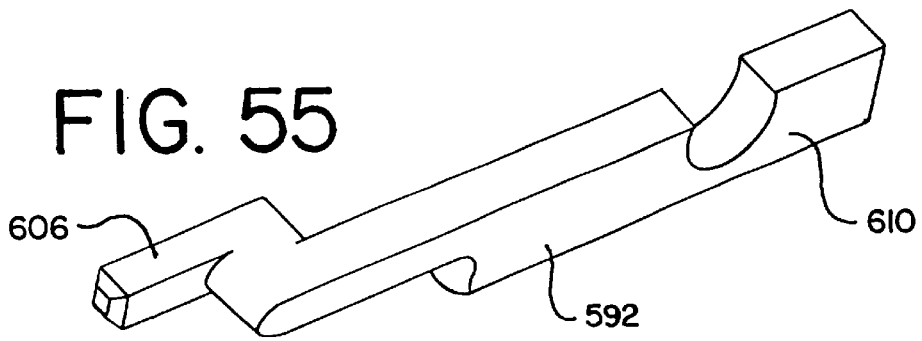

FIG. 55 is a perspective view of the latch sear for use in conjunction with the transfer device of FIG. 47.

Figure 56A:
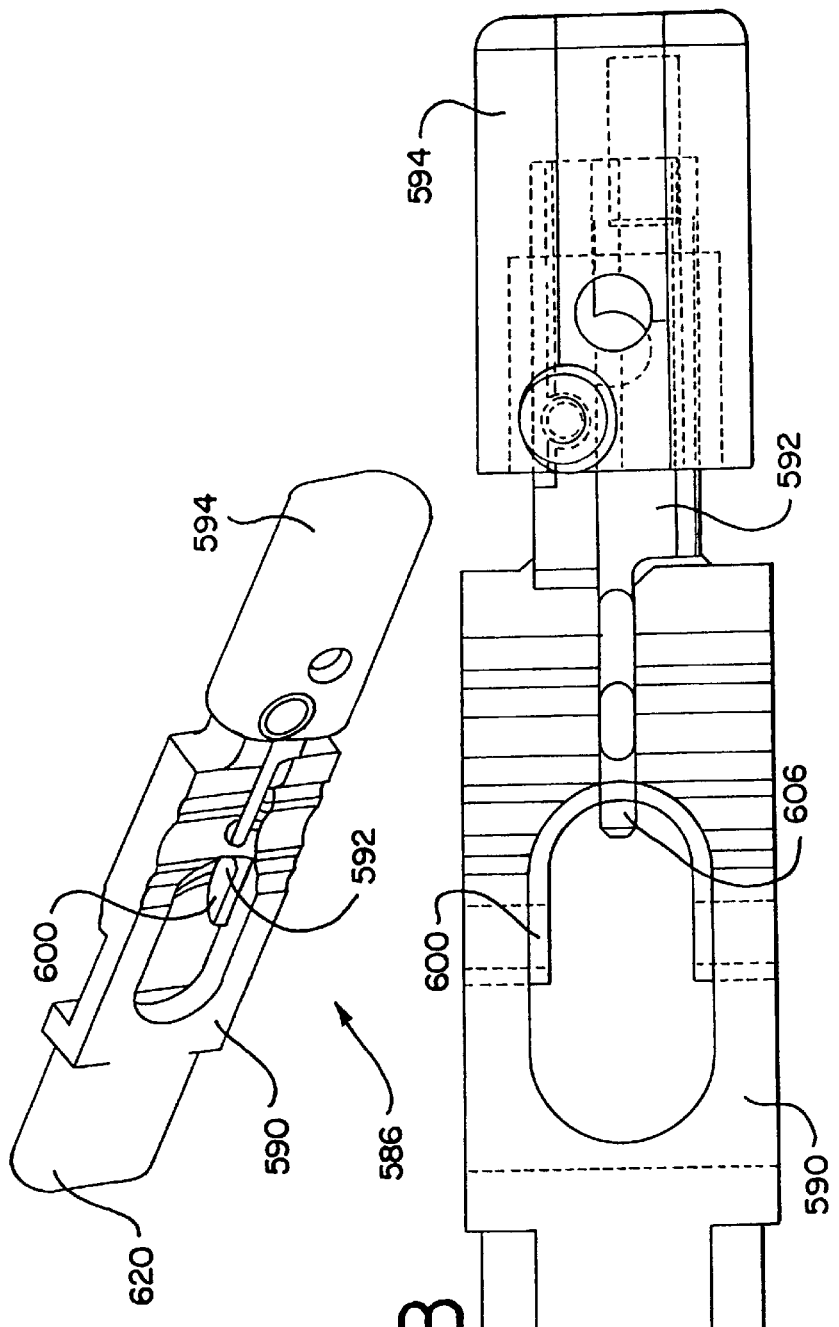

FIGS. 56A, B and C show the assembled latch mechanism, including the latch body, latch sear, and latch button in perspective, plan, and cross-sectional views, respectively.

FIGS. 57A and B show the skirt connector for use in conjunction with the catheter connector in perspective and cross-sectional views, respectively.

FIG. 57C is a cross-sectional view of the proximal end of the catheter connector showing the central plug.

FIG. 58A is a plan view of a catheter for use in the present invention.

FIG. 58B is an enlarged lateral cross-sectional view of the catheter of FIG. 58A.

FIG. 58C is an enlarged longitudinal cross-sectional view of the distal end of the catheter of FIG. 58A.

FIG. 59 is a plan view of a treatment element seed train for use in the present invention.

Figure 60:
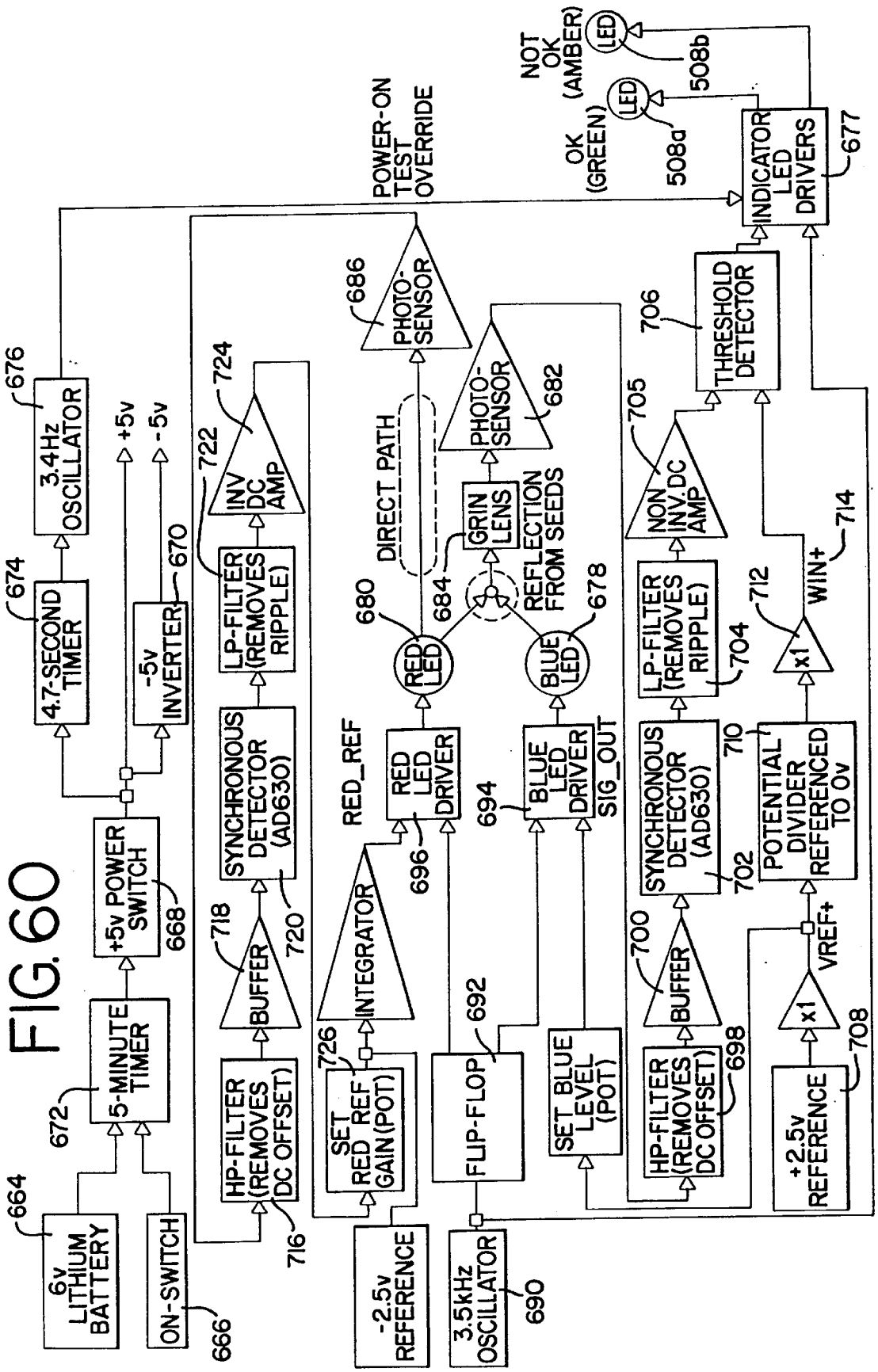

FIG. 60 is a logic diagram for the treating element verification system for use with the transfer device of FIG. 47.

FIGS. 61A-1, 61A-2, 61A-3; 61B; and 61C-1, 61C-2 are circuit diagrams for performing the functions set forth in the logic diagram of FIG. 60.

Figures 1, 61A:
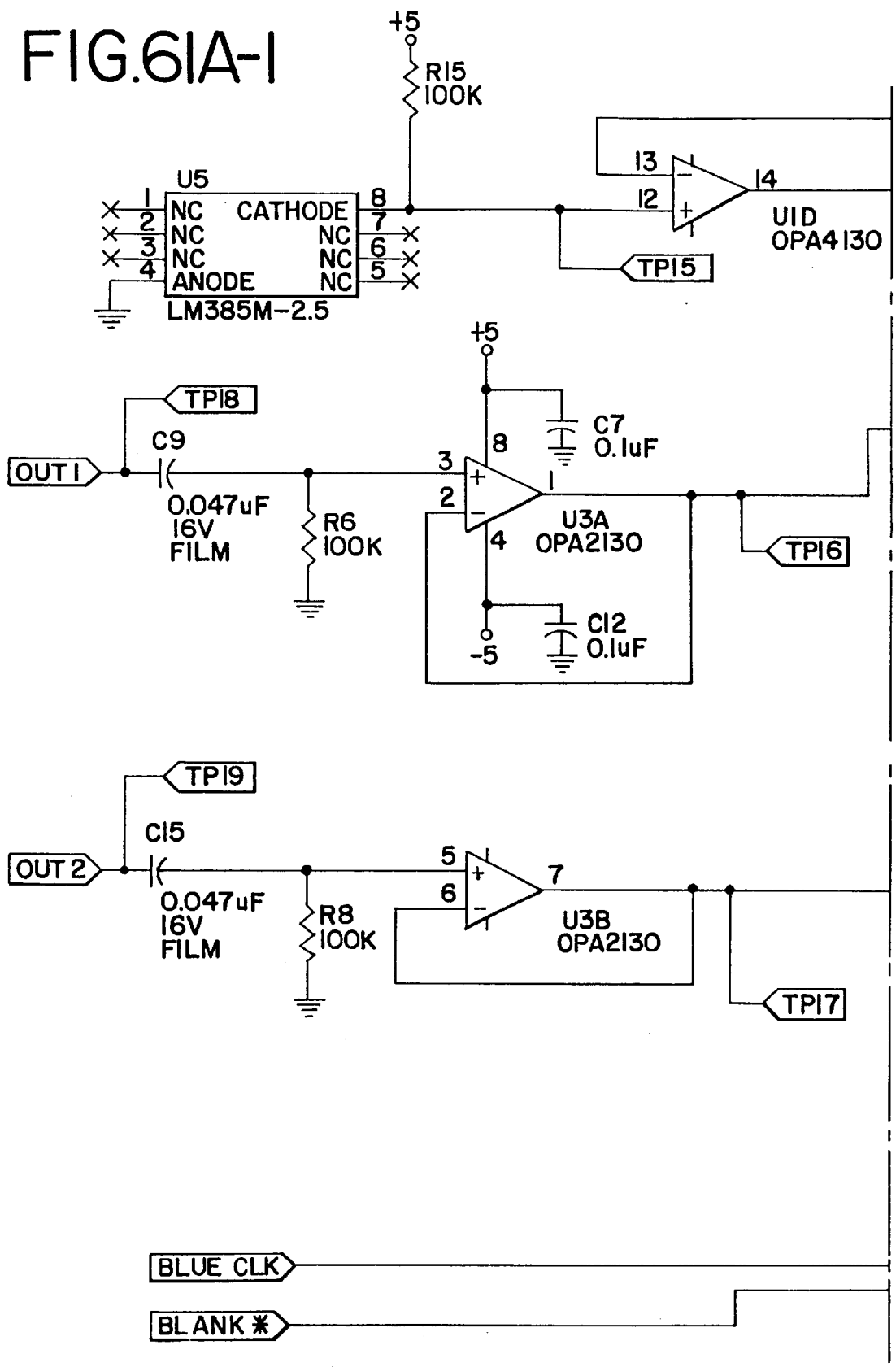

FIG. 61D is a schematic diagram for a distribution board for the treating element verification system of FIGS. 60 and 61A–C.

Figure 62A:
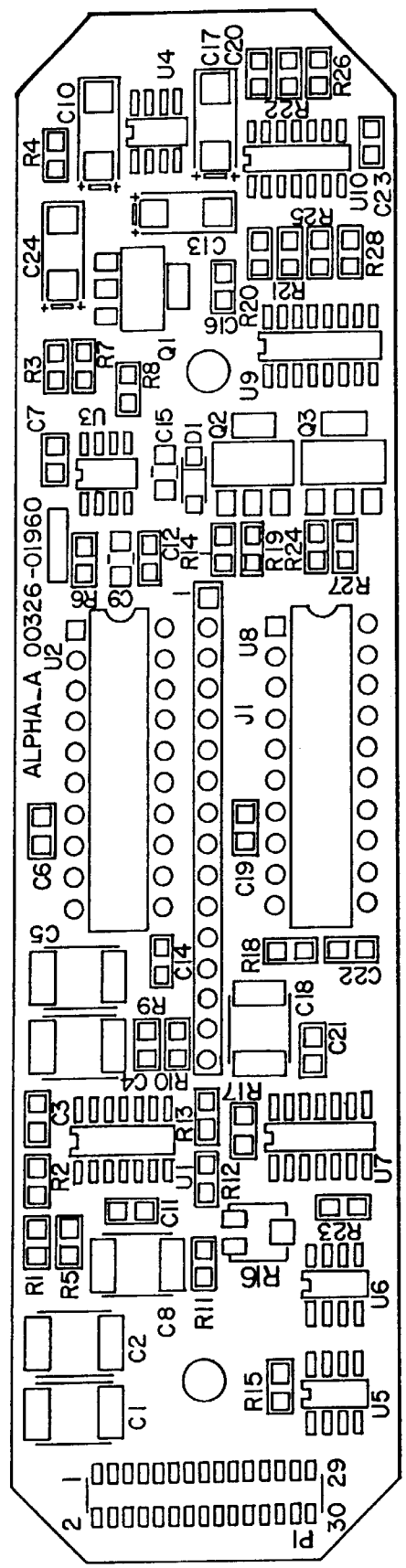

FIGS. 62A,B,C are printed circuit boards showing the mechanical outline for use with the treating element verification system of FIGS. 60 and 61A–D.

FIG. 63A is a schematic diagram showing the electrical connections between the various parts of the treating element verification system.

Figure 63B:
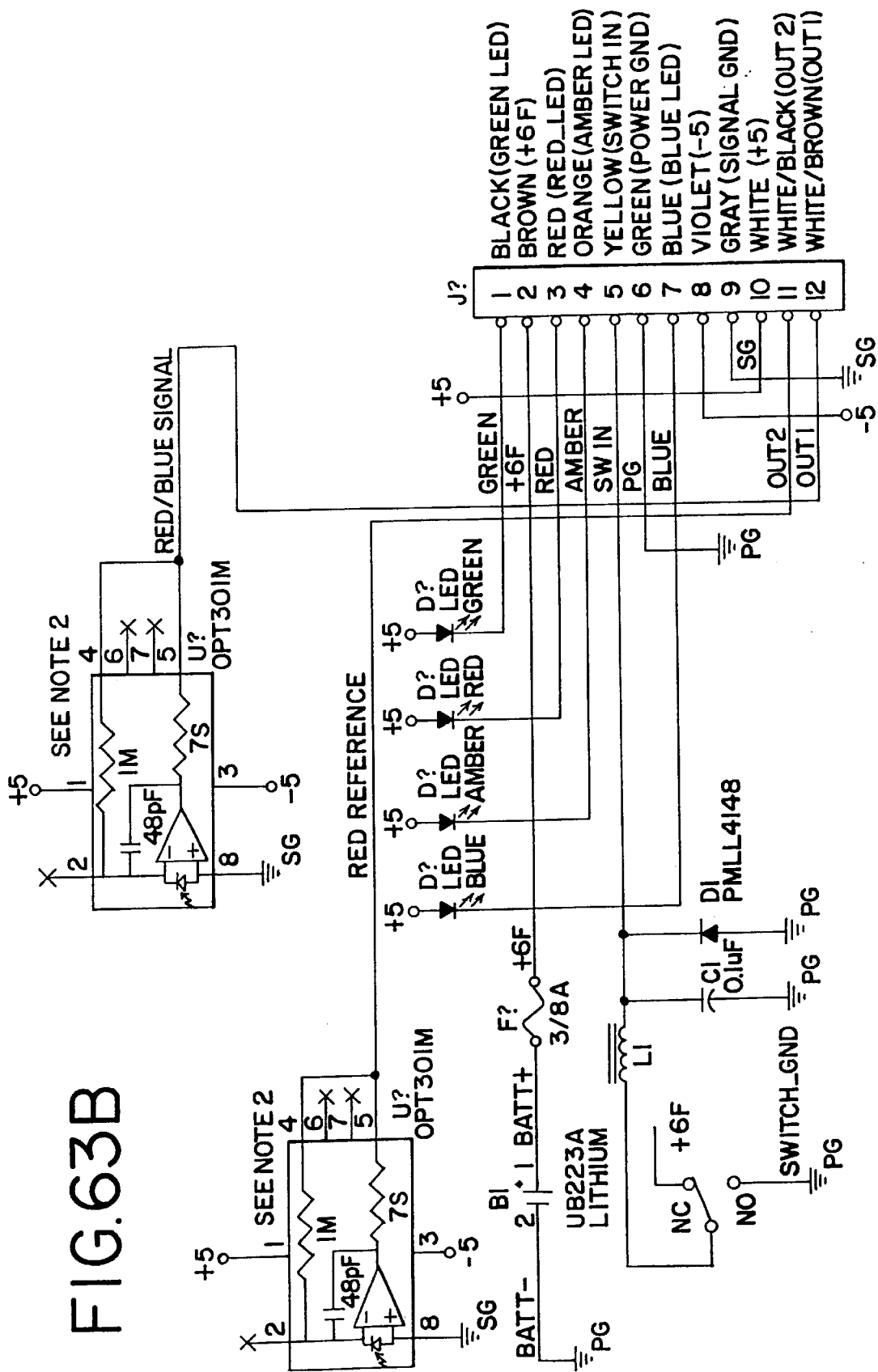

FIG. 63B is a circuit diagram for an equivalent circuit to FIG. 63A.

DETAILED DESCRIPTION

Turning to the figures of the drawings, FIG. 1 illustrates an intraluminal radiation system 10 according the present invention comprising a transfer device, generally indicated by 12, a delivery catheter, generally indicated by 14, and a connector, generally indicated by 16, for securely attaching the delivery catheter 14 to the transfer device 12. The delivery catheter 14 and connector 16 are substantially as described in the above-identified co-pending application which has been incorporated herein by reference.

The transfer device 12 functions to house and shield a radiation source train (not shown), which may include non-radioactive marker seeds, and controls the direction of fluid flow for priming the transfer device 12 and catheter 14 and effecting delivery and retrieval of the individual radiation elements.

The transfer device 12 is shown in exploded view in FIG. 2 and consists of three main assemblies: rear housing and fluid control switch assembly 18, central housing and actuator switch/shuttle gate assembly 20, and front housing 22. The rear housing and fluid control switch assemblies and the central housing and actuator switch/shuttle gate assembly disclosed herein are interchangeable with the corresponding parts disclosed in the above-referenced co-pending application The rear housing 18 comprises a cylindrical member 24, preferably made of polycarbonate, that includes two axial through-lumens 26 for positioning two screws 28 that connect the rear housing 18 to the central housing 20. The threads of the screws 28 can directly engage the polycarbonate material of the central housing 80 or the internal threads of the lumens 26 can receive helical, coiled wire inserts which will be engaged by the threads of the screws 28. Alternatively, the lumens in the central housing 80 that receive the screws 28 can include internally threaded metal inserts (not shown) secured therein by, e.g., ultrasonic welding, so that the threads of the screws 28 engage the internal threads of the metal inserts, thus providing a more durable connection between the rear housing 18 and the central housing 80.

The cylindrical member 24 includes a cylindrical recess 30 for placement of a fluid control switch 44, which is discussed in greater detail below. The cylindrical member 24 includes two luer connectors or fittings 32, 34, preferably made of a polycarbonate and secured to the cylindrical member 24 by a UV-cure adhesive. The luer fittings 32, 34 may be either partially or completely recessed within the rear housing 18. Luer fitting 32 is received in recess 32a in the cylindrical member 24 and is in fluid communication with a fluid inlet channel 36 (best seen in FIG. 3). The luer fitting 32 connects to a liquid or gas-filled device (not shown) that is used for hydraulic or pneumatic delivery and retrieval of the radiation source train to and from the delivery catheter 14.

Figure 46B:
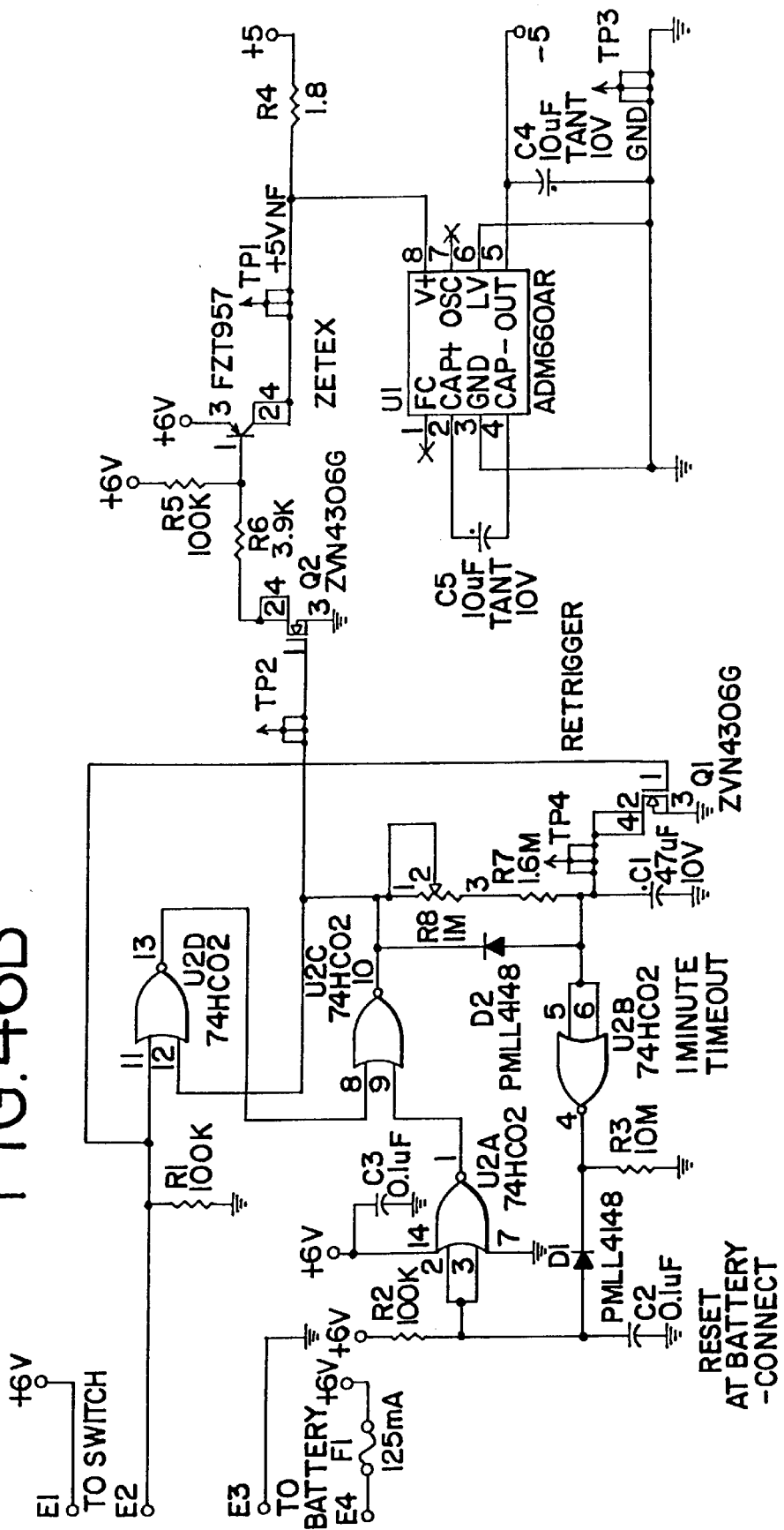
Figures 1, 46C:
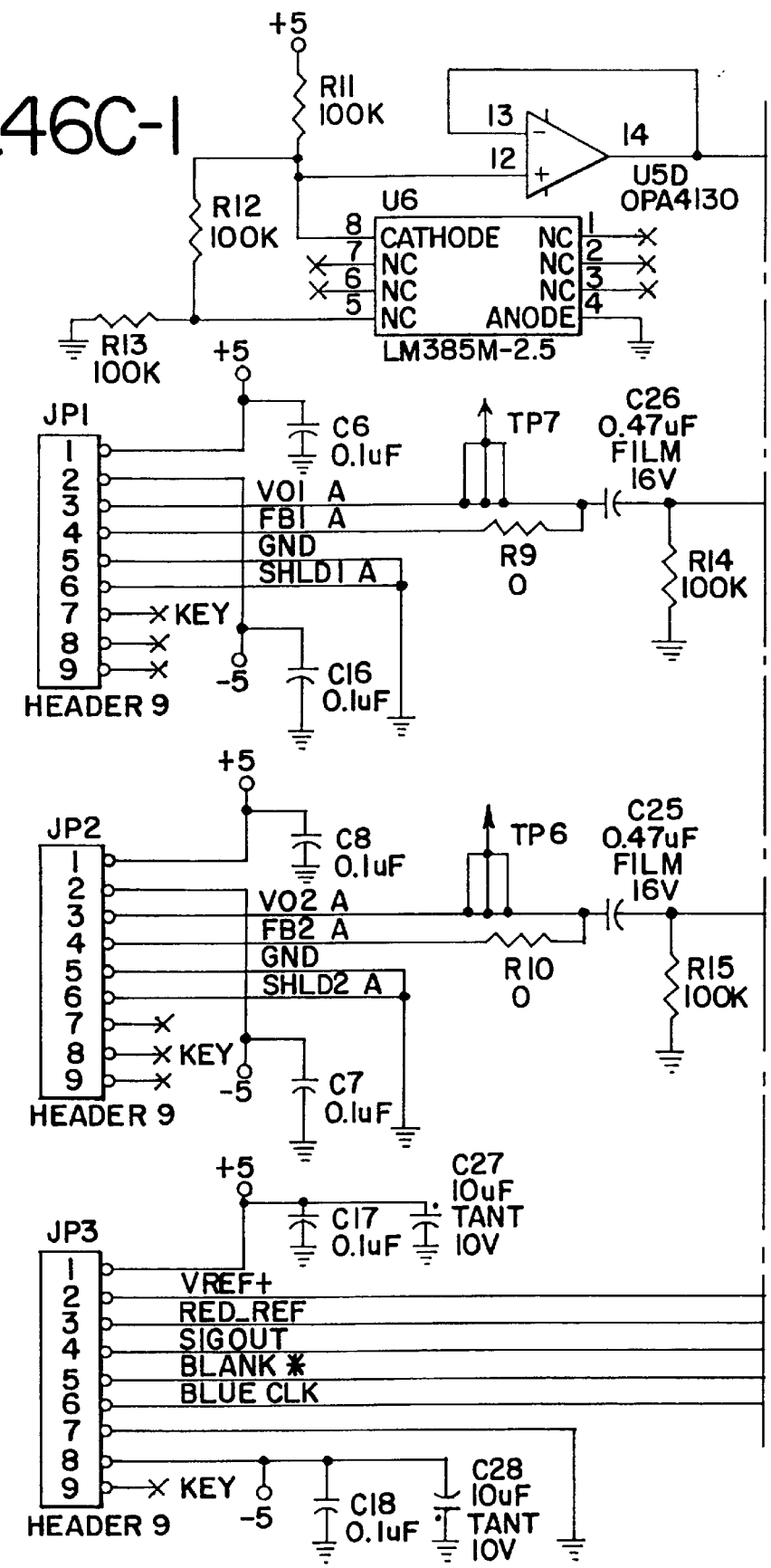
Figures 2, 46C:
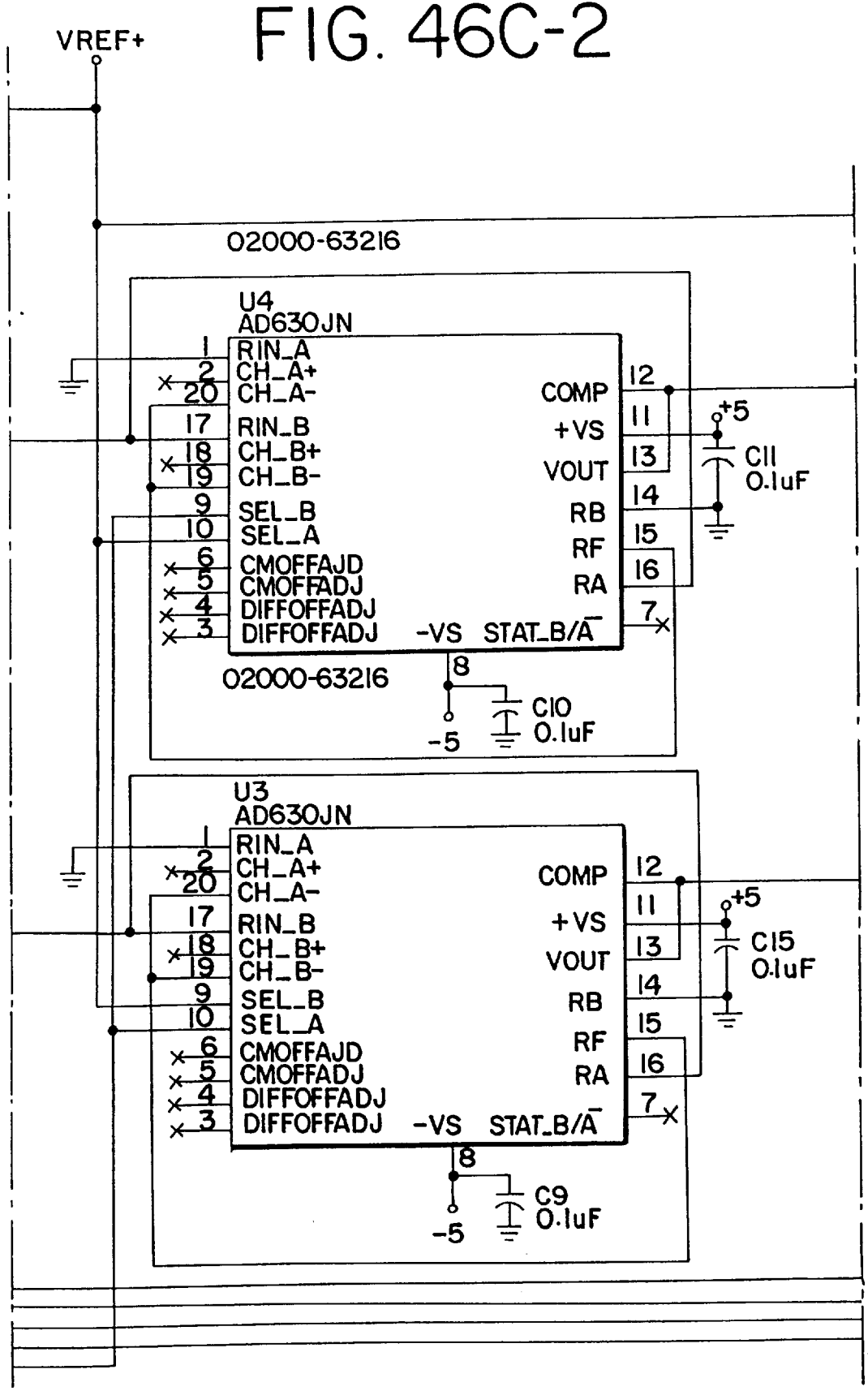
Figures 3, 46C:
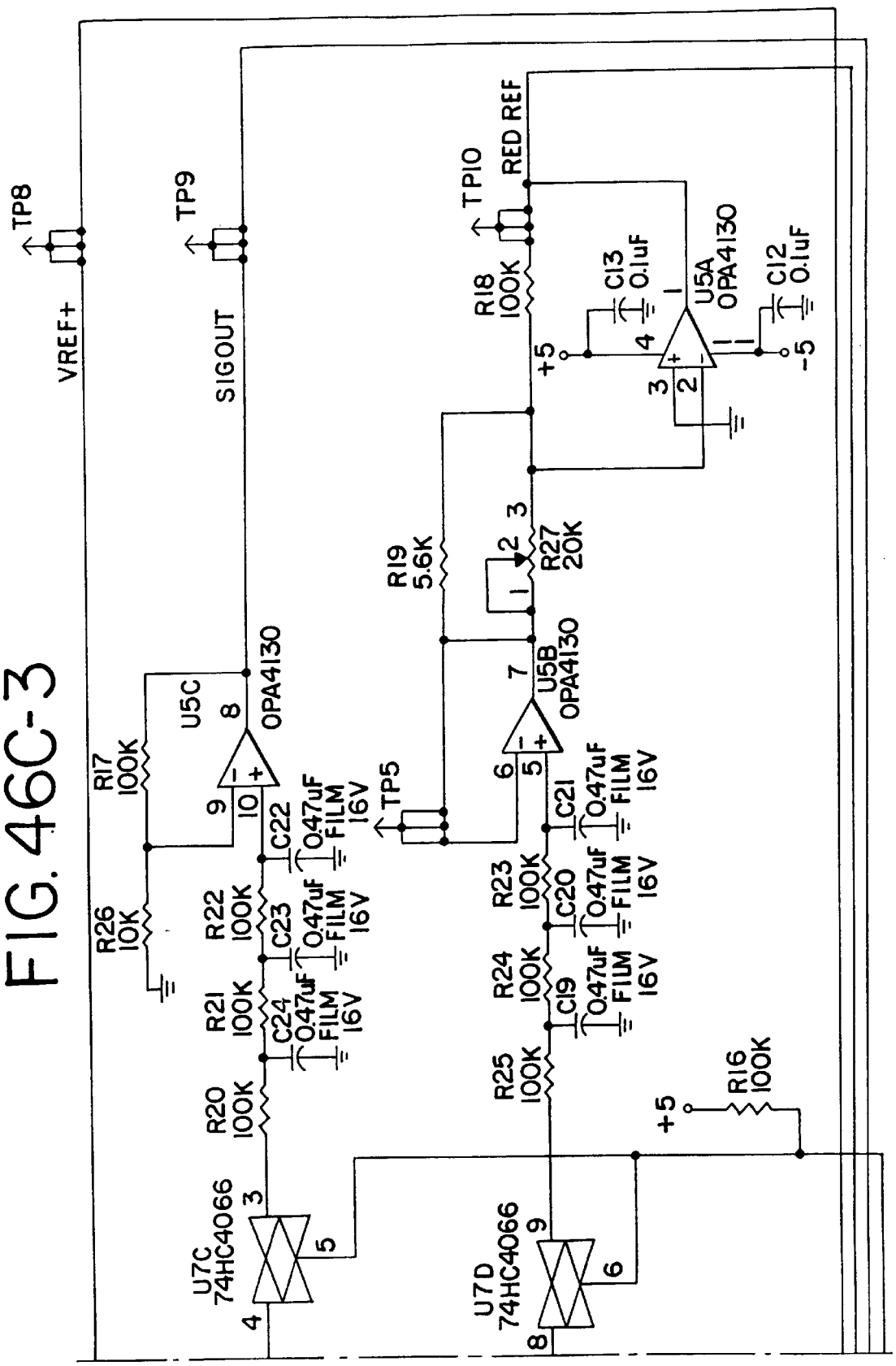
FIG. 3 is a cross-sectional view of the rear housing of the transfer device.

Luer fitting 34 is received in recess 34a of the cylindrical member 24 and is in fluid communication with a fluid exit channel 38 (FIG. 4). The luer fitting 34 can optionally be connected to a fluid collection bag or reservoir (not shown). The cylindrical member 24 also includes a hydraulic return channel 40 (FIG. 4) and a seed delivery channel 42 (FIG. 3). Each of the channels 36, 38, 40, and 42 communicate with the cylindrical recess 30.

A fluid control switch 44 selectively provides access between the various channels 36, 38, 40, and 42 to send and/or retrieve the radioactive treatment elements and marker seeds from the delivery catheter 14. To facilitate easy manipulation of the fluid control switch 44, a paddle-shaped control handle 46 is secured to the fluid control switch 44 and cylindrical member 24 by means of a retention screw 48 that extends through a central bore in the handle 46 and switch 44 and into a bore in the cylindrical housing 24. The bottom of the retention screw 48 abuts a set screw 49 to limit the movement of the screw 48 and prevent the screw 48 from being unscrewed by operation of the switch 44. A locking cap 50 closes the central bore in the handle 46. As best seen in FIG. 5, the fluid control handle 46 includes a paddle-like portion 52 which may be contoured or otherwise ergonomically-shaped to provide the user with improved control and easier manipulation of the fluid control switch 44.

Optionally, the head of the retention screw 48 may be notched so that a locking pin (not shown) may fit through it. Such a locking pin would prevent rotational movement of the retention screw 48 so that counterclockwise movement of the fluid control handle 46 would not loosen the screw 48. A shallow hole in the fluid control handle 46 where the head of the retention screw 48 rests would receive such a locking pin.

Figure 6I:
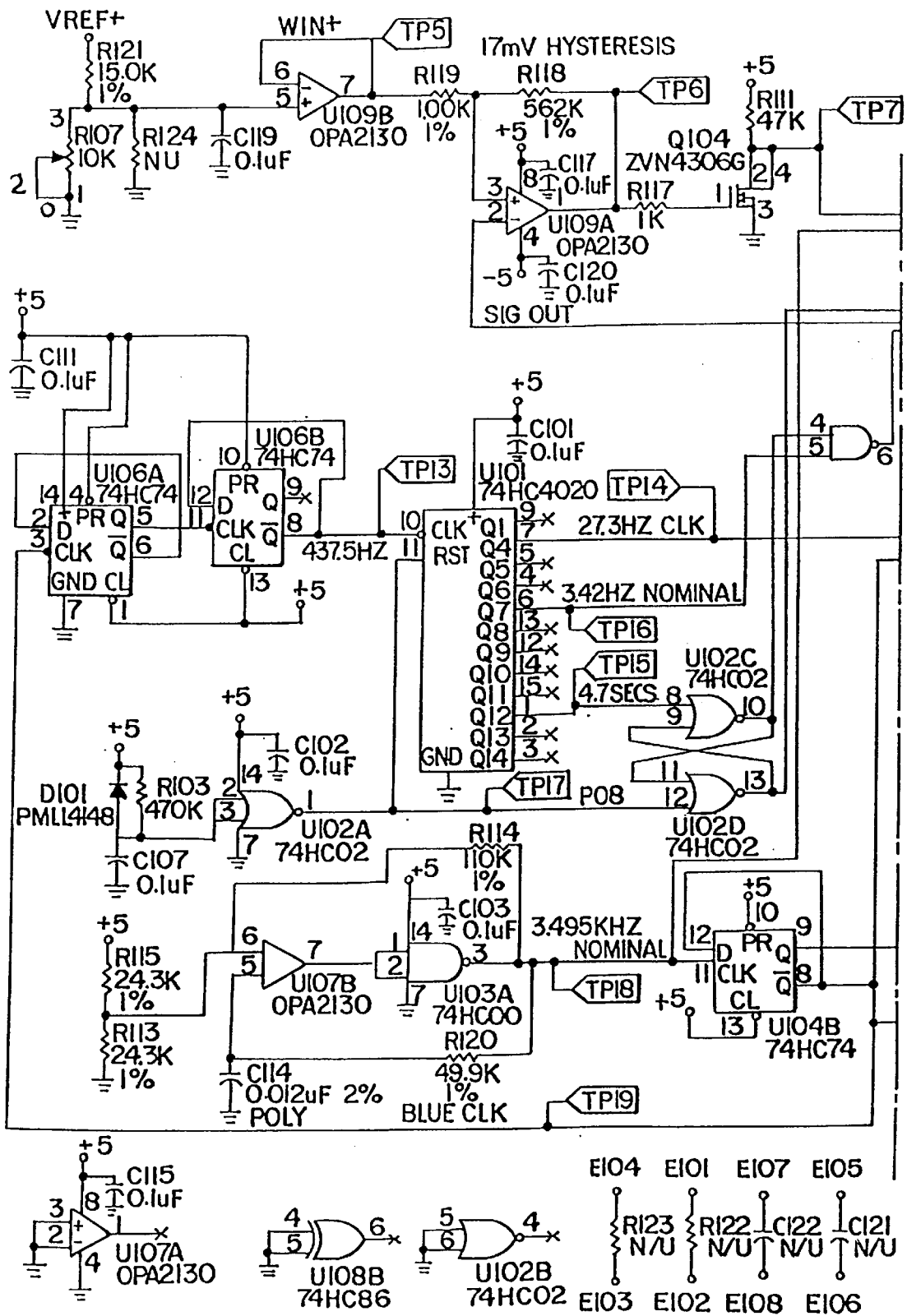
FIG. 6 is a perspective view of the fluid control switch.
Figure 6I:
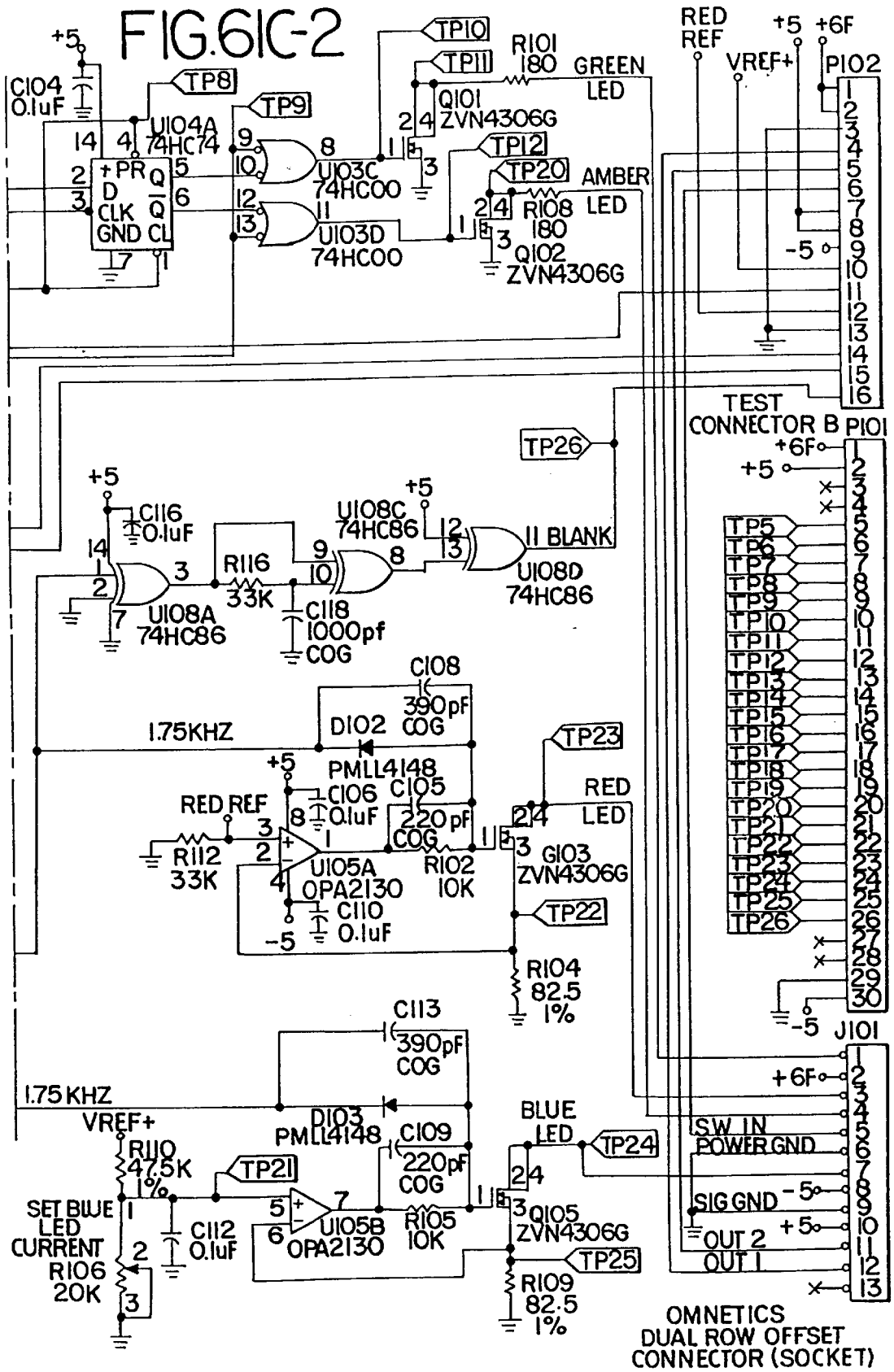
Figure 6D:
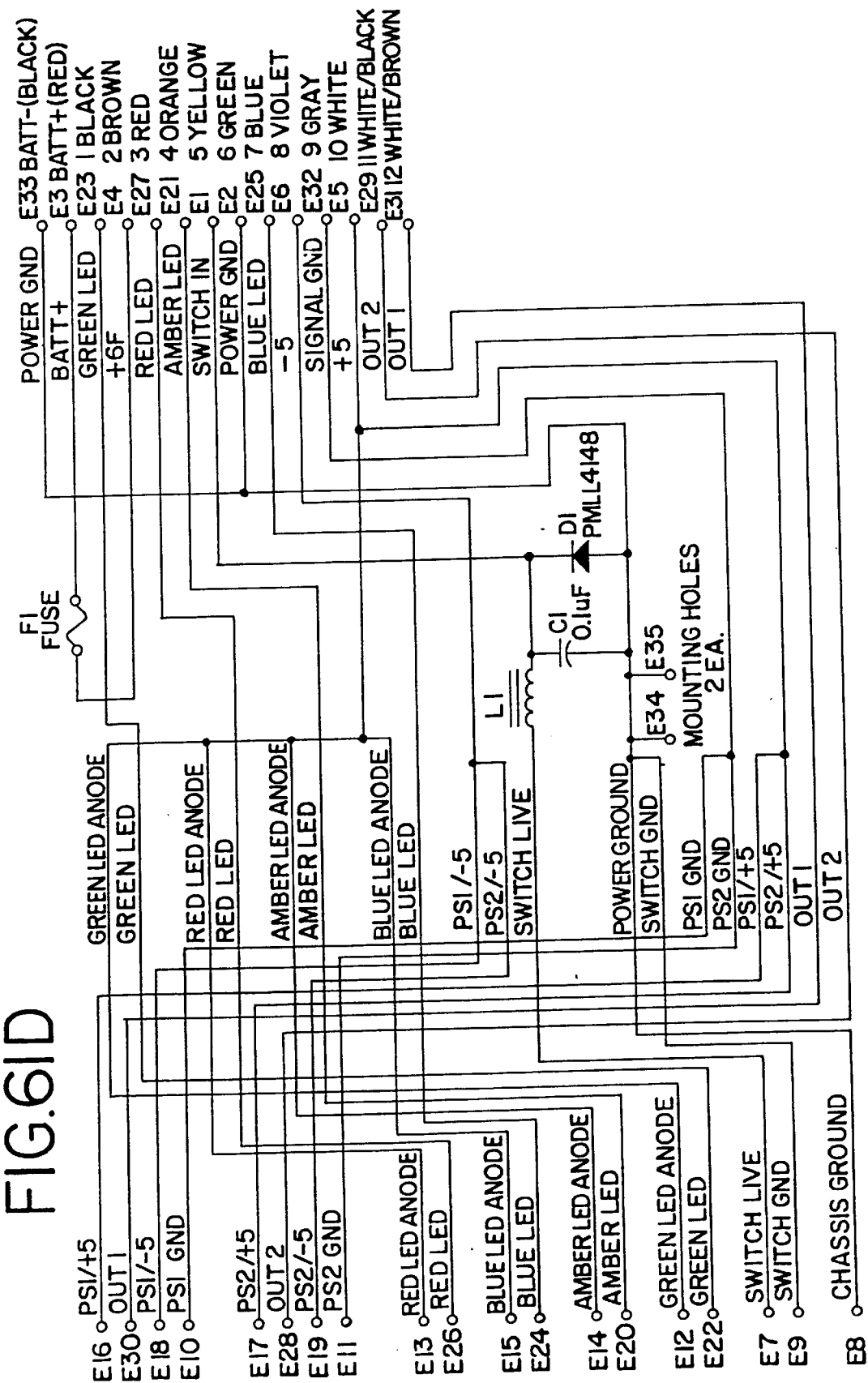

In order to limit the degree to which the fluid control switch 44 can be rotated, the bottom of the switch 44 includes a fluid control slot 54 (FIGS. 6, 7) which cooperates with an alignment pin 56 (FIG. 2) that is secured in a hole in the recessed area 30 of the rear housing member 18. To positively locate the switch in "off," "send," and "return" positions, the fluid control switch 44 also includes three dimples 58 (FIG. 6) that interact with a detent ball 60 and compression spring 62 (FIG. 2), which are housed in a short lumen 64 (FIG. 3) within the cylindrical member 24.

As best seen in FIG. 7, the bottom of the fluid control switch 44 includes a C-shaped connector channel 66 and an elliptical-shaped connector channel 68. The control switch 44 is relieved about the C-shaped and elliptical-shaped connector channels 66, 68 in order to receive o-rings 70 and 72, respectively, which seal the connector channels 66, 68 against the recess 30. To further prevent leakage around the fluid control switch 44, an o-ring 74 is received in an o-ring channel 76 about the exterior of the fluid control switch 44 (best seen in FIG. 6) and an o-ring 78 may be received by an o-ring channel about the distal opening of the switch 44. The o-rings 70, 72, 76 and 78 are preferably made of Buna-N or ethylene propylene.

In operation, when the fluid control switch 44 is in the "send" position, both the fluid injection channel 36 and the seed delivery channel 42 communicate through the C-shaped connector channel 66. Simultaneously the hydraulic return channel 40 and the fluid exit channel 38 communicate through the elliptical-shaped connector channel 68. Thus, fluid is allowed to flow through the fluid injection channel 36 through the C-shaped connector channel 66 and into the seed delivery channel 42. Fluid that bypasses the treating elements reaches the distal end of the delivery catheter 14 and returns to the hydraulic return channel 40 and is allowed, through the elliptical-shaped connector channel 68, to flow through the exit channel 38.

When the fluid control switch 44 is in the "return" position, both the fluid injection channel 36 and the hydraulic return channel 40 are aligned through the C-shaped connector channel 66. Simultaneously, both the seed delivery channel 42 and the fluid exit channel 38 are aligned though the elliptical-shaped connector channel 68. Consequently, fluid is allowed to flow through the fluid injection channel 36 into the C-shaped connector channel 66 and through the hydraulic return channel 40. As the treating elements are forced hydraulically from the distal end of the catheter back to the transfer device 12, fluid is allowed to flow from the seed delivery channel 42 to the fluid exit channel 38 through the elliptical-shaped connector channel 68.

When the fluid control switch 44 is in the "off" position, the fluid injection channel 36 is the only channel aligned with the C-shaped connector channel 66. Thus, no outlet exists for fluid flowing to the connector channel 66 from the fluid injection channel 36.

The transfer device 12 preferably includes a pressure relief valve (not shown) so that the system 10 cannot be over-pressurized. The valve would open to allow fluid in the system 10 to escape once the fluid pressure exceeded a certain, pre-determined value. Once the pressure in the system returns to a safe level, the valve would close. In one form, the valve may be spring-actuated, so that fluid pressure greater than the pre-determined value compresses the spring to open the valve, the valve being closed by the spring when the fluid pressure is reduced to below the pre-determined value. In addition, the transfer device 12 preferably includes an accumulator (not shown) or similar apparatus for maintaining a substantial amount of pressure against the radiation source train and marker seeds while they are positioned at the distal end of the catheter 14 so that they cannot migrate away from the distal end of the catheter 14 and the treatment site during radiation treatment. The accumulator may also be used to maintain a substantial amount of pressure against the treating elements and marker seeds so that they will remain completely within the lumen of the quartz sleeve 84 and visible to the users when they are not being used for radiation treatment.

Figure 8:
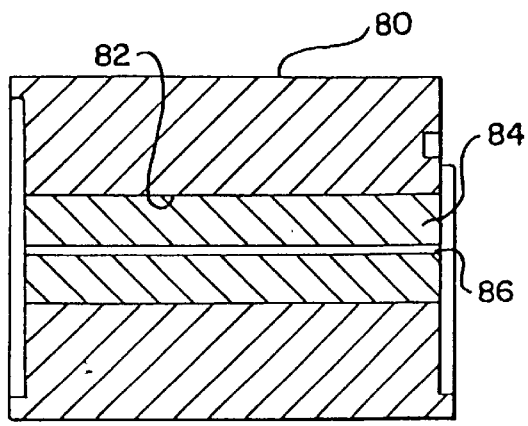
FIG. 8 is a cross-sectional view of the central housing of the transfer device including the quartz sleeve for holding the radiation elements.

Distal of the rear housing 18 and connected thereto is the central housing and actuator switch/shuttle gate assembly 20. Proper alignment of the rear housing 18 and the central housing and actuator switch/shuttle gate assembly 20 may be assured by alignment pins (not shown). The assembly 20 includes a central housing 80 having a central lumen 82 for receipt of the quartz sleeve 84 (FIG. 8) which extends the entire length of the central housing 80 and in which the radiation source train or seeds are stored.

The central housing 80 is cylindrical in shape and preferably made of clear Lexan or clear polycarbonate. The quartz sleeve 84 is preferably made of natural or synthetic quartz or quartz glass (fused quartz), or other materials consisting of natural or synthetic fused silica. A lumen 86 extends the entire length of the quartz sleeve 84 and the radiation source seeds and marker seeds are stored within the lumen 86 when the seeds are not being delivered to the treatment site. The quartz sleeve 84 is used to shield the radiation emitted from the source train so that the transfer device 12 can be handled safely. The quartz material does not break down as a result of storing the radiation-emitting treatment seeds and also remains clear so that the seeds can be visually detected. The quartz rod is of sufficient thickness to block at least 99 percent of the radiation. In practice, a thickness of 1 cm has been found to be sufficient.

In order to more easily discern the presence of the radiation source seeds and marker seeds within the quartz sleeve 84, the sleeve is of one uniform diameter and has no steps or o-rings disposed thereon. Thus, the entire length of the quartz sleeve can be seen. The lower half of the quartz sleeve 84 can be covered with a white film, preferably vinyl or Tyveks®, to create a contrasting background for the source seeds. Additionally or alternatively, a magnifying piece may either encase the quartz sleeve 84 or lie along the top of the quartz sleeve to better permit visualization of the radiation source seeds. Additionally, a light source could be utilized to better visualize the source and marker seeds.

As best seen in FIGS. 3 and 9, a rear housing insert 88 with a lumen therethrough comprises an intermediate member between the rear housing 18 and central housing 20 for providing fluid communication between the seed delivery channel 42 and the lumen 86 of the quartz sleeve 84 through lumen 90 of the insert 88. The lumen 90 is L-shaped and precludes the treating elements from migrating into the rear housing 18, while insuring fluid communication between the rear housing lumens and the quartz lumen.

Figure 10:
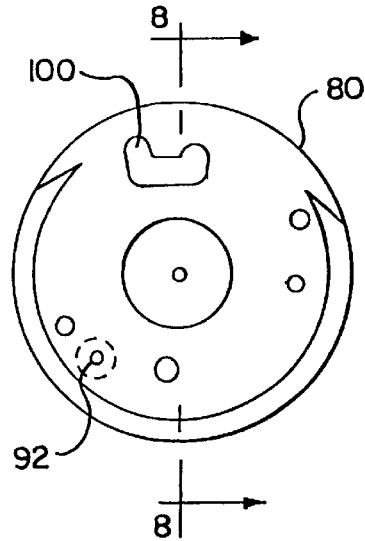
FIG. 10 is a plan view of the distal face of the central housing.

A smaller, off-axis through-lumen 92 extends through the central housing 80 (FIG. 10) and is a continuation of the hydraulic return channel 40 in the rear housing 18. Fluid leakage between the connection of the return lumen 40 and the rear housing 18 and the return lumen 92 in the central housing 80 is prevented by a means of an o-ring 94 (FIG. 2), preferably made of Buna-N or ethylene propylene.

An actuator switch 96 is located at the distal end of the central housing 80 that pivots a shuttle gate 98 to operate the system. The actuator switch 96 allows for two positions: "connect/prime" and "send/retrieve." The connect/prime mode allows for connection of the connector 16 (FIG. 1) through the transfer device 12. After being connected, the connect/prime mode allows for flushing and priming of the transfer device 12 and the catheter 14 without the delivery of the radiation source train.

The send/retrieve mode allows for the delivery of the radiation source train and marker seeds to, and retrieval from, the distal end of the catheter 14. The send/retrieve mode of the actuator switch 96 cannot be accessed unless the connector 16 has been locked into the transfer device 12. This prevents inadvertent delivery of the radiation source train to any location other than the delivery catheter 14. To this end, the distal face of the central housing 80 includes a recessed area 100 (FIG. 10) in the general shape of a squared U. The recess 100 receives the proximal end of positioning pin 102 (FIG. 2) to positively lock the actuator switch 96/shuttle gate 98 in position for two modes discussed above.

Figure 11:
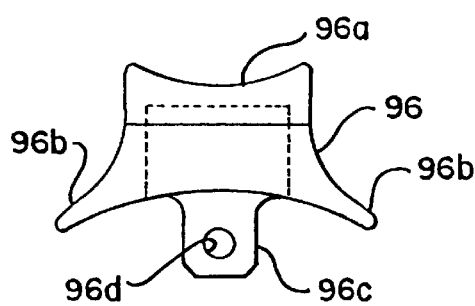
FIG. 11 is a plan view of the actuator switch.

The actuator switch 96 is made of a hard plastic material, such as Acetal or Delrin. The actuator switch 96 has a top portion 96a (FIG. 11) that has a depression so that the user may use solely a thumb or a finger to operate the switch. The actuator switch also includes two slightly curved arms 96b that extend outwardly and downwardly from the midsection of the switch 96. Two rectangular legs 96c extend from the bottom of the switch 96, with each leg 96c having a hole 96d therethrough for receipt of the positioning pin 102. Between the two legs 96c, a hollow portion extends into the midsection of the switch 96 for receiving the top portion of the gate 98 and a compression spring 104 (FIG. 2).

Figure 12:
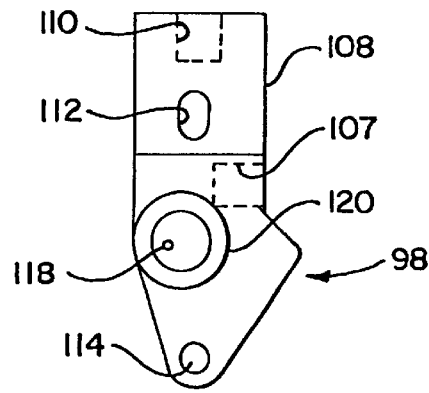
FIG. 12 is a plan view of the gate.

The shuttle gate 98 is made of a plastic material, such as Acetal or clear polycarbonate, and is of sufficient thickness to insure stability when the gate pivots. The shuttle gate 98 includes a body portion 106 (FIG. 12) that has a shoulder and tapers inward to a curved bottom. The body portion 106 includes a hole 107 for receipt of a compression spring 105 (FIG. 2) which biases the shuttle gate 98 toward the connect/prime mode. A neck 108 extends upwardly from the body portion 106 of the gate 98 and includes a hole 110 in which the compression spring 104 is received. Neck 108 also includes a slot 112 for receiving the positioning pin 102. The gate 98 includes a through hole 114 at its bottom for receipt of a pivot pin 116 (FIG. 2), so that the gate 98 can rotate about the pivot pin 116. The gate 98 also includes a hole 118 between the axis pin hole 114 and the positioning slot 112 that is large enough to allow the treating elements to pass therethrough. An o-ring groove 120 exists on each side of the gate for receiving an o-ring 122 (that encircles the proximal opening of the seed hole) and an o-ring 124 (that encircles the distal opening of the seed hole). The o-rings 122, 124 (FIG. 2) are located so that when the actuator switch/shuttle gate are moved between their various locations, the o-rings do not travel across the edges of any other parts, thus reducing wear on the o-rings and providing for smoother action when operating the gate 98.

In operation, the compression spring 104 biases the actuator switch 96 away from the shuttle gate 98. When the actuator switch 96 is pressed downward against the force of the compression spring 104, the positioning pin 102 is moved towards the bottom leg of the U-shaped recess 100 in the central housing 80 and the collar housing 146 to permit movement of the actuator switch 96 and the shuttle gate 98 between the two positions.

Figure 13:
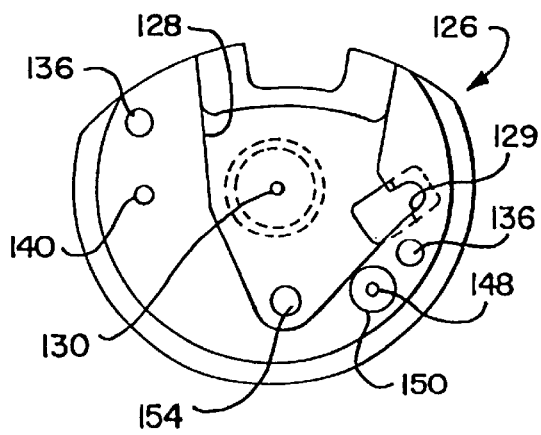
FIG. 13 is a plan view of the proximal face of the gate housing.
Figure 14:
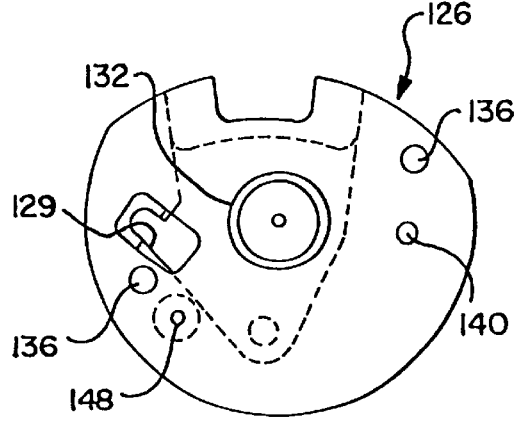
FIG. 14 is a plan view of the distal face of the gate housing.

The shuttle gate 98 is secured to the distal end of the central housing 80 by a gate housing 126. As best seen in FIG. 13, the proximal side of gate housing 126 has a recessed area 128 in the general shape of shuttle gate 98 and a generally rectangular opening 129. When the gate 98 is in this recessed area 128 the neck 108 extends beyond the gate housing 126. The gate housing 126 includes a seed lumen 130 which is chamfered at both its proximal and distal ends to facilitate the delivery of the treating elements. (The seed lumens in the other housings may also be chamfered at their ends to facilitate delivery of the treating elements.) The distal side of the gate housing 126 (best seen in FIG. 14) has a circular recessed area 132 with a beveled edge encircling the seed lumen for better alignment with the connector 16. For alignment of the gate housing 126 with the central housing 80 and a collar housing 146, the gate housing 126 also has holes 136 for receiving screws 138 (FIG. 2) and an alignment hole 140 for receiving alignment pins 142, 144 (FIG. 2). The gate housing 126 also includes a fluid return channel 148 (a continuation of the fluid return channel 92 in the central housing 80) and an annular groove 150 on the proximal side of the gate housing 126 for receipt of an o-ring 152 (FIG. 2). An aperture 154 on the proximal side of the gate housing receives the distal end of the pivot pin 116 for the shuttle gate 98.

Figure 15:
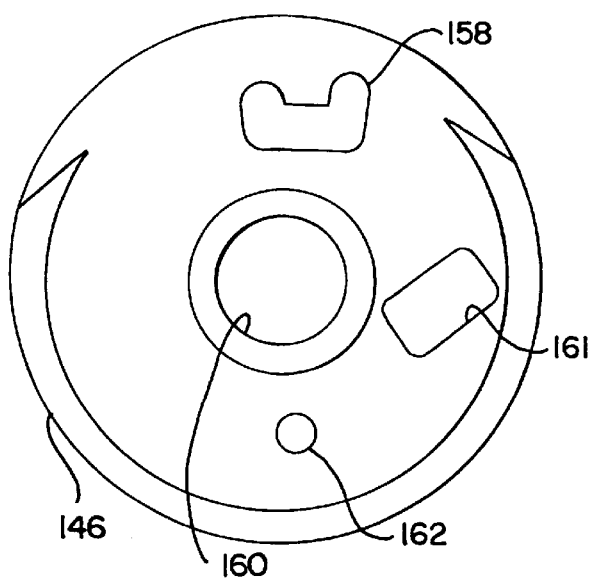
FIG. 15 is a plan view of the proximal face of the collar housing.

The collar housing 146 is positioned intermediate the gate housing 126 and a front housing 156. The proximal face of the collar housing 146 (FIG. 15) is shaped similarly to the distal face of the central housing 80 (FIG. 10) and includes a recess 158 that compliments the recess 100 in the central housing 80 and receives the distal end of the positioning pin 102 of the shuttle gate 98.

The collar housing 146 has an enlarged central opening 160 for receiving the connector 16 (FIG. 1) and which is relieved on the proximal side of the collar housing 146 for receipt of o-ring 134 (FIG. 2). A rectangular opening 161 extends through the collar housing 146. The collar housing 146 includes a fluid return channel 162 (a continuation of the fluid return channel 148 in the gate housing 126) with an annular o-ring groove surrounding the proximal opening thereof for receipt of o-ring 164 (FIG. 2). An alignment hole is also included for receipt of alignment pin 144 to align the collar housing 146 with the gate housing 126 and another hole for receiving alignment pin 166 for aligning the collar hosing 146 with the front housing 156.

Cut-outs on the distal face of the collar housing 146, with complimentary cut-outs in the proximal face of the front housing 156, receive a release button 168, release switch 170, and release trigger 172, which cooperate to receive and lock the connector 16 into the transfer device 12 and to release the connector 16 from the transfer device 12 as well. The interaction of the release button 168, release switch 170, and release trigger 172 are described in greater detail below.

Figure 16:
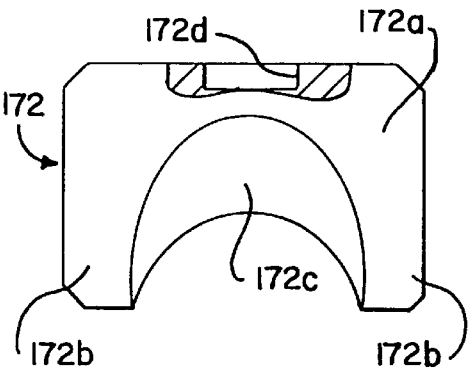
FIG. 16 is a plan view of the release trigger.

The release trigger 172 (FIG. 16) includes a generally rectangular body 172a with two legs 172b extending therefrom. A sloped relief of parabolic shape 172c on the distal side of the trigger 172 makes up the edge between the two legs 172b. The top of the release trigger 172 includes a shallow bore 172d for receiving one end of a compression spring 174 (FIG. 2).

Figure 17:
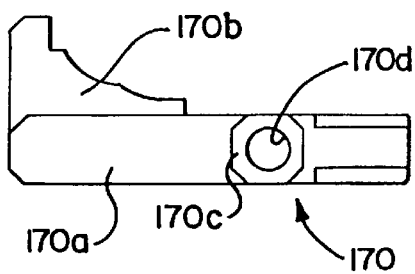
FIG. 17 is a plan view of the release switch.
Figure 18:
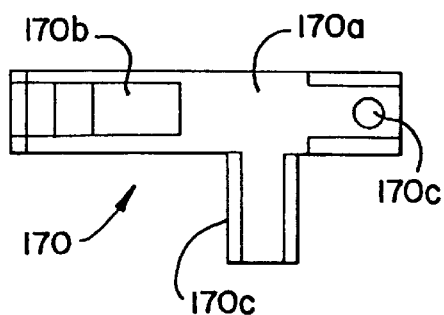
FIG. 18 is a top view of the release switch.

The release switch 170 (FIG. 17) includes an elongated rectangular body 170a with a curved and notched ramp 170b at one end and a protruding arm 170c (FIG. 18) at the other end. The arm 170c includes a bore 170d for receipt of a dowel pin 176 (FIG. 2). The release button 168 is secured to the release switch 170 by means of a screw 178 (FIG. 2) that is received in a hole 170e in the release switch 170. Alternatively, the release button 168 may be an integral part of the release switch 170.

The front housing 156 completes the distal end of the transfer device 12 and includes a central lumen 180 (FIG. 19) for receiving the connector 16. The distal portion of the central lumen 180 is relieved at 181 (FIG. 20) to seat two o-rings that fit on the outside of the connector 16 when the connector is locked into the transfer device 12 (to seal the connection between the connector 16 and a fluid return lumen 184 in the front housing 156. The front housing 156 includes two holes 182 for receiving the screws 138 that secure the front housing 156, collar housing 146, and gate housing 126 to the central housing 80. As described above, the lumens in the central housing 80 that receive the screws 138 can optionally be lined with helical, coiled wire inserts or include threaded metal inserts to provide a more durable connection. The front housing 156 also includes a fluid return lumen 184 (a continuation of the fluid return lumen 162 in the collar housing 146) that has an annular o-ring groove surrounding the proximal opening for receipt of an o-ring 186 (FIG. 2). An aperture in the proximal face receives alignment pin 166 for insuring alignment of the front housing 156 with the collar housing 146.

Turning now to the operation of the actuator switch/shuttle gate, when the gate 98 is in the closed position (and the connector 16 is not connected to the transfer device 12), the release switch 170 rests upon a compressed spring 190 (FIG. 2) with one of the legs 172b of the release trigger 172 engaging the uppermost portion of the ramp 170b of the release switch 170 to keep the release switch pressed down against the compressed spring 190 (FIG. 19a). In this condition, the release button 168 is completely recessed in the opening between the collar housing 146 and front housing 156. The end of the dowel pin 176 extends through the openings 129 and 161 in the gate housing 126 and collar housing 146, respectively, at the bottom of the openings 129, 161 and is positioned adjacent to gate 98 to prevent the gate from pivoting to and engaging in the seed transit mode.

Figure 19B:
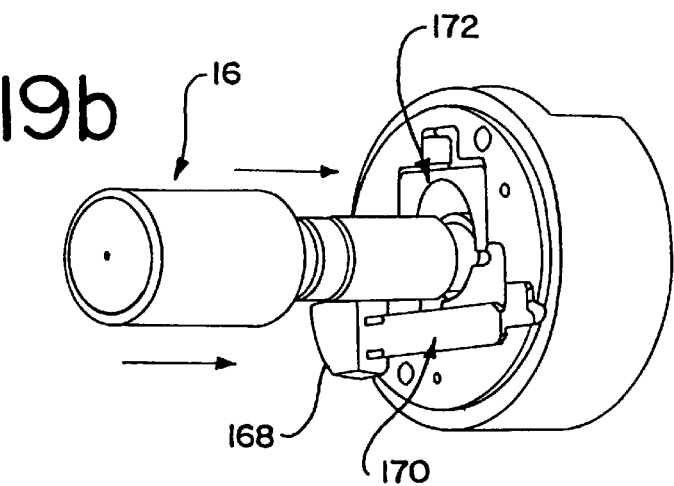
Figure 19C:
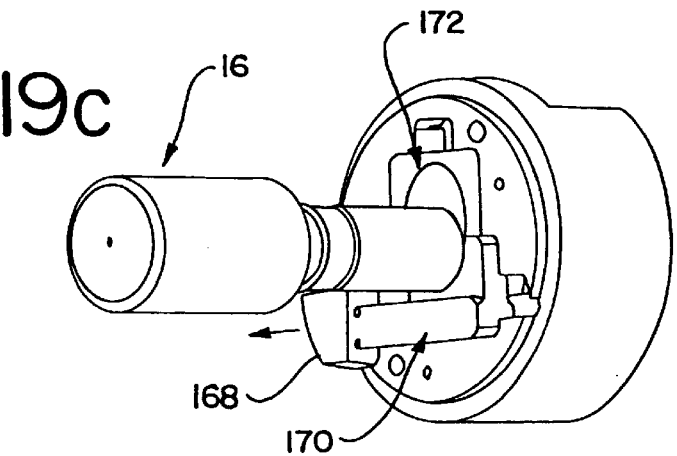

When the connector 16 is inserted into the central lumen 180 of the front housing 156, the proximal end of the connector 16 contacts the sloped relief 172c of the release trigger 172 to force the trigger 172 upwardly, while simultaneously compressing the spring 174 (FIG. 19b). As the release trigger 172 moves away from the release switch 170, movement of the release switch 170 is no longer impeded and the release switch, biased by the compressed spring 190, moves upwardly until the curved ramp 170b engages an undercut section on the connector 16. This locks the connector 16 into the transfer device 12. When the release switch 170 is moved to lock onto the connector 16, the release button moves out of its recessed area to visually confirm that the connector 16 is locked into the transfer device (FIG. 19c). Simultaneously, the dowel pin 176 moves to the top of the openings 129, 161 so that it no longer prevents the gate 198 from engaging into the seed transit mode.

The actuator switch 96 can now be moved from the connect/prime mode to the seed transit mode by pushing down on the actuator switch 96 to force the positioning pin 102 downward to the bottom of the grooves 100 (in the central housing 80) and 158 (in the collar housing 146). While maintaining a downward force on the actuator switch 96, a horizontal force is then applied to the actuator switch 96 to move the positioning pin 102 through the horizontal groove of the recesses 100, 158 to the other vertical groove. The switch 96 is then released and the positioning pin 102 moves up to the top of the vertical groove to place the switch 98 in the seed transit mode. When the actuator switch 96 is engaged in the seed transit mode, the gate 98 is positioned so that a portion of the gate 98 now occupies the same space that was occupied by the dowel pin 176 in the connect/prime mode.

To remove the connector 16 from the transfer device the actuator switch 98 is moved into the connect/prime mode after all the treating elements and marker seeds have been returned to the quartz sleeve 84. Once the actuator switch 98 is in the connect/prime mode, the release button 168 is pressed inwardly to move the release switch 170 downwardly against the spring 190. The dowel pin 176 simultaneously moves so as to prevent movement of the gate 98 back to the seed transit mode. The connector 16 can then be manually withdrawn from the transfer device. Withdrawal of the connector 16 allows the release trigger 172 to be forced by the spring 174 to drop down and reposition one of its legs 172b in front of the ramp 170b, returning the release button 168, the release switch 170, and the release trigger 172 to their initial positions.

The release button 168 cannot be activated while the actuator switch 96 is in the seed transit mode. In the seed transit mode, the gate 98 is positioned so that it hinders downward movement of the dowel pin 176. Because the dowel pin 176 is connected to the release switch 170, downward movement of the release switch 170 is also impeded and the curved ramp 170b cannot disengage from the connector 16.

Turning to FIGS. 21–27, there is seen a further embodiment of the rear housing/fluid control switch for use in the transfer device 12 of the present invention. As seen in FIG. 21b, the rear housing 200 is generally cylindrical in shape and includes two axial through-lumens 202 for positioning two screws (such as screws 28 in FIG. 2) to secure the rear housing 200 to the central housing. The rear housing includes two recesses 204, 206 for receipt of luer fittings or connectors similar to connectors 32, 34 shown in FIG. 2. Such luer fittings would be secured in the recesses 204, 206 by means of an adhesive. The luer fittings may be partially or completely recessed within the rear housing 200. Preferably the luer connector received in recess 204 provides for attachment to a liquid or gas filled device (not shown) that is used for hydraulic or pneumatic delivery and retrieval of the radiation source train and marker seeds to and from the delivery catheter 14. The luer connector secured in recess 206 attaches to a fluid collection bag (not shown).

Toward the distal end of the rear housing 200 there is a cylindrical bore 208 that receives the fluid control switch 210, which will be described in detail later. The diameter of the cylindrical bore 208 is slightly smaller than the largest diameter of the fluid control switch 210 so that the fluid control switch 210 fits tightly within the bore 208. A fluid inlet channel 212 connects recess 204 to the cylindrical bore 208 (FIG. 22); a fluid exit channel 214 connects recess 206 to the cylindrical bore 208 (FIG. 23); a fluid return/seed retrieval channel 216 connects the cylindrical bore 208 with an opening 218 in the distal face of the rear housing 200 (FIG. 22 or 23); and a fluid return/seed delivery channel 220 connects the cylindrical bore 208 to a central distal opening 222 including a rear housing insert 224 (similar to insert 88 in FIG. 9) (FIG. 22 or 23).

The fluid control switch 210 is a solid cylinder, preferably made of a white or clear Teflon material to allow smooth movement of the cylinder 210 within the central bore 208, and includes four fluid channels (described below) for selectively connecting channels 212 and 214 with channels 216 and 220. The switch 210 includes a rectangular cut-out 226 at its upper end for receipt of handle 228 the rectangular cut-out 226 is sized so that the distal end 230 of the handle 228 fits snugly within it.

The handle 228 is enlarged at its distal end 230 so that it has an overhang or step 231. When the distal end 230 of the handle 228 is fitted into the rectangular cut-out 226 in the fluid control switch 210, and the fluid control switch 210 is positioned in the cylindrical bore 208 of the rear housing 200, the entire overhang 231 is positioned within the circumference of switch 210, and the overhang 231 of the handle 228 abuts the sidewall of the central bore 208, thus preventing removal of the handle 228 from the cut-out 226 and securing the handle 228 within the switch 210.

The fluid control switch 210 includes four channels 242, 244, 246, and 248 for selectively connecting the fluid inlet channel 212 and fluid exit channel 214 with the fluid return/seed retrieval channel 216 and fluid return/seed delivery channel 220. As best seen in FIGS. 26 and 27, the fluid control switch 210 includes a seed delivery channel 242, a fluid return channel 244, a seed retrieval channel 246, and a fluid return channel 248.

In operation, when the fluid control switch 210 is in the "send" position, both the fluid inlet channel 212 and the seed delivery channel 220 in the rear housing 200 communicate through the seed delivery channel 242 in the fluid control switch 210. Simultaneously, the fluid exit channel 214 and fluid return/seed retrieval channel 216 in the rear housing 200 communicate through fluid return channel 248 in the fluid control switch 210. Thus, fluid is allowed to flow from, e.g., a syringe, through the fluid inlet channel 212, through the seed delivery channel 242 in the switch 210, and into the seed delivery channel 220 to advance the treatment elements to the distal end of the delivery catheter. Fluid that bypasses the treatment elements reaches the end of the delivery catheter and returns to the fluid return/seed retrieval channel 216 and is allowed, through the fluid return channel 248 in the switch 210, to flow through the fluid exit channel 214 and into, e.g., a fluid collection bag.

When the fluid control switch 210 is in the "retrieval" position, both the fluid inlet channel 212 and the fluid return/seed retrieval channel 216 in the rear housing 200 communicate through seed retrieval channel 246 in the fluid control switch 210. Simultaneously, both the fluid exit channel 214 and the seed delivery channel 220 in the rear housing 200 communicate through the fluid return channel 244 in the fluid control switch 210. Consequently, fluid is allowed to flow through the fluid inlet channel 212, into the seed retrieval channel 246, through the fluid return/seed retrieval channel 216, and into the catheter to hydraulically force the treating elements from the distal end of the catheter back to the transfer device. Simultaneously, fluid is allowed to flow from the seed delivery channel 220, through the fluid return channel 244, into the fluid exit channel 214, and out of the transfer device.

When the fluid control switch 210 is in the "off" position, none of the channels 212, 214, 218, 220, 242, 244, 246, and 248 communicate with each other. Thus, no outlet exists for any fluid from the fluid inlet channel 212.

The fluid control switch 210 includes a channel or groove 250 that receives o-ring 252 to prevent leakage out of the cylindrical bore 208 (FIGS. 24, 25). The fluid control switch 210 also includes three areas of enlarged diameter, generally indicated by 254, to prevent cross-talk among the fluid channels 242, 244, 246 and 248. These areas of enlarged diameter correspond with the openings of the channels 242, 244, 246, 248 and create a tight seal about the fluid openings. Alternatively, o-rings could be used in place of the areas of greater diameter.

On the distal face of the fluid control switch 210 there is an oblong opening 232 (FIG. 27) which extends radially along the face of the switch 210 so that, when the switch 210 is placed within the cylindrical bore 208, the oblong opening 232 aligns with a short through lumen 234 in the rear housing. The oblong opening 232 terminates internally of the fluid control switch 210 with three dimples 236 which interact with a compression spring 238 and detent pin 240 (FIG. 21b) to assist in the positioning of the fluid control switch 210 (similar to the compression spring 62 and ball detent 60 shown in FIG. 2). The ends of the oblong opening 232 act as stops in conjunction with the detent pin 240 to limit the degree to which the fluid control switch 210 can be rotated.

The detent pin 240 has a ball-shaped end that rests within the dimples 236. In the "off" position the detent pin 240 rests within the middle dimple. As the fluid control switch 210 is moved to either the "send" or the "retrieval" mode, the middle dimple moves away from the detent pin 240, while either end dimple moves towards the pin. As the switch 210 and dimples rotate, the detent pin is pushed back against the compression spring 238. As one of the end dimples becomes aligned with the pin, the force of the spring 238 propels the pin 240 forward so that the ball of the pin 240 rests within the dimple. Because when the pin moves away from the dimples during rotation of the cylinder it does not move outside of the opening 232, the pin secures the cylinder 210 within the rear housing 200 at all times.

Turning to FIGS. 29–33, there is seen an improved transfer device 300 for handling and delivering the treating elements in conjunction with the intraluminal radiation system of the present invention. In contrast to the previously described transfer devices 12, the transfer device 300 includes an ergonomically designed exterior that is more easily gripped by the user. Additionally, the various internal components of the transfer device 300 are unitized for easier construction and assembly. The transfer device 300 also features additional or improved safety features, such as treatment seed detection circuit and display, a fluid pressure indicator/relief valve, and a catheter connector/seed or pin gate interlock, all of which are described in greater detail below.

Turning to the exploded view of FIG. 31, it can be seen that the transfer device comprises a two-part shell, including shell halves 302a and 302b which enclose a chassis 304, on which the various components of the transfer device 300 are mounted. The shell half 302a includes a magnifying window 306 for viewing the quartz sleeve or housing 308 having a lumen 308a that holds the treatment seeds (not shown), indicator lights or "annunciators" comprising LEDs 310a and 310b (FIG. 30) that indicate whether the treatment seeds are residing in the quartz sleeve or elsewhere in the transfer device and its associated catheter, a power button 312 for activating the LED seed detection/indicator system, a pressure indicator window 314 for providing a visual indication of the fluid pressure within the treatment system, and a fluid control button 316 (similar in function to fluid control handle 44 or 228 described above) for actuating the fluid control switch. Along the side of the housing shell half 302a are a release button 318 for the catheter connector (similar in function to the release button 168 described above), and a sliding gate actuator switch 320 that covers the release button 318 to prevent the unintentional release of the catheter connector when the treatment seeds are being transferred to or are inside of the catheter. The transfer device 300 also includes a compartment 319 at its proximal end (FIG. 33) for receiving a fluid collection bag (not shown).

Turning to FIGS. 29A and B, the transfer device 300 is shown with a detachable syringe 322 which provides the pressurized fluid for hydraulic delivery and retrieval of the treatment seeds used in the system. The syringe 322 is connected to the transfer device by a luer lock 324 and is supported on the transfer device by a saddle having two offset arms 326a and 326b (best seen in FIGS. 30 and 31) that extend from shell halves 302a and 302b, respectively, and wrap around the barrel 322a of the syringe 322 to firmly hold the syringe to the transfer device. As can be seen in FIGS. 29A and B, the syringe 322 is held at an angle from the longitudinal axis of the transfer device to permit easier manipulation of the syringe plunger 322b.

As indicated above, the interior components of the transfer device 300 are constructed separately and are mounted to the chassis 304, where they are preferably joined together for fluid communication by means of polyethylene tubing (not shown) and barbed connectors such as, e.g., 328 (FIG. 31). This type of construction may permit simpler and more economical construction and assembly of the transfer device than the previously described embodiments in which, e.g., the various housing members (and their respective fluid passageways) and the fluid control switch are machined from blocks of solid material that have to be joined together. For example, the fluid control switch 330 of the transfer device 300 may comprise a standard four port valve body, such as valve model no. 7017KV, manufactured by the Kloehn Co. of Brea, Calif., rather than the custom-machined switches 44 (FIGS. 1, 2, 6, 7) or 210 (FIGS. 21B, 24–27) and their respective interfitting rear housing members 18, 200.

With reference to FIGS. 29B, 31, and 37, the chassis 304 of the transfer device 300 also supports a pressure indicator/pressure relief valve, generally indicated by 332, that is visible through the pressure indicator window 314 on shell half 302a. The pressure indicator/relief valve 332 is in fluid communication with the syringe 332 and is designed to provide an easily-readable visual indication of the relative fluid pressure in the treatment system and to release the fluid to the reservoir when it exceeds a predetermined maximum valve (e.g., 100 psi), thus insuring that the fluid pressure does not attain a level that could possibly damage either the transfer device or its associated catheter.

With reference to FIGS. 35A–D, the pressure indicator/relief valve comprises a cylinder 334 with having an inlet port 336 in fluid communication with the syringe 322.

Figure 35C:
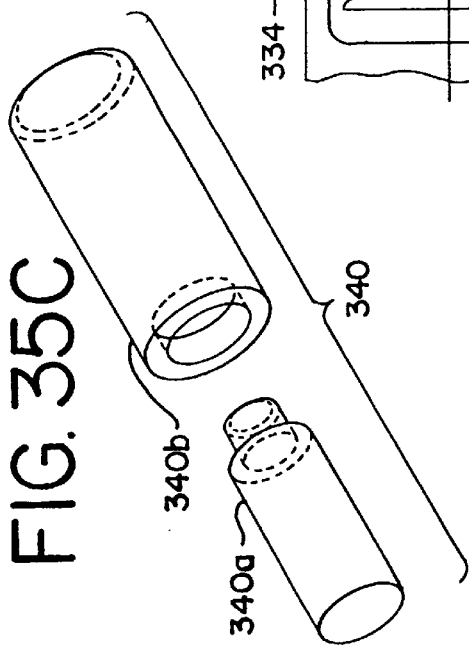
Figure 35D:
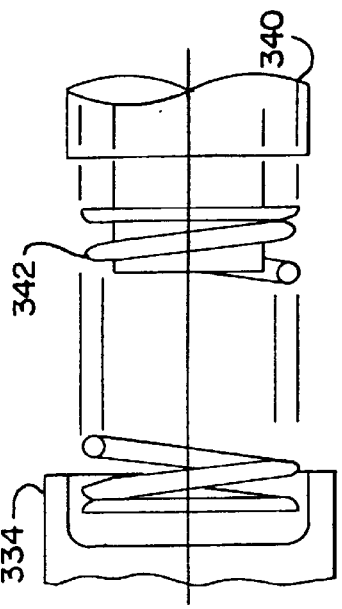
Figure 35A:
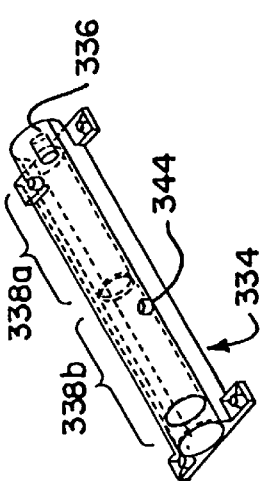
Figure 35B:
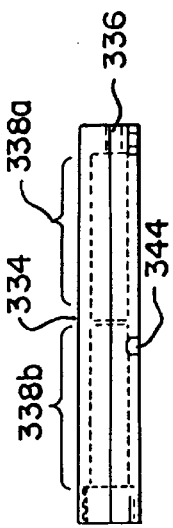

The cylinder 334 has a graduated inside diameter, the smaller-diameter portion 338a, being, e.g., 0.375 in., and the larger diameter portion 338b being, e.g., 0.399 in. (FIGS. 35A and B). The cylinder 334 houses a piston 340 sized to fit in the smaller diameter portion 338a of the cylinder 334, and a spring 342 is interposed between the piston 340 and the end wall of the larger diameter portion 338b of the cylinder. The spring 342 has a spring constant and length selected to maintain the piston 340 in smaller-diameter portion 338a of the cylinder 334 until the fluid pressure reaches the predetermined maximum. When the spring 342 is sufficiently compressed by the fluid pressure to permit the piston 340 to move into the larger-diameter portion 338b of the cylinder 334 (i.e., when the pressure reaches 100 psi), fluid passes around the piston into the larger-diameter portion 338b of the cylinder and exits through an outlet 344 that is in fluid communication with larger-diameter portion 338b of the cylinder. Once the fluid pressure in the system is below the predetermined maximum, the spring 342 biases the piston 340 back into the smaller diameter portion 338a of the cylinder.

As presently contemplated, the piston 340 comprises two parts 340a and 340b that interfit to create a relieved interface which seats a seal (not shown) that maintains fluid-tight contact between the piston 340 and the smaller-diameter portion 338a of the cylinder 334. The piston may be manufactured of a white Delrin material and the seal may be a ring seal, such as that manufactured by Bal Seal Engineering Company of Santa Ana, Calif. under part no. 410 MB-010-G316. The cylinder 334 may be made of a clear polycarbonate, having a polished inside diameter and graduation markings (not shown) on the outside thereof which are visible through the pressure indicator window 314. The graduation markings permit the user to have a visual indication of the fluid pressure in the system based upon the relative position of the piston 340 within the cylinder 334. Further, the spring 342 is preferably stainless steel, such as that manufactured by the Lee Spring Company of Brooklyn, N.Y. having a stock no. of LCM-110E-13-S, standard series. Of course, various other pressure gauges and relief valves as are well-known in the art may be utilized in place of the spring-loaded piston and cylinder arrangement described above.

Like the above-described embodiments, the transfer device 300 also includes a release trigger/release switch mechanism 350 (FIG. 31) for receiving and locking the catheter connector into the transfer device (similar in appearance and operation to the release trigger 172/release switch 170 described above and shown in FIGS. 16–19). The transfer device 300 further includes a pin gate 352 distal of the quartz seed sleeve 308 that blocks the seed lumen to prevent treatment seeds from exiting the transfer device, while still permitting fluid to flow through the seed lumen for, e.g., priming the system. However, the transfer device 300 includes a safety interlock between the release trigger/release switch 350 and the pin gate 352, generally indicated by 354 (best seen in FIG. 40A) that prevents the release switch from being depressed (and thus preventing the user from removing the catheter connector from the transfer device) if the pin gate is retracted to a position that permits treatment seeds to pass through the seed lumen.

Turning to FIGS. 29B, 31, 32B and 32C, there is seen a separate block member 356 that supports on the chassis 304 the release trigger/release switch mechanism 350 and pin gate mechanism 352, generally described above, as well as the quartz sleeve 308 and seed verification system (which is described in greater detail below). Similar to the release switch 170 described above, the release switch 358 (FIG. 38) includes a body portion 358a, preferably made of a Delrin material, with a curved and notched ramp 358b at one end, and the release button 318 secured by a screw 360 (FIG. 31) at the opposite end. Alternatively, the release button 318 may be an integral part of the release switch 358. As described above in connection with release switch 170 and release trigger 172, the curved and notched ramp 358b of release switch 358 engages a circumferentially relieved section 362 on the catheter connector 364 (FIG. 41) to lock the connector into the transfer device. The release switch 358 is depressed to disengage the curved and notched ramp 358b from the catheter connector 364 to permit removal of the connector from the transfer device.

As illustrated, the pin gate 352 (FIGS. 39A, B) is preferably made of stainless steel and has a T-configuration comprising a separate enlarged body 352a that terminates in a slender cylindrical elongated member 352b. A transverse head 352c is supported by the body portion 352b of the pin gate 352. The elongated member 352b of the pin gate 352 has a diameter that is less than the diameter of the seed lumen, so that when interposed through the seed lumen it will block passage of treatment seeds, but allow fluid to pass.

Figure 40B:
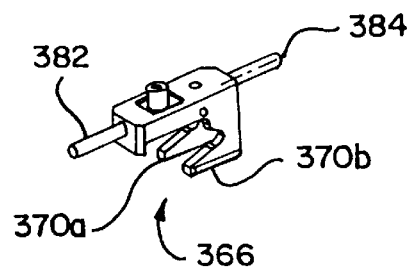
Figure 40C:
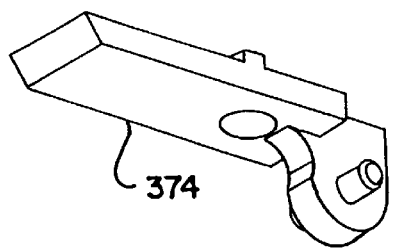
Figure 40D:
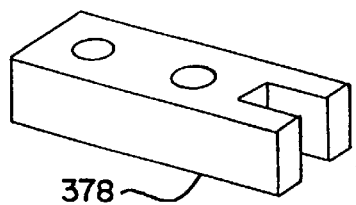

The pin gate 352 is actuated by means of a slider block 366 which is received in an elongated slot 368 (FIG. 31) in the block member 356 and is manipulated by the gate actuator switch 320. With reference to FIG. 40B, the slider block 366 includes two generally L-shaped legs 370a and 370b connected to the proximal end of the slider block, with the free ends of the legs forming a ramp that engages the transverse head 352c of the pin gate 352 (best seen in FIG. 32c) to move the pin gate out of the seed lumen when the slider block 366 is moved in a proximal to distal direction. The legs 370a, 370b straddle a guide track 372 (FIG. 32A) formed in the block member 356. A pivoting lock 374 (FIGS. 32C, 40A and 40C) is biased by a spring steel (24 GA) leaf spring 376 to urge the transverse head 352c of the gate pin 352 down the ramp formed by the legs 370a and b when the slider block 366 is moved in a distal to proximal direction, thus causing the pin gate 362 to block the seed lumen. The leaf spring 376 is preferably supported on a block 378 that is secured to the block member 356 by two screws 380 received in tapped holes in the block member 356. It is contemplated that each of the slider block 366, pivoting lock 374 and block 378 will be made of aluminum.

In keeping with the invention, an interlock mechanism is provided between the release switch 358 and the slider block 366. Specifically, the distal end of the slider block 366 includes a extending shaft 382 that prevents the slider block 366 from moving in a proximal to distal direction to retract the pin gate 352 unless the shaft 382 is aligned with a through-hole 358c in the body portion 358a of the release switch 358. (A similar shaft 384 extends from the proximal side of the slider block 366 to limit motion of the slider block in a distal to proximal direction.) However, the through-hole 358c only aligns with the shaft 382 when the catheter is connected to the transfer device and the curved and notched ramp 358b on the release switch 358 engages the relieved section 362 of the catheter connector 364. Thus, the pin gate 352 cannot be retracted by the slider block 366 unless the catheter is connected to the transfer device to align the through-hole 358c with the shaft 382. In addition, when the shaft 382 extends through the hole 358c, the release switch 358 cannot be depressed, thus preventing the release switch 358 from disengaging the relieved section 362 on the catheter connector. Accordingly, the catheter cannot be released by the transfer device if the pin gate is retracted. As an added safety feature, the gate actuator switch 320 is configured to at least partially cover the release button 318 on the release switch 358 when the pin gate 352 is retracted (best seen in FIG. 32C), thus preventing the release button 318 from being depressed.

In keeping with a further aspect of the invention, the catheter connector 364 is provided with a detent that interlocks with the transfer device 300 that must be manually actuated simultaneously with depressing the release button 318 to release the catheter connector 364 from the transfer device. This provides for added safety in that removal of the catheter from the transfer device requires a coordinated action of both hands of the operator.

Figure 41C:
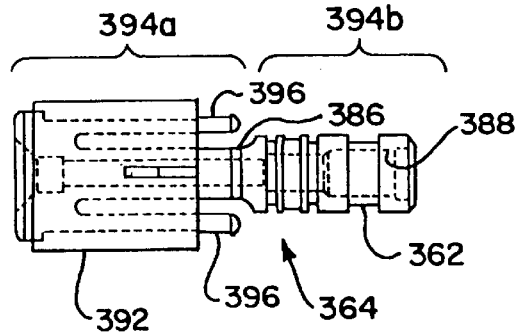

Turning to FIGS. 41A–C there can be seen the catheter connector 364 which includes a central plug portion 386 having a through lumen 388, which receives a connector insert 390 (FIGS. 41E and D, described below) and a sleeve member 392 that overlies the distal portion of the connector 394a, i.e., that portion which remains external to the transfer device when the connector is connected thereto. The proximal portion of the connector 394b is received in the transfer device. The central plug portion 386 of the connector 364 includes two integral, radially-opposed cantilever arms 396 that are connected to the distal end of the central plug 386 and extend axially along, but spaced away from, the central plug portion. The proximal ends of the arms 396 include transverse detent tabs 398 that, when the connector is inserted into the transfer device, snap into contact with a projecting shoulder 400 (FIG. 32C) in the distal end of the transfer device, thus securing the connector in place. To disengage the connector from the transfer device, the cantilever arms 396 must be depressed radially inwardly to allow the detente tabs 398 to clear the shoulder 400. Simultaneously, the release button 318 must be depressed to disengage the release switch 358 from the connector.

In order to prevent foreign matter from contacting the exit of the transfer device through the slots between the cantilever arms 396 and the central plug 386, the sleeve member 392 is fitted over the distal end 394a of the connector, with the proximal end of the sleeve 392 abutting the distal end of the transfer device when the connector is attached thereto. The sleeve member 392 is sufficiently flexible to permit manipulation of the cantilever arms 396 to permit removal of the catheter.

The connector insert 390 (FIGS. 41E and D) has an inner through lumen 402 which is twice stepped along the distal portion of the insert 390. The insert 390 is molded to the most proximal end of the catheter body 404 (seed and fluid return lumens only) and shield tubing 406. The proximal ends of shield tubing 406 and catheter body 404 reside within the stepped portions of the insert 390, and a third channel 408 fluidly connects the seed lumen of the catheter with the chamfered proximal end 410. A second bifurcation 412 occurs within the insert so that the fluid return lumen angles away from the seed lumen and communicates to the exterior of the catheter connector 364 through a curved channel 414 exiting the insert 390 and in alignment with an opening 416 in the side wall of the catheter connector 364. The catheter connector 364 slides over the catheter insert subassembly 418 (FIG. 42A) for positioning the insert 390 within the catheter connector 364. The proximal end of the insert 390 is aligned with the proximal end of the catheter connector 364 and UV cure adhesive is injected into other openings 420 through the connector side wall. The adhesive flows into void areas within the catheter connector through lumen and permanently secures the insert 390 within the catheter connector 364. Alternatively, the catheter connector 364 can be molded over the insert 390 after the insert has been molded to the two lumen catheter portion.

The chamfered portion 410 of the catheter connector 364 fits over a mated projection 422 (best seen in FIG. 32C) at the distal end of the block member 356. This fit properly seats the catheter connector 364 for maximum alignment between the connector lumen and the fluid lumen in the block member 356 and minimizes leakage of fluid at the catheter connector/block member interface.

Turning to FIGS. 42A–D, the catheter 424 of the present invention is similar to the catheters discussed in the above-identified co-pending applications. The catheter 424 has a proximal end 426, a distal end 428, and an elongated portion 430 therebetween. As best seen in FIG. 42D, the catheter 424 has a seed lumen 432, a fluid return lumen 434, and a guide wire lumen 436. The seed lumen 432 and the fluid lumen 434 are contiguous from the proximal end 394b of the catheter connector 364 to the distal end 428 of the catheter 424 and communicate with one another at the distal end 428 of the catheter 424 through an intraluminal connector 438 (FIG. 42C) which is located in the seed lumen 432. The intraluminal connector 438 is preferably made of stainless steel and also reinforces the distal end 428 of the catheter 424 to prevent the treating elements from exiting the distal end of the catheter.

The catheter 424, its seed lumen 432, and its guide wire lumen 436 are all of a generally round cross-section as seen in FIG. 42D. The fluid return lumen 434, however, has an elliptical cross-section to increase the area for fluid flow without compromising the outer diameter of the catheter 424. The greater area lowers the pressure required to send maintain, and return the treating elements. It also decreases the time it takes to transfer the treating elements from the transfer device 300 to the distal end 428 of the catheter 424 and vice versa. However, the fluid return lumen 434 may be of any size or shape to provide for optimal transfer of the treating elements using a limited volume of fluid.

For uniform dosing, it may be determined that the treating elements need to be positioned at or near the center of the luminal wall. In that case, the seed lumen 432 may need to be positioned as close as possible to the center of the catheter 424 to prevent the seed lumen 432 and radioactive elements from lying too close to one side of the luminal wall.

The catheter 424 is preferably made in a single extrusion of 100% low density polyethylene which is very flexible, soft and lubricous. These characteristics allow the catheter 424 to be inserted over a guide wire and into an endoluminal area within the human body without damaging the luminal walls. If a catheter 424 made of 100% low density polyethylene is too soft or pliable, then a polyethylene blend which consists of a certain percentage of both high and low density polyethylene may be used. To maintain flexibility of the catheter, the polyethylene blend must have a higher percentage of low density polyethylene.

Returning to FIGS. 42A–C, an atraumatic tip 440 having a small taper (preferably 11 degrees or less) and a small distal tip radius is fused (possibly with radiofrequency energy) to the distal end 428 of the catheter 424. The fusing process melts the seed lumen 432 and the fluid return lumen 434 closed. The tip 440 is made of polyethylene and preferably with ethylene vinyl acetate. The guide wire lumen 436 extends through the tip 440 and is lined with a sleeve 442 (FIG. 42C) of high density/low density polyethylene. This sleeve 442 is made of a material that is of a higher durometer than the tip 440 to resist the guidewire from tearing the tip 440 as the catheter 424 is delivered over a guidewire.

Radiopaque marker bands 444 made from platinum (90%) –iridium (10%) are located at the distal end 428 of the catheter 424 to assist in proper placement of both the catheter 424 and the treating elements. The marker bands 444 are secured to and flush with the exterior of the catheter 424. Alternatively, radiopaque markers may consist of radiopaque ink or tiny radiopaque particles printed or blasted onto the exterior of the catheter 424. The proximal portion 426 of the catheter may also have a depth marker (not shown) to indicate when the catheter is near the end of the guide wire so that the fluoroscopy can be turned on just prior to the delivery of radiation.

The proximal end 426 of the catheter also has a bifurcation 446 where the guide wire lumen 436 branches off from the catheter portion 430 to a guide wire extension tubing 448. The guide wire extension 448 may include a standard luer 450 with or without a valve for preventing the patient's blood from exiting the proximal end of the guidewire lumen 436. The guide wire extension tubing 448 and the bifurcation 446 can be made of polyethylene or a blend of polyethylene and ethylene vinyl acetate. The seed lumen 432 and the fluid return lumen 434 remain contiguous throughout the bifurcation 446. Strain relief tubing 452 is placed over the proximal end of the catheter portion 430 and extends a short distance from the distal end of the bifurcation 446 where it is secured. The strain relief tubing 452 adds rigidity near the bifurcation 446 for protection from kinks or other damage to the catheter 424. Also, the shield tube 406 fits over the catheter end proximal to the bifurcation 446 for additional protection from the radioactive treating elements as they are transferred into and out of the catheter 424.

At specific times during the radiation therapy procedure, it may be necessary or desired to determine the position of the treating elements and marker seeds with respect to the quartz housing 308 in the transfer device 300. For example, assuming the radiation source train comprises twelve stainless steel encapsulated radioactive treating elements with an inert gold marker seed at each end, the user may need to verify that all twelve treating elements and two marker seeds are present within the quartz housing 308 before delivery of the elements to the distal end of the catheter 424, and for safety reasons must be sure that all of the treating elements and marker seeds are within the quartz housing 308 prior to closing the pin gate 352 and disconnecting the catheter 424 from the transfer device 300.

To determine whether or not all of the treatment elements are within the quartz housing 308, an electronic detection system (shown schematically in FIG. 45), which measures the presence or non-presence of the distal gold marker seed at a single position within the lumen 308a in the quartz housing 308, is included in the transfer device 300. The system detects a gold marker calorimetrically by shining light of different wavelengths onto the small area where the gold marker should reside within the quartz housing 308 and measuring the reflectivity. Based on the wavelength/ reflection ratios of different light, the system determines whether a gold object (gold marker) or non-gold object (stainless steel seed, background, or saline filled lumen 308a in the quartz housing 308) is occupying the area. If a gold marker seed is detected within the small area, it would be reasonable for the user to believe that it is the distal marker seed and that all of the elements proximal to the distal marker seed are also within the quartz housing 308. To increase the degree of certainty that all seeds are within the quartz housing 308, the electronic sensor can be enhanced to determine whether or not both marker seeds are properly positioned within the quartz housing, and/or determine actively whether some or all stainless steel treating elements are properly positioned with the quartz housing. However, this would require providing more space within the housing of the transfer device 300 for the additional electronic and optical components.

In addition to detecting the absence or presence of gold marker at a specific position along the quartz lumen 308a, the electronics wait in a low power state for the power button 312 to be pressed. Then the two indicator LEDs 310a and 310b are flashed on and off for several seconds after the power button 312 has been pressed to indicate that the LEDs 310a and 310b and battery 454 are functional, and then indicate whether or not a gold marker is detected by illuminating one of two indicator LEDs 310a, 310b. A single C-cell lithium battery 454 is shown in FIGS. 29B, 31, 32B and 37 for powering the electronic system. However, the electronic system is preferably powered by two thin batteries which are used in series to produce +6 v from a single battery pack. The output is also inverted to produce a –6 v voltage. Finally, the electronics automatically return to the low power state after one minute has elapsed to conserve the battery power, or restart the one minute timing period if the button is pressed again during that one minute.

Referring to the logic diagram shown in FIG. 45, the battery is indicated by 456. The power supply is controlled by a sleep circuit. Applying power turns the sleep circuit off which in turn shuts down the power supply so that it draws only enough power to keep the system alive. The on-switch 458 is a normally open push button switch 312. When the switch 458 is closed by pressing the button 312 from the exterior of the transfer device 300, the sleep circuit wakes up and turns on the power supplies 460, 462, one generating +6 v and the other generating –6 v. The power generated is first applied by starting an internal timer 464 set for approximately one minute. This internal timer 464 is an analog circuit, but can be a digital circuit using a counter for greater precision and longer times. At the end of one minute the power supplies 460, 462 are turned off and the sleep circuit goes back to sleep until the next time the switch 458 is closed. If the button 312 is pressed during the one minute timing period, the timing period is reset allowing the power to stay on longer than one minute in total. The internal timer 464 can be designed for other lengths of time. Each time the one minute timer 464 is started, a four second test phase 466 also begins and enables a four Hz oscillator 468 which generates a four Hz square wave. The square wave and the four second timer are applied to the indicator LED drivers 470 to flash the two indicator LEDs 310a, 310b (one is green and the other is amber, respectively) on and off simultaneously at four Hz for four seconds. This action informs the user that the battery 454 and indicator LEDs 310a, 310b are in working order. After the four second test phase, the system goes into its normal detection mode.

The detection mode uses the optical properties of stainless steel (the material encapsulating the radioactive isotope) and gold (the material or plated material of the marker seeds) and the effects of red and blue light on each stainless steel and gold seed. The optics of the system include a blue LED 472 employing Gallium Nitride (GaN), a red LED 474 employing Gallium Phosphide (GaP), a photosensor 476 including a photo diode and integrated amplifier, a GRIN (Graded Refractive Index) lens 478, and a second photosensor 480, which are all housed within the block member 356 that houses the quartz sleeve 308. In FIG. 32A, the first photosensor 476 is perpendicularly oriented with respect to the quartz sleeve 308, and the blue and red LEDs 472, 474 are oriented also at an angle on either side of the first photosensor 476. Other orientations of the LEDs relative to the photosensor, and orientations of the photosensor relative to the quartz housing, may be used to increase the accuracy of the electronic detection circuit. Channels 482 within the block member 356 direct light from the LEDs 472, 474 to a targeted location along the quartz sleeve 308 and also direct the reflected light back to the first photosensor 476. The GRIN lens 478, positioned between the quartz sleeve 308 and the first photosensor 476, focuses on the quartz lumen 308a at the site where the distal gold marker should reside when all of the treating elements are within the quartz lumen 308a. The GRIN lens 478 then collects light that is then directed onto the surface of the photo diode.

The blue and red LEDs 472, 474 used in this system supply blue and red light in restricted wavebands that peak at 450 nanometers (nm) and 700 nanometers (nm), respectively. At 450 nm stainless steel (and tinted blue or untinted background) has greater than 90% reflectance and gold has about 35% reflectances; at 700nm both stainless steel and gold have greater than 90% reflectance. This means that stainless steel reflects blue and red light about equally well and gold reflects well in the red light but poorly in the blue light (gold actually absorbs the blue light). Therefore, the measurement of the blue/red ratio of reflected light can unambiguously distinguish between a gold-colored object, in this case a gold marker, or some other object in the photosensor's field of view.

A clock oscillator 484 which oscillates at 3.22 kHz flashes the blue and red LEDs 472, 474 in turn (i.e., 180 degrees out of phase.) The clock oscillator 484 runs through a flip flop 486 where its frequency is divided to create two signals, each having a frequency of 1.61 kHz. One of the two signals is applied to the blue LED driver 490 and the other is applied to the red LED driver 492 so that each LED 472, 474 is driven at approximately 1.61 kHz. Therefore, the on time and the off time of the blue and red LEDs 472, 474 are equal, as they take turns flashing on and off. The flashes of blue and red light travel from the LEDs 472, 474, through channels 482 within the body, and through the quartz sleeve 308 to the targeted location where the distal gold marker should be if all of the seeds are within the quartz lumen 308a. If a stainless steel seed is occupying the targeted location, then both the red and blue light are reflected about equally well (greater than 90%). If nothing but fluid or air fills the quartz lumen at the targeted location, then the background, as long as it is not tinted, also reflects both blue and red light similarly to that of stainless steel. If a gold marker seed is within the targeted location, then the red light is reflected but the blue light is absorbed. The first photosensor 476, consisting of a photo diode and a integrated amplifier, is optically coupled to the targeted location within the quartz sleeve 308 by the GRIN lens 478 so that the photosensor 476 can measure the reflected quantities of each the blue and red lights. From this measurement, the blue/red ratio of reflected light is used to determine the presence or absence of a gold marker.

The viewing window 306 along the top 302a of the transfer device 300 allows ambient light to also be reflected off of the object within the field of view of the photosensor 476. The photosensor 476 will most likely detect the ambient light in addition to the red and blue light. The signal of the ambient light may adversely affect the output of the photosensor 476. The photosensor 476 must be operational even with light coming in through the transparent viewing window. Therefore, the signals due to ambient light sources must be removed from the system. This is done by using a high pass filter 493 which is followed by synchronous detector 494 followed by a low pass filter 496. The synchronous detector 494 is a circuit which is synchronized with the blue and red LED pulses. The synchronous detector 494 removes all AC signals except for those attributable to the blue and red LEDs 472, 474. The low pass filter 496 converts the AC (alternating current) output from the photosensor 476 to a DC (direct current) voltage because the system relies upon the differences between the red and blue signals. A blanking circuit is also included to isolate the low-pass filters for a brief period following each clock transition to improve the accuracy of the low-pass filtered signals. The amplitudes of those signals correspond to how much light is being reflected from the targeted location and the DC voltage is proportional to the blue/red ratio of reflective light. The circuit is adjusted so that, in the case of gold being present at the targeted location, the DC voltage output is zero. In the case of any other object present at the targeted location, the output is a non-null voltage.

The system is designed to produce a null voltage with the detection of gold (and a non-zero voltage with the detection of stainless steel or background) because a null signal is unaffected by any gains encountered along the signal path (zero times any magnitude is always zero); thus, the null signal is much less likely to go outside the tolerance window created around the reference voltage to be detected (null). Because the null signal is less affected by variations within the system, such as mechanical tolerances and temperature changes, it is much more reliable than a non-null voltage. The gold should produce the null because it is the single state that must be distinguished from all others. The only adjustment needed for making the output voltage zero when a gold marker occupies the targeted location is adjusting the intensity with which the blue LED 472 illuminates. Without that adjustment, stainless steel will produce the null because it reflects the blue and red light equally and produces signals close to the same amplitude when the intensity with which the blue and red LEDs 472, 474 illuminate are equal. Two electrical signals of the same amplitude produce zero volts. Conversely, because gold reflects red and absorbs blue when the blue and red LEDs 472, 474 illuminate with the same intensity, the photosensor 476 sends out signals of different amplitudes (high signal for red and low signal for blue) which are converted to a non-null DC voltage. In order for the presence of gold to produce a null, gold, not stainless steel, must produce equal amounts of reflection for both the blue and red lights. This is done by increasing the drive of the blue LED 472 relative to the drive of the red LED 474 so that the blue LED 472 illuminates with greater intensity than the red LED 474. Now gold equally reflects the blue and red lights which produces no AC signal from the photosensor 476, thus, creating a null. On the other hand, the reflection of stainless steel is brighter with the blue because of the boost given to the blue LED driver 490. Therefore, the blue signal is larger than the red signal and the resulting square wave produces a non-zero DC voltage. To make sure the stainless steel treating elements and the background always produce a non-null output voltage, they should be untinted or tinted blue so as to reflect blue and absorb red which is the opposite of what gold does.

When the DC signal is at zero volts, the system will indicate the detection of gold. In practice, however, due to certain variations within the system, the DC signal will almost never read exactly zero volts. Therefore, a window detector 498 with an upper limit reference voltage and a lower limit reference voltage creates a band that is centered on zero. The window detector 498 receives the DC signal and determines whether or not it lies within the set band (for example: −11 to +11 millivolts). If the signal lies within the band, then the window detector decides that the signal is consistent with the presence of gold. The width of the window can be changed in order to vary the tolerance of the system to errors (smaller width for tighter tolerances). After the signal goes through the window detector, the decoded signal enters the two drivers for the indicator LEDs 310a, 310b. If the decoded signal indicates that gold is present, then the green LED 310a along the top 302a of the transfer device 300 is illuminated, displaying to the user that all of the treating elements are within the quartz housing 308; and if the decoded signal indicates that gold is not present, then the amber LED 310b along the top 302a of the transfer device 300 is illuminated, displaying to the user that not all of the treating elements are within the quartz housing 308.

Both the blue and red LEDs 472, 474 are temperature sensitive and their outputs are affected by other factors, such as aging, level of current drive, and possibly ionizing radiation. In particular, the output of the red LED 474 significantly decreases as the temperature rises and significantly increases as the temperature drops. These temperature induced changes in the output of the red LED 474 will disturb the blue/red ratio of reflected light and may hinder the system's ability to detect the presence of gold. To stabilize the output of the red LED 474, a brightness control loop is included to regulate the output and compensate for any temperature effects so as to hold the output of the red LED 474 constant. The blue LED 472, however, is sufficiently temperature stable over the normal operating temperature range of +10° C. to +35° C. Therefore, no brightness control loop is necessary for the blue LED 472. The red LED brightness control loop incorporates the second photosensor 480. The second photosensor 480 compensates for the temperature induced changes in the output of the red LED 474 by "staring" at the tip of the red LED 474 only and measuring how much light it is generating. To best measure the output, the second photosensor 480 is positioned at a 90° angle with respect to the longitudinal axis of the red LED 474. The output signal of the red LED 474 is detected in the same way as the blue/red reflective signal by flowing through the synchronous detector 500a and high and low pass filters 502c, 504a. The outcoming signal then passes through the inverting DC amplifier 506a which sets the control loop gain. The signal provides negative gain to the reference signal (RED_REF) 508c that sets the red LED drive range. The adjusted signal entering the red LED driver 492 attempts to maintain the output of the red LED 474 constant even though the actual amount of light for any given current may be trying to change. This is a very simple control loop; other architectures known to those skilled in the art may be used in its place. A control loop could be added to the blue LED also to improve the stability of its output.

Circuit diagrams corresponding to the logic diagram of FIG. 45 are shown in FIGS. 45A–C. FIG. 46B displays a one minute timer, a +5 power supply and a −5 power supply. FIGS. 46C-1, C-2, and C-3 displays three circuits: a +2.5 reference voltage; processes for the blue signal; and processes for the red signal. FIGS. 46A-1 and A-2 display two LED current drivers, a blanking circuit, a 3 kHz oscillator, a 4 kHz clock, a 4 second timer, a window detector and ±window threshold. These schematics display each component of the electronics and how they interrelate within the electronic system. A specific layout is shown. Other components or layouts which produce the same outcome may be used. The circuits are printed on boards 510a, 512a (FIG. 31) that are mounted to the chassis 304 of the transfer device 300.

As a backup to the electronic source detection system, the window 306 above the quartz housing allows the user of the transfer device 300 to visually detect whether or not all of the treating elements are within the quartz sleeve 308 by either detecting the presence of each marker seed on either side of the treating elements or by counting the number of treating elements and marker seeds within the quartz sleeve 308. To assist the user with visual detection, a magnifying lens 514a (FIG. 32A) is secured to the top portion of the body 302a where it is situated directly above the quartz lumen 308a. The magnifying lens 514a is also located above the indicator LEDs 310a, 310b so that they are also magnified.

Turning to FIGS. 47–51C, there is seen a further improved transfer device 500 of the catheter based radiation delivery system of the present invention. Similar to transfer device 300, transfer device 500 has an exterior which is ergonomically designed to be easily handled by the user and has internal components which include a pressure indicator, pressure relief valve, flow control valve and pathways, quartz housing, a catheter connector/pin gate interlock system, and a treatment element electronic detection system. The improved versions of these and other components, as well as additional features incorporated into transfer device 500 for additional safety and user feedback, are all described in greater detail below.

As seen in the exploded view of FIG. 50, the exterior of the transfer device 500 is made up of an upper portion 502a and a lower portion 502b, each portion comprising a shell half. The two shell halves 502a, 502b fit together to enclose a chassis 504, on which the components of the transfer device 500 are mounted. Openings in the upper shell half 502a allow user access to a power button 506 for activating the electronic detection system and indicator lights 508a, 508b, and a fluid control switch 510 for activating the fluid control valve 512 (FIG. 47). The upper shell portion 502a also includes a pressure indicator window 514, and a magnifying window 516 for viewing the indicator lights 508a and 508b, the quartz sleeve 518 where the treatment elements and marker seeds are stored, and the distal passageways 523 leading from the quartz sleeve 518 to the distal opening 524 of the transfer device 500. The two shell halves 508a and 508b together create openings along the sides of the transfer device 500 that allow access to a fluid entry port 526, a sliding gate actuator switch 528 and either end of a latch mechanism 586 for the catheter connector. Together, the two shell halves 508a and 508b also create an opening 524 (FIG. 49) at the distal end of the transfer device 500 for entry of the catheter connector and an opening at the proximal end of the transfer device 500 allowing access to a fluid exit port 530, which preferably does not extend much, if at all, beyond the exterior wall of the transfer device 500. A compartment for storing a fluid collection bag (described in relation with transfer device 300) may be eliminated to create space inside the transfer device 500 for internal components. Instead a clip may be added to the bottom of the transfer device 500 to secure a fluid collection bag (not shown). Polyurethane is an example of a material that can be used to make the two shell halves 508a and 508b.

The transfer device 500 has a fluid entry port 526 to which a source of pressurized fluid (liquid or gas), such as a fluid filled syringe or automatic fluid pump, is connected for hydraulic or pneumatic delivery and retrieval of treatment elements. The fluid entry port 526 as shown in FIG. 51A has a luer connector. Two offset arms 532a and 532b similar to support arms 326a, 326b described above in connection with transfer device 300 extend from the shell portions 502a and 502b to support and orient a syringe 534a along side transfer device 500 at predetermined angles with respect to its longitudinal axis to afford easier manipulation of the syringe plunger 534b and proper alignment between the distal end of the syringe 534a and the fluid entry port 526. As depicted in FIG. 48, the syringe 534a is angled outwardly approximately seven degrees and upwardly approximately twenty-five degrees with respect to the longitudinal plane of the transfer device 500. The support arms 532a and 532b (FIGS. 47 and 49) are configured such that the arm 532a extending from the upper shell portion is proximal to the arm 532b of the lower shell portion, thus providing a clearer site line between the proximal end of the transfer device 500 and the fluid access 526 port for quick and easy connection of the syringe 534a.

With reference to FIGS. 50–51B and 52, the chassis of transfer device 500 also supports a pressure indicator 536 and a pressure relief valve 538 that work independently from one another. The pressure indicator 536 assists the user in determining the appropriate pressures necessary to send and retrieve treatment elements to and from the distal end of the catheter and to maintain the treatment elements at the distal end of the catheter during treatment. The pressure relief valve 538 prevents overpressurization of the system which could damage the catheter and/or the transfer device 500.

The pressure indicator 536 comprises a hollow cylinder 540 having an inlet port 542 in fluid communication with the fluid source at one end and an end plug 544 at the other end. The cylinder 540 houses a piston 546 and a compression spring 548 residing between the piston 546 and the end plug 544. The piston 546 may be a ring seal as described above in connection with transfer device 300, a rubber plunger obtained from a syringe, or a piston of a harder material with o-ring grooves accommodating o-rings such that they create a seal with the cylinder inside wall. The spring 548 is preferably stainless steel, such as a spring having part number C0300-032-18 manufactured by Mid-West Express Company. The compression spring 548 used must have a spring rate (i.e., the amount of deflection per unit force) that biases the piston 546 to a specific position along the pressure indicator window 514 for the system operating pressures (0 to 100±15 psi). The pressure inside the transfer device 500, created by the fluid source, moves the piston 546 in the cylinder 540 such that it compresses the spring 548 and forces the air on the other side of the piston to escape through a vent opening in the end plug 544. The seal created by the piston 546 about the periphery of the cylinder's inside wall keeps the fluid from passing by the piston 546. As seen in FIG. 47, the piston 546 accommodates a piston ring 550 which is highly visible through the pressure indicator window 514. The piston ring 550 not only serves as the pressure marker but also provides some rigidity along the central portion of the piston 546. Additionally, a background material may be provided along the bottom of the cylinder 540 so as to block the view of other components which may interfere with the visibility of the piston 546 and piston ring 550. However, other standard pressure gauges may be used in place of the spring-loaded piston and cylinder arrangements described above.

Lettering and/or markings 554 are placed on the exterior of the transfer device 500 next to the pressure indicator window 514 to indicate where the piston ring 550 should reside within the pressure indicator window 514 to provide the appropriate pressure for transferring the treatment elements to and from the catheter and to indicate where the piston ring 550 should reside to provide the appropriate pressure for maintaining the treatment elements at the distal end of the catheter for the duration of the treatment. The pressure for maintaining the treatment elements at the distal end of the catheter is much less than the pressure required to quickly send and retrieve the treatment elements. Both the pressure indicator 536 and the pressure relief valve 538 are retained by an L-shaped block portion 556 that is mounted to the chassis 504.

The pressure relief valve 538 is a standard valve with an activation pressure of 100±15 psi. Such a valve is that having part number PCRM0000001S, manufactured by The Lee Company of Westbrook, Conn. The pressure relief valve 538 comprises a pin, a ball, a spring, and a spring retainer and is press fitted into a pressure relief valve housing 558. Each end of the pressure relief housing 558 mates with a fluid connector 559 System pressure above 100±15 psi is forceful enough to unseat the spring biased ball and allow the fluid to flow through the valve 538 and exit the transfer device 500 through the fluid exit port 530 into an external fluid reservoir (not shown). Otherwise, the spring biases the ball into a seated position thereby blocking flow through the valve 538 and allowing flow to continue to be safely directed through the system.

The appearance and functionality o f fluid control valve 512 are identical to that of fluid control valve 330 in FIG. 31. The fluid control valve 512 of the present transfer device 500 directs the fluid flow of the system which can be manipulated by toggling the flow control switch 510 between detented send, return, and neutral positions. The valve 512 may comprise four ports 562 and should be capable of withstanding the system's highest operating pressure (i.e. at least 100 to 115 psi), such as valve part no. 0162336 (HV4-4, w/0.040 ports), manufactured by the Hamilton Company of Reno, Nev.

As indicated above, the interior components of the transfer device 500 are constructed separately and mounted to the chassis, where they are joined together for fluid communication by means of tubing (not shown) and barbed connectors, such as 542 shown in FIG. 52. FIG. 53 is a flow control diagram that visually explains fluid flow of the system.

Turning to FIGS. 48 and 50–51C, the transfer device 500 further includes a separate block member 564 which is mounted to the chassis 504 and houses the quartz sleeve 518, a pin gate mechanism 576, and the optics portion of a seed verification system. As an improvement to the block member 564 described earlier in connection with transfer device 300, the present block member 564 has a mated projection 566 that is machined below the surface of the block member 564 such that it is recessed within a cavity 568. This simplified design reduces the number of components by allowing an o-ring groove 570 to be cut directly into the block member cavity 568 wall surrounding the mated projection 566.

The block member 564 may contain a spring loaded assembly (not shown) to hold the quartz sleeve 518 in its proper position (in alignment with the optics for proper seed detection) even when the transfer device 500 is dropped. A lumen 572 extends along the length of the quartz sleeve 518 for storage of the treatment elements and marker seeds when they are not being used to deliver radiation therapy. The quartz sleeve 518 shields the user from beta particles emitted by the treatment elements when stored therein, thus enabling a user to safely handle the transfer device 500. The distal end of the quartz lumen 572 preferably has a chamfer to prevent seed hang-ups when transferring them. As described previously, the entire length of the quartz sleeve 518 can be seen through an opening in the block member 564 which is aligned with the viewing window 516. To provide better visibility of the treatment elements and marker seeds within the quartz sleeve 518, a colored material (preferably white) may be adhered to or placed under the bottom of the quartz sleeve.

The pin gate mechanism 576 consists of a pin gate 578a, cylindrical pin head 578b, slider block 580, pivoting lock 582, leaf spring 584a, and leaf spring block 584b all working together to position the pin gate 578a in an extended (closed) or retracted (open) position relative to the lumen 523 just distal of the quartz sleeve 518 for respectively blocking or permitting passage of treatment elements. The components and functions of the pin gate mechanism 576 are identical to that of pin gate mechanism 352 described above in connection with transfer device 300. However, the pin gate mechanism 576 of the present invention provides an additional safety feature for preventing the pin gate 578a from closing onto and damaging a treatment element. If an attempt to close the pin gate 578a is made while a treatment element is in the pathway of the pin gate 578a, the pivoting lock 582 is oriented in such a way that it does not clear the pathway of the moving slider and prevents any further advancement of the slider, which in turn halts the downward motion of the pin onto the treatment element. Additionally, the pin gate mechanism 576 may be positioned such that the pin gate 578a is extended and retracted into the distal end of the quartz lumen 572 through a radial channel extending from the top of the quartz sleeve 518 and intersecting with the quartz lumen 572.

Figure 54B:
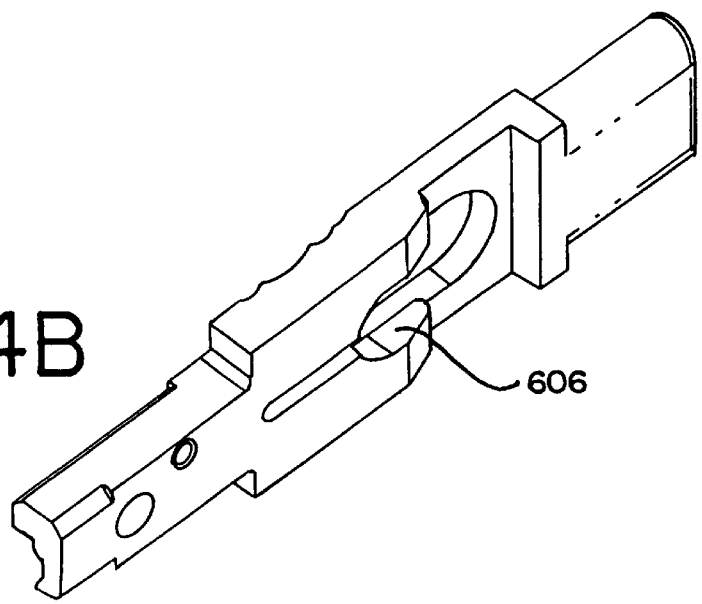
Figure 56B:
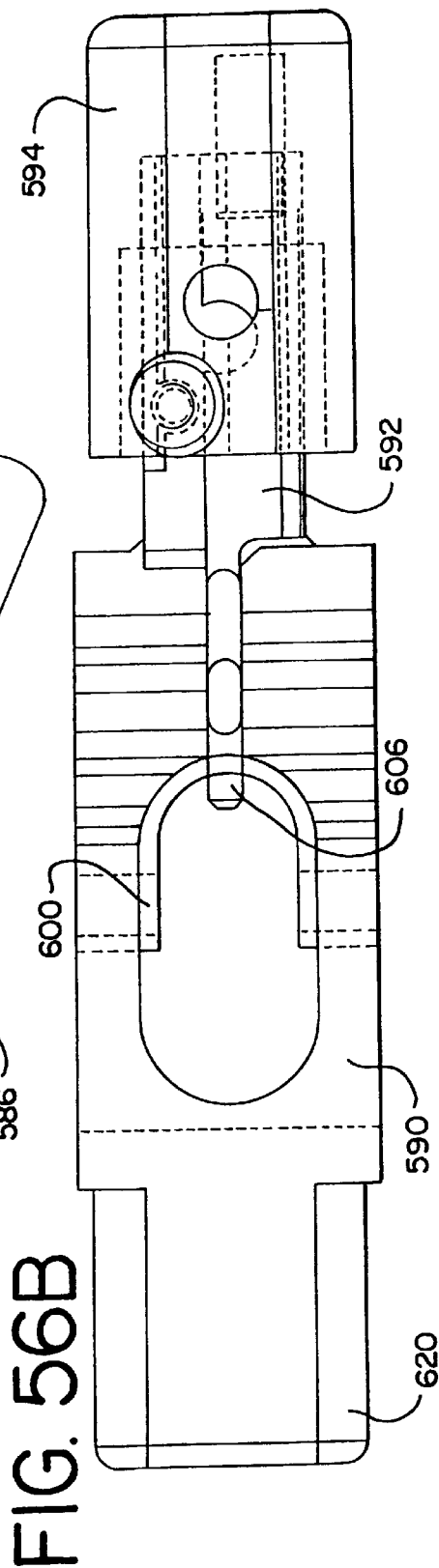
Figure 56C:
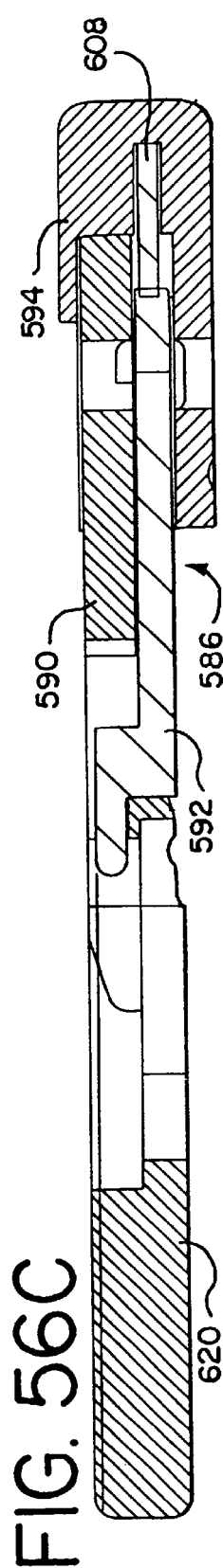

In place of a release trigger/release switch mechanism 350 (shown in FIG. 38), the present transfer device 500 includes a latch mechanism 586 (shown in FIGS. 48, 51A, and 54A–56C) for receiving, locking, and properly seating the catheter connector in the transfer device. The components of the latch mechanism 586 include a latch body 590, a latch sear 592, a latch button 594, and two ball and spring plungers 596, all of which reside in between the block member 564 and end body 598 of the transfer device 500. As illustrated in FIGS. 54A–B and 56B, the latch body 590 is generally rectangular with an elongated opening as seen from its distal face and a raised portion with a U-shaped recess as seen on its proximal face. The U-shaped recess is adjacent to the elongated opening, extends partially along the opening's length, and is accessible therethrough. Because the U-shaped recess is smaller than the elongated opening, some of the raised U-shaped portion 600 surrounding the recess overlaps a portion of the elongated opening. The latch body 590 is preferably made from an opaque material (such as Delrin) to provide lubricity between it and the polycarbonate pieces (i.e. block portion 564 and end body 598) with which it will be in sliding contact. The latch sear 592 (FIGS. 55 and 56B–C) fits within a similarly shaped recessed portion along the proximal face of the latch body 590 such that the small end 606 of the latch sear 592 extends within the elongated opening (FIG. 56B). The latch button 594 houses a compression spring 608 and slides over the upper ends 610 and 612 of the latch sear 592 and latch body 590 such that the latch sear 592 and compression spring 608 are in contact with one another and the latch button 594 is secured to the latch body 590. The ball and spring plungers 596 (FIG. 50) extend from shallow bores within the end body 598 such that each of the two balls rests within one of the valleys 614 along the proximal face of the latch body 590 in between the elongated opening and the extended portion with the through hole.

As a catheter connector 588 is being inserted into the transfer device 500, the distal end of the connector 588 passes through the unobstructed half of the elongated opening of the latch body 590 and seats itself on the mated projection 566 extending from the block member 564 (FIGS. 51A–B). To lock the connector 588 into the transfer device 500, the latch button 594 is pressed inward to facilitate engagement of the relieved section of the connector 588 with the U-shaped portion 600 that overlaps the elongated opening in the latch body 590. As the latch body 590 is moved from the unlatched position to the latched position, the ball of each of the two ball and spring plungers 596 is ramped onto one of the peaks 616 adjacent the valleys 614 on the proximal face of the latch body. This ramping causes the spring biased plungers 596 to compress and force the latch body 590 and engaged connector 588 toward the mated projection 566 at the distal end of the block member 664; thus, ensuring that the chamfer 618 of the connector insert 632 is completely seated against the projection 566 and in complete alignment with its opening. As an indication that the connector 588 has been fully engaged, the free end 620 of the latch body 590 (opposite that end connected to the latch button 594) pops out from the side of the transfer device 500 (FIGS. 47, 48, and 51A). If a band 622 or other marking on the free end 620 is fully visible, then the user can be sure that the connector 588 is now locked into the transfer device 500. To disengage the connector 588 from the transfer device 500, the free end 620 of the latch body 590 is pushed inward to remove the U-shaped portion from the relieved area of the connector 588.

To provide a safer transfer device, an interlock mechanism exists between the latch body 590 and the slider block 580 as can be seen in FIGS. 48 and 51A. The slider block 580 slides toward the distal end of the transfer device 500 to retract the pin gate 578a and thus, allow the treatment elements to be delivered out of the transfer device 500. To enable this movement, the shaft 581 extending from the distal end of the slider block 580 and the through holes of the latch button 594, latch sear 592, and latch body 590 must all be in alignment. When the latching mechanism 586 is in the unlatched position, regardless of whether or not a connector 588 is inserted into the transfer device 500, the extending shaft 581 does not align with the through holes and additionally, the actuator switch 528 is impeded by the popped up latch button 594. When the latching mechanism 586 is in the latched position and no connector 588 is locked into the transfer device 500, the through hole in the latch sear 592 does not completely align with the through hole in the latch button 594 and movement of the slider block 580 is impeded by the latch sear 592. However, when the connector 588 is inserted into the transfer device 500 and the latch body 590 is slid toward the connector 588 for engagement purposes, the small end 606 of latch sear 592 collides with the connector 588 just above the connector's relieved portion 589 and is forced toward the latch button 594 and against the spring 608 such that the sear's through hole now aligns with both the latch body through hole and the latch button through hole. Thus, the pin gate 578a can only be retracted to an open gate position when the connector 588 is inserted into the transfer device 500 and fully engaged by the latching mechanism 586. Furthermore, when the necessary conditions are met and the shaft 581 extends through all three holes as seen in FIG. 51A, the latch body 590 cannot be slid back to the unlatched position, thus preventing the latch body 590 from disengaging the relieved portion 589 on the connector 588. As an extra safety caution and a visual reminder to the user that the connector 588 is not to be disengaged from the transfer device 500 while the pin gate 578a is in a retracted position, the actuator switch 528 is configured to at least partially cover the latch button 594, thus preventing the latch body 590 from being moved into the unlatched position.

Turning to FIGS. 57A–58A and 57C, the catheter connector 588, which is a part of the present invention, is provided with detents 626 that interlock with an annular shoulder in the end body 598 of the transfer device 500 and must be manually actuated to withdraw the catheter connector 588 from the transfer device 500 after it has been unlatched by the latching mechanism 586. The catheter connector 588 includes a central plug portion 630 having a through lumen 630 and cantilever arms 634, a connector insert 632 which is received by central plug through lumen 630, and a skirt 636 that fits over the distal portion of the connector 588 that remains outside of the transfer device 500 when the connector 588 is fully connected thereto. The connector insert 632 is identical to the connector insert 390 described above and shown in FIGS. 41E and D. The central plug portion 628 may be identical to the one described above and shown in FIGS. 41C and D or may be slightly different by having the wall between the two-o-rings taper inward from both ends to enhance the sealing effects of the o-rings. The skirt 636 57A—(FIGS. 57A–B and 58A) is threaded over the catheter tubing and then after the connector 588 is bonded to the catheter tubing, it is fitted over a distal portion of the connector 588 which includes the cantilever arms 634. When the connector 588 is fully inserted into the transfer device 500, the skirt 636 covers the slotted portions 642 that remain external to the transfer device 500, abuts the distal tip of the transfer device 500, and surrounds the connector entrance 524 to the transfer device 500. These characteristics of the skirt 636 serve to maintain sterility of the distal portion of the connector 588 as well as prevent foreign matter from contacting the connector entrance to the transfer device 500 through the slotted portions 642 of the central plug 630. As shown in FIG. 57A, the skirt 636 preferably has two opposing rectangular sides 645 for mating with the depressable sides of the cantilever arms 634 and for indicating to the user where to manipulate the cantilever arms 634. The skirt 636 is preferably made of silicone or other material that is flexible enough to permit manipulation of the cantilever arms 636 as the connector 588 is pulled out of the transfer device 500. In addition, the rectangular sides 645 may be thinner than the rest of skirt 636 so as to provide for easier manipulation of the cantilever arms 634. Having to depress the arms 634 while simultaneously pulling on the connector 588 is another safety feature for preventing inadvertent withdrawal of the connector 588 from the transfer device 500.

As seen in FIG. 58A, catheter 647 of the present invention connects to the transfer device 300, 500 by catheter connector 588 to permit delivery of the treatment elements to a selected site within a patient. With reference to FIGS. 58A–C, the catheter 647 and its components (except for the catheter connector as described just previously) are identical to that shown in FIGS. 42A–42D. However, the most distal marker band of the present invention is in closer proximity to the proximal end of the intraluminal connector 646 the intraluminal connector 646 at the distal end of the catheter 647 may be made of platinum/iridium so as to be visible under fluoroscopy and possibly eliminate the need for the distal marker band 652. Also, the catheter fluid lumens 648 and 650 (especially the fluid return lumen 650) shall have dimensions suitable for transmitting hydraulic or pneumatic pressure for movement of the treatment elements within three to ten seconds are preferably dimensioned to provide treatment element send and return times each in the range of three to ten seconds and more preferably within two to six seconds, while not exceeding a 5 French outer catheter diameter, not exceeding a pressure of 100 psi, and using less than 20 cc of fluid to send, maintain, and return the treatment elements.

The treatment elements 658 are preferably radioactive sources as described within application Ser. No. 08/628,231, filed Apr. 4, 1996, and incorporated herein by reference. The treatment elements 658 consist of twelve radioactive cylinders 660 in series and two marker seeds 659a and 659b, one at each end of the radioactive train. The marker seeds 659a and 659b are used to properly position the treatment elements 658 at the treatment site and are preferably gold or gold plated since gold is visible under fluoroscopy, which is used to monitor the radiation delivery. To decrease the source train delivery time to and retrieval time from the distal end of the catheter, the ends of the marker seeds 659 may be slotted or marker seeds can be of gold tubing filled with epoxy. Most preferably, the distal end of the distal marker seed 659 is slotted to prevent it from blocking the opening to the intraluminal connector 646 and the proximal end of the proximal marker seed 659 is slotted.

In addition to the radiation doses described in the above referenced application Ser. No. 08/628,231, a therapeutic radiation dose of 14 Gy at 2 mm in vessels of approximately 2.7 to approximately 3.2 mm in diameter or of 18 Gy at 2 mm in vessels of approximately 3.2 to approximately 4.0 mm in diameter may be administered to the patient.

At specific times during the radiation therapy procedure, it may be necessary or desirable to determine the position of the treating elements 658 and marker seeds 659 with respect to the quartz sleeve 518 in the transfer device 500. For example, the user may need to verify that all twelve treating elements 658 and two marker seeds 659 are present within the quartz sleeve 518 before delivery of the elements to the distal end of the catheter 647, and for safety reasons must be sure that all of the treating elements 658 and marker seeds 659 are within the quartz sleeve 518 prior to closing the gate 578a and disconnecting the catheter 647 from the transfer device 500.

To determine whether or not all of the treatment elements 658 are within the quartz sleeve 518, an electronic detection system, which measures the presence or non-presence of the distal gold marker seed 659 at a single position within the quartz lumen 572, is included in the transfer device 500. This electronic detection system functions similarly to the previously described detection system to determine and indicate whether or not the treatment elements 658 are within the quartz sleeve 518. However, the means employed by the electronic detection to achieve the end result is altered slightly to produce a simpler, more efficient system, and a more accurate reading of the location of the treatment elements 658 and marker seeds 659a and 659b.

The system detects a gold marker calorimetrically by shining light of different wavelengths onto the small area where the gold marker should reside within the quartz housing 518 and then measuring the reflectivity. Based on the way reflectivity varies with wavelength, the system determines whether a gold object (gold marker) or non-gold object (stainless steel seed, background, or saline filled quartz lumen) is occupying the area. If a gold marker seed is detected, it would be reasonable to conclude with a safe degree of certainty that it is the distal marker seed 659b and that all of the elements proximal to the distal marker seed 659b are also within the quartz housing. To increase the degree of certainty that all seeds are within the quartz housing 518, the electronic sensor can be made to determine whether both marker seeds 659a and 659b are properly positioned within the quartz housing 518. However, this will require more space within the transfer device housing for additional electronic and optical components.

In practice, photosensors are not equally sensitive to blue and red light and the intensity of one or the other must be adjusted by a fixed compensation factor to achieve the condition where the photosensor electrical output is the same for both colors. This technique is well known to those well versed to opto-electronics, and it will be assumed in the rest of this description that where it is stated that the red and blue intensities are equal, it is meant that they are equal as measured by the output of the photosensor.

In addition to detecting the absence or presence of a gold marker at a specific position in the quartz sleeve lumen 572, the electronics wait in a low power state for the power button 506 to be pressed, then flash two indicator Light-Emitting Diodes (LEDs) 508a and 508b on and off for about 4.7 seconds after the power button 506 has been pressed to indicate that the LEDs 508a and 508b and batteries 664 are functional, indicate whether a gold marker is detected by illuminating one of two indicator LEDs 508a and 508b, and finally automatically return to the low power state after five minutes has elapsed to conserve the battery power, or restart the five minute timing period if the button 506 is pressed again during those five minutes.

The electronic system is powered by a 6 v battery pack 664 which contains two 3 v lithium cells used in series to produce +6 v. The output is also inverted to produce a −6 v supply required by the electronic circuitry. Examples of such batteries include Sanyo CR-P2, Panasonic CR-P2, and Duracell DL223A batteries. For safety precautions, a fuse is in series with the battery. When necessary, the upper shell half 502a of the transfer device can be removed to replace the battery pack.

The power supply is controlled by a sleep circuit. Applying power turns the sleep circuit off, which in turn shuts down the power supply so that it draws only enough power to keep the system alive. The on-switch 666 is a single pole double throw (SPDT) push button switch 506. When the switch 666 is closed by momentarily pressing the button 506 from the exterior of the transfer device 500, the sleep circuit is awakened and turns on the power supplies 668,670, one generating +5 v and the other generating −5 v. The power generated is first applied by starting the countdown of an internal timer (a counter driven by 27.3 Hz) 672 set for five minutes. At the end of five minutes the power supplies 668, 670 are turned off and the sleep circuit becomes inactive until the next time the switch 666 is closed. If the button 506 is pressed during the five minute timing period, the timing period is reset allowing the power to stay on longer than five minutes. The internal timer 672 can be set for one of several durations in the existing in the existing design. Each time the five minute timer 672 is started, a 4.7 second test phase 674 also begins and enables a 3.4 Hz oscillator 676 which is derived from a 3.5 kHz oscillator 690. The 3.4 Hz oscillator 676 and the 4.7 second time 674 are applied to the indicator LED drivers 677 to flash the two indicator LEDs 508a and 508b (one is green and the other is amber) on and off simultaneously at 3.4 Hz for 4.7 seconds. This action informs the user that the batteries 664 and indicator LEDs 508a and 508b are in working order. After the 4.7 second test phase 674, the system goes into its normal detection mode.

The detection mode uses the optical properties of stainless steel (the material encapsulating the radioactive isotope) and gold (the material or plated material of the marker seeds) and the resulting different reflectivity's of red and blue light on each stainless steel and gold. The optics of the system include a blue LED 678 employing Gallium Nitride (GaN), a red LED 680 employing Gallium Phosphide (GaP), a photosensor 682 including a photo diode and integrated amplifier, a GRIN (Gradient Index) lens 684, and a second photosensor 686, which are all housed within the block member 564 that houses the quartz 518. In FIG. 51C the first photosensor 682 is perpendicularly oriented with respect to the quartz sleeve 518, and the blue and red LEDs 678, 680 are oriented at an angle on either side of the first photosensor 686. Channels 688 within the body direct light from the LEDs 678,680 to a targeted location along the quartz sleeve 518 and also direct the reflected light back to the first photosensor 682. The GRIN lens 684, positioned between the quartz sleeve 518 and the first photosensor 682, focuses on the quartz lumen 572 at the site where the distal gold marker 659b should reside when all of the treating elements 518 are within the quartz sleeve 518. The GRIN lens 684 then produces an image that becomes roughly focused onto the surface of the photodiode. The axes of the GRIN lens, the red and blue LEDs, and the first photosensor must all intersect at or very near the same point along the axis of the quartz housing 518 to reliably determine the presence or non-presence of a gold marker seed.

The blue and red LEDs 678, 680 used in this system supply blue and red light at peak wavelengths of 450 nanometers (nm) and 700 nanometers (nm) respectively. At 450 nm stainless steel has more than 90% reflectance and gold has about 35% reflectance; at 700nm both stainless steel and gold have more than 90% reflectance. This means that stainless steel reflects blue and red light about equally well and gold reflects well in the red light but poorly in the blue light (gold actually absorbs the blue light). Therefore, the measurement of the blue/red ratio of reflected light can unambiguously determine whether or not a gold colored object, in this case a gold marker, is in the photosensor's field of view.

An analog clock oscillator 690 which oscillates at 3.5 kHz runs through a flip flop 692 where its frequency is divided by two to create two signals, each having a frequency of 1.75 kHz, to flash the blue and red LEDs 678, 680 in turn (180 degrees out of phase). One of the two signals is applied to the blue LED driver 694 and the other is applied to the red LED driver 696 so that each LED 678,680 is driven at approximately 1.75 kHz. Therefore, the on time and the off time of the blue and red LEDs 678,680 are equal as they take turns flashing on and off. The flashes of blue and red light travel from the LEDs 678, 680, through channels 688 within the block member 564, and through the quartz 518 to the targeted location where the distal gold marker should be if all of the seeds are within the quartz lumen 572. If a stainless steel seed or fluid is occupying the targeted location, then both the red and blue light are reflected equally well (approximately 96%). If nothing fills the quartz lumen 572 at the targeted location, then the background, as long as it is untinted, also reflects both blue and red light similarly to that of stainless steel. If a gold marker seed is within the targeted location, then the red light is reflected but much of the blue light is absorbed. A first photosensor 682, consisting of a photo diode and an integrated amplifier, is optically coupled to the targeted location within the quartz 518 by the GRIN lens 684 so that the photosensor 682 can measure the reflectivity in each the blue and red light. From the measured reflectivities, the blue/red ratio of reflected light is used to determine the presence or absence of a gold marker.

The viewing window 516 along the top 502a of the transfer device 500 allows ambient light to also be reflected off of the object within the field of view of the photosensor 682. The photosensor 682 will detect the ambient light in addition to the red and blue light. The signal of the ambient light superimposed on the signal of each the blue and red LEDs 678, 680 may affect the output of the photosensor 682. The photosensor 682 must be operational with light coming in through the transparent viewing window 516; therefore, the signals due to ambient sources must be removed from the system. This is done by using in series a high-pass filter 698, a buffer 700, a synchronous detector 702 and a low pass filter 704. The high-pass filter removes all DC (direct current) light signals (e.g. daylight or flashlight); the buffer helps the synchronous detector to reduce background noise by providing a low impedance drive. The synchronous detector is a circuit which is synchronized with the blue and red LED pulses. The synchronous detector processes the blue and red signals using the same 1.75 kHz oscillator used to drive the blue LED 678 and removes all signals except for those attributable to the blue and red LEDs 680 and converts the resulting AC signal to a DC signal. The amplitude of each pulse corresponds to how much light is being reflected from the targeted location and the DC voltage is inversely proportional to the blue/red ratio of reflected light. In the case of gold being present at the targeted location, the DC voltage output is nominally zero. In the case of any other color present at the targeted location, the output is a nonnull voltage. The last step in filtering out signals from ambient light is using a low pass filter to remove the ripple on the DC signal exiting the synchronous detector.

The system is designed to produce a nominally null voltage with the detection of gold (and a positive non-zero voltage with the detection of stainless steel or background) because a null signal is unaffected by any gains encountered along the signal path (zero times any magnitude is always zero); thus, the null signal is much less likely to go outside the tolerance window created around the reference voltage to be detected (null). Because the null signal is less affected by variations within the system, such as mechanical tolerances and temperature changes, it is more reliable than a non-null voltage. After setting the red LED, the only adjustment needed for making the output voltage zero when a gold marker occupies the targeted location is adjusting the intensity with which the blue LED 678 illuminates. Two signals of the same amplitude produce zero volts AC. Conversely, because gold reflects red and absorbs blue when the blue and red LEDs 678, 680 illuminate with the same intensity, the photosensor 682 sends out signals of different amplitudes (high signal for blue and low signal for bred) which are converted into a non-null DC voltage. In order for the presence of gold to produce a null, gold, not stainless steel, must produce equal amounts of reflection for both the blue and red light. This is done by increasing the drive of the blue LED 678 while maintaining the drive of the red LED 680 constant so that the blue LED 678 illuminates with greater intensity than the red LED 680. The amount by which the drive must be increased is that which produces equal amplitudes for both red and blue reflected light. By increasing the intensity of the blue light by a specific percentage, gold now reflects the blue light equally as well as the red in comparison to absorbing the blue when the red and blue LEDs 680, 678 have the same drive. Now gold reflects equal amounts of the blue and red light which produces no AC signal from the photosensor 682, thus, creating a null. On the other hand, the reflection of stainless steel is brighter with blue because of the boost given to the blue LED driver 694; therefore, the blue signal is larger than the red signal and the resulting square wave produces a non-zero DC voltage. To make sure the stainless steel treating elements and the background always produce a non-null output voltage, they should be untinted or tinted blue so as to reflect blue and absorb red, which is the opposite of what gold does.

When the DC signal is at nominally zero volts, the system will indicate the detection of gold. In practice, however, due to certain variations within the system, the DC signal will rarely read as zero volts. A positive threshold detector 706 is included in the system to compare the threshold reference voltage with the filtered and rectified DC signal (a true window detector with both positive and negative thresholds centered around zero is not necessary because signals from the stainless steel seeds, saline, and quartz lumen are found to always be positive). The buffered +2.5 v reference voltage 708 travels through a potential divider 710, followed by a unity gain buffer 712 to generate the threshold reference voltage WIN+ 714. The threshold detector 706 receives the DC signal and determines whether or not it exceeds the positive threshold(for example, +450 millivolts). If the signal does not exceed the threshold, then the threshold detector 706 decides that the signal is consistent with the presence of gold. The threshold can be changed in order to vary the tolerance of the system to errors. After the signal goes through the threshold detector 706, the decoded signal enters the two drivers for the indicator LEDs 508a and 508b. If the decoded signal indicates that gold is present, then the green LED 508a along the top 502a of the transfer device 500 within the quartz retainer 730 is illuminated, displaying to the user that all of the treating elements are within the quartz housing 518. If the decoded signal indicates that gold is not present, then the amber LED 508b along the top 502a of the transfer device 500 within the quartz retainer 730 is illuminated, displaying to the user that possibly not all of the treating elements are within the quartz housing 518.

Both the blue and red LEDS 678, 680 are temperature sensitive. The red LED output significantly decreases as the temperature rises and significantly increases as the temperature drops. These temperature induced changes in the red LED output will disturb the blue/red ratio of reflected light and may hinder the system's ability to detect the presence of gold. To stabilize the red LED output, a brightness control loop is included to regulate the output and compensate for any temperature effects so as to hold the red LED output constant. The blue LED 678, however, is sufficiently temperature stable over the normal operating temperature range of +10° C. to +35° C.; therefore, no brightness control loop is necessary for the blue LED 678. The red LED brightness control loop incorporates a second photosensor 686. The second photosensor 686 compensates for the temperature induced changes in the LED output by "staring" at the tip of the red LED 680 only and measuring how much light it is generating. The second photosensor 686 is positioned at a 90° angle with respect to the longitudinal axis of the red LED 680. The red LED output signal is detected in the same way as the blue/red reflective signal by flowing through a high-pass filter 716, buffer 718, synchronous detector 720 and a low pass filter 722. The outcoming DC signal then passes through the noninverting DC amplifier 724 to set the control loop gain 726. The signal adds either a positive or negative gain to the reference signal (RED_REF) 727 that sets the red LED drive range. The adjusted signal entering the red LED driver maintains the red LED output constant even though the actual amount of light for any given current may vary.

A block diagram of the electronics used to calorimetrically detect the distal gold marker 659b is shown is FIG. 60.

Figures 2, 61A:
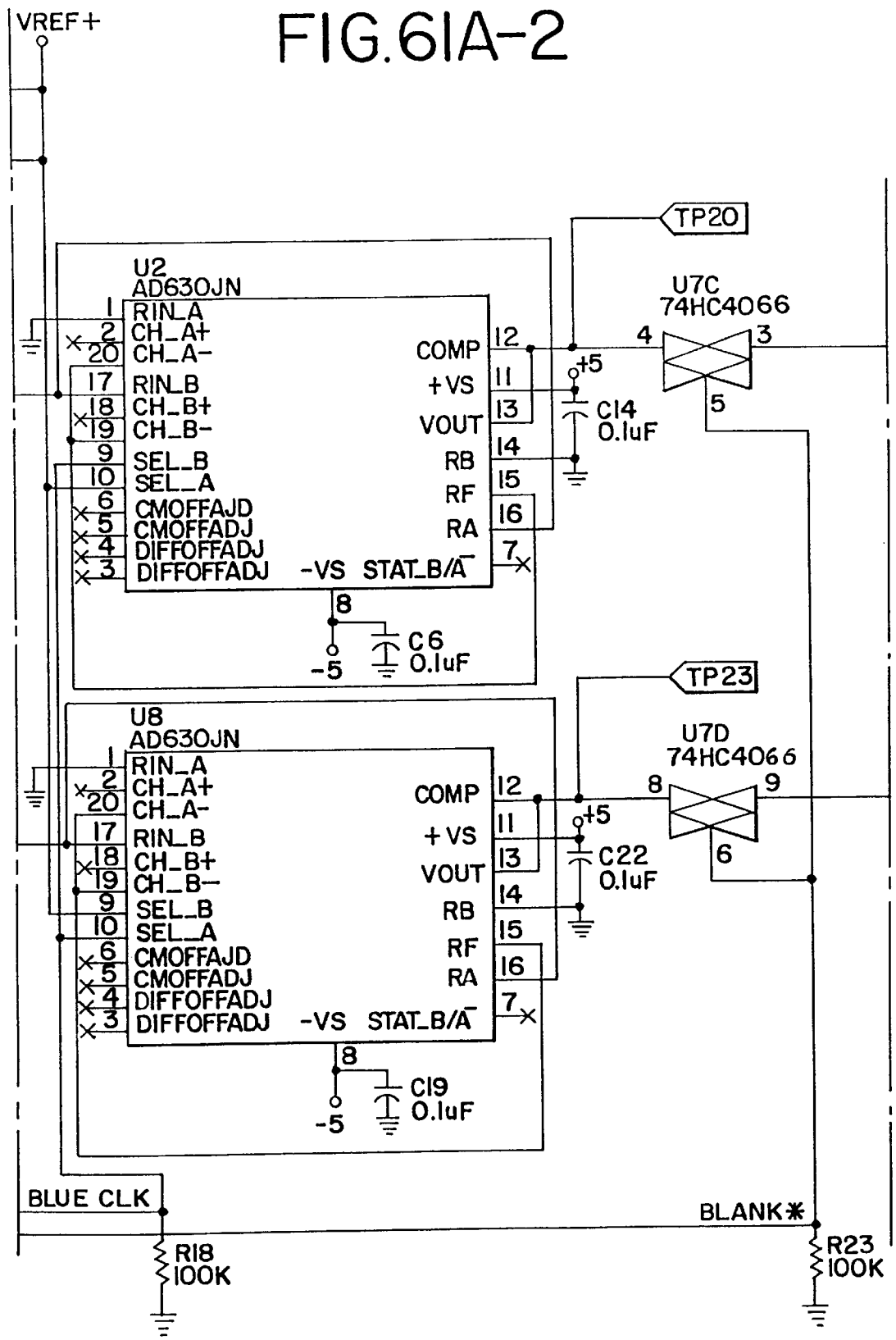
Figures 3, 61A:
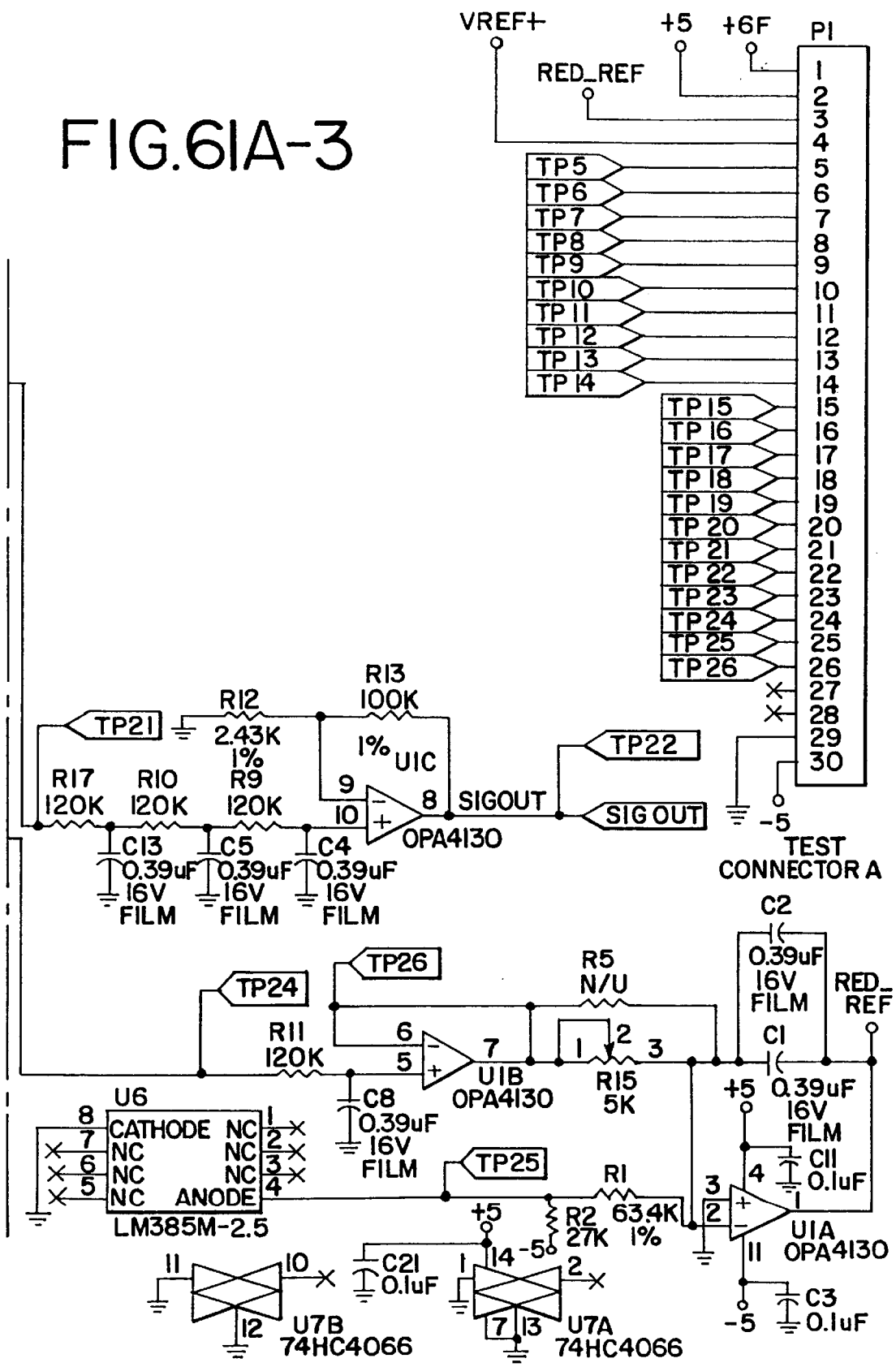
Figure 62B:
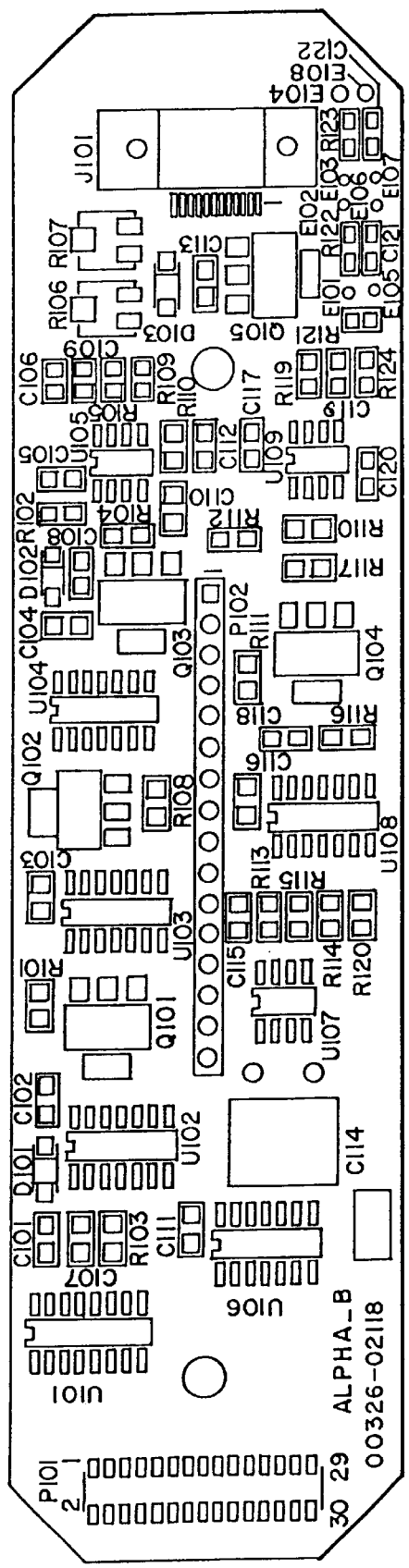
Figure 62C:
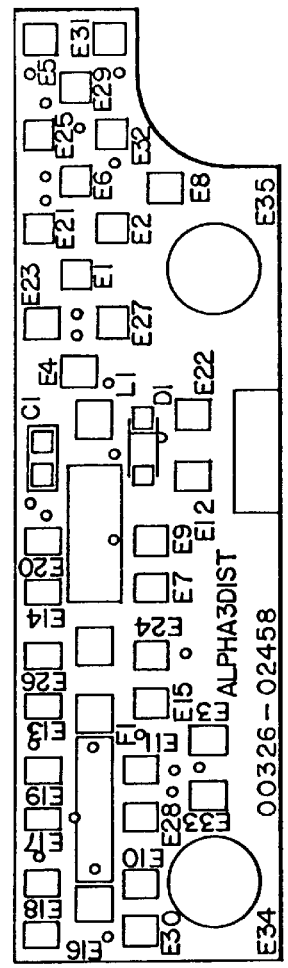

The electronics are built onto two printed circuit boards, PCB A and PCB B. These printed circuit boards can be seen in FIGS. 62A and 62B. For testing procedures each PCB has a test connector which makes accessible signals and voltages within the circuit. The PCB's are stored within a plastic bag for protection against moisture and mounted on the under side of the chassis within the transfer device. The schematic diagrams of the electronics on PCB A are shown in FIGS. 61A–B and the schematic diagram of the electronics on PCB B is shown in FIGS. 61C-1 and C-2. FIG. 61 D is a schematic of the distribution board which is housed on top of the battery pack 664 and FIG. 62C shows the mechanical outline of the distribution board. The electrical connections between the different parts of the detection system are shown in FIG. 63A and an equivalent circuit for the circuitry shown in FIG. 63A in addition to showing how the connections are routed through the distribution printed circuit board and the micro printed circuit boards which are mounted on the two photosensors 682 and 686.

As a backup to the electronic source detection system, a window 516 above the quartz housing 518 allows the user of the transfer device 500 to visually detect whether or not all of the treating elements 658 are within the quartz housing 518 by either detecting the presence of each marker seed 659a and 659b on either side of the treating elements or by counting the number of treating elements 658 and marker seeds 659 within the quartz housing 518. To assist the user with visual detection, a magnifying lens 728, as shown in FIGS. 48, 50, and 51C, is secured to the top portion of the block portion 564 where it is situated directly above the quartz lumen 572. The magnifying lens 728 is also supported by the quartz retainer 730; therefore, the indicator LEDs 508a and 508b are also magnified. The lens used may magnify in one or two dimensions and may have an order of magnification of 2X or greater. The lens is a cylindrical glass lens of plano-convex form. However, other lenses may be used.

Although the above inventions has been described in terms of certain specific embodiments, it is understood that various changes and modifications may be made without departing from these inventions and reference should be made to the appended claims to determine the proper scope of these inventions.

What is claimed is:

1. In a transfer device useable in a system for intraluminal a treatment of a selected site in a body of a patient by at least one treating element having known reflectances for lights of different wavelengths advanced through a lumen in the transfer device into a lumen of a separate catheter, a system for determining the presence or absence of said treating element at a targeted location comprising:

a power source;

a first light source optically connected to the targeted location for emitting a light having a first wavelength;

a second light source optically connected to the targeted location for emitting a light having a second wavelength;

a first photosensor optically connected to the targeted location for measuring the light reflected off the targeted location and creating a signal corresponding thereto;

a window detector for determining whether said created signal is within a predetermined band corresponding to a signal which would be created by light of first and second wavelengths being reflected off the treating element; and at least one indicator light that is activated if said created signal is within said predetermined band.

2. The system of claim 1 wherein each of said first and second light sources comprises an LED.

3. The system of claim 2 wherein said first light source comprises a blue LED and said second light source comprises a red LED.

4. The system of claim 1 wherein said first photosensor comprises a photo diode, a graded refractive index lens for collecting light reflected off the target area and directing the collected light to said photo diode, and an amplifier integrated with said photo diode.

5. The system of claim 2 further comprising a brightness control circuit for holding constant the output of at least one LED, said brightness control circuit comprising:
   a second photosensor optically connected to said LED;
   a synchronous detector and filter for receiving the output of said second photosensor; and
   an amplifier and an integrator to receive the output of said second photosensor and for setting a control loop gain to be added to a reference signal that sets a drive range for said LED.

6. The system of claim 1 further comprising a filter for removing signals generated by said first photosensor due to ambient light.

7. The system of claim 6 wherein said filter comprises a synchronous detector synchronized with signals corresponding to light of said first and second wavelengths and for removing all unsynchronized signals.

8. A system for determining the presence or absence of a gold element at a targeted location, the gold element having known reflectances for lights of different wavelengths, the system comprising:
   a power source;
   a first light source optically connected to the targeted location for emitting a blue light having a first wavelength;
   a second light source optically connected to the targeted location for emitting a red light having a second wavelength;
   a first photosensor optically connected to the targeted location for measuring the light reflected off the targeted location and creating a signal corresponding thereto;
   a window detector for determining whether said created signal is within a predetermined band corresponding to a signal which would be created by light of first and second wavelengths being reflected off the gold element; and
   at least one indicator light that is activated if said created signal is within said predetermined band.

9. The system of claim 8 wherein said first light source comprises a blue LED and said second light source comprises a red LED.

10. The system of claim 9 wherein said blue LED supplies blue light at a peak wavelength of 450 nanometers and said red LED supplies red light at a peak wavelength of 700 nanometers.

11. The system of claim 8 wherein said first photosensor comprises a photo diode, a graded refractive index lens for collecting light reflected off the target area and directing the collected light to said photo diode, and an amplifier integrated with said photo diode.

12. The system of claim 8 further comprising a brightness control circuit for holding constant the output of at least one light source, said brightness control circuit comprising:
   a second photosensor optically connected to said light source;
   a synchronous detector and filter for receiving the output of said second photosensor; and
   an amplifier and an integrator to receive the output of said second photosensor and for setting a control loop gain to be added to a reference signal that sets a drive range for said light source.

13. The system of claim 8 further comprising a filter for removing signals generated by said first photosensor due to ambient light.

14. The system of claim 13 wherein said filter comprises a synchronous detector synchronized with signals corresponding to light of said first and second wavelengths and for removing all unsynchronized signals.

15. A system for determining the presence or absence of an element at a targeted location, the element having known reflectances for lights of different wavelengths, the system comprising:
   a power source;
   a first light source optically connected to the targeted location for emitting a light having a first wavelength;
   a second light source optically connected to the targeted location for emitting a light having a second wavelength;
   a first photosensor optically connected to the targeted location for measuring the light reflected off the targeted location and creating a signal corresponding thereto, said photosensor comprising a photo diode, a graded refractive index lens for collecting light reflected off the target area and directing the collected light to said photo diode, and an amplifier integrated with said photo diode;
   a window detector for determining whether said created signal is within a predetermined band corresponding to a signal which would be created by light of first and second wavelengths being reflected off the element; and
   at least one indicator light that is activated if said created signal is within said predetermined band.

16. A system for determining the presence or absence of an element at a targeted location, the element having known reflectances for lights of different wavelengths, the system comprising:
   a power source;
   a first light source optically connected to the targeted location for emitting a light having a first wavelength;
   a second light source optically connected to the targeted location for emitting a light having a second wavelength;
   a first photosensor optically connected to the targeted location for measuring the light reflected off the targeted location and creating a signal corresponding thereto;
   a brightness control circuit for holding constant the output of at least one light source, said brightness control circuit comprising a second photosensor optically connected to said light source, a synchronous detector and filter for receiving the output of said second photosensor, and an amplifier and an integrator to receive the output of said second photosensor and for setting a control loop gain to be added to a reference signal that sets a drive range for said light source;
   a window detector for determining whether said created signal is within a predetermined band corresponding to a signal which would be created by light of first and second wavelengths being reflected off the element; and at least one indicator light that is activated if said created signal is within said predetermined band.

17. A system for determining the presence or absence of an element at a targeted location, the element having known reflectances for lights of different wavelengths, the system comprising:

a power source;

a first light source optically connected to the targeted location for emitting a light having a first wavelength;

a second light source optically connected to the targeted location for emitting a light having a second wavelength;

a first photosensor optically connected to the targeted location for measuring the light reflected off the targeted location and creating a signal corresponding thereto;

a filter for removing signals generated by said first photosensor due to ambient light;

a window detector for determining whether said created signal is within a predetermined band corresponding to a signal which would be created by light of first and second wavelengths being reflected off the element; and at least one indicator light that is activated if said created signal is within said predetermined band.

18. The system of claim 17 wherein said filter comprises a synchronous detector synchronized with signals corresponding to light of said first and second wavelengths and for removing all unsynchronized signals.

19. The system of claim 15 wherein each of said first and second light sources comprise an LED.

20. The system of claim 16 wherein each of said first and second light sources comprise an LED.

21. The system of claim 17 wherein each of said first and second light sources comprise an LED.

22. The system of claim 19 wherein said first light source comprises a blue LED and said second light source comprises a red LED.

23. The system of claim 20 wherein said first light source comprises a blue LED and said second light source comprises a red LED.

24. The system of claim 21 wherein said first light source comprises a blue LED and said second light source comprises a red LED.

* * * * *